(12) United States Patent
Hamamoto et al.

(10) Patent No.: US 8,697,867 B2
(45) Date of Patent: Apr. 15, 2014

(54) CROSS-LINKED CYCLIC AMINE COMPOUNDS AND AGENTS FOR PEST CONTROL

(71) Applicants: Isami Hamamoto, Odawara (JP); Jun Takahashi, Odawara (JP); Makio Yano, Odawara (JP); Masahiro Kawaguchi, Odawara (JP); Daisuke Hanai, Aizuwakamatsu (JP); Takao Iwasa, Odawara (JP)

(72) Inventors: Isami Hamamoto, Odawara (JP); Jun Takahashi, Odawara (JP); Makio Yano, Odawara (JP); Masahiro Kawaguchi, Odawara (JP); Daisuke Hanai, Aizuwakamatsu (JP); Takao Iwasa, Odawara (JP)

(73) Assignee: Nippon Soda Co., Ltd., Tokyo (JP)

(*) Notice: Subject to any disclaimer, the term of this patent is extended or adjusted under 35 U.S.C. 154(b) by 0 days.

(21) Appl. No.: 13/967,872

(22) Filed: Aug. 15, 2013

(65) Prior Publication Data
US 2013/0331569 A1   Dec. 12, 2013

Related U.S. Application Data

(62) Division of application No. 13/165,223, filed on Jun. 21, 2011, now Pat. No. 8,536,340, which is a division of application No. 12/083,137, filed as application No. PCT/JP2006/320133 on Oct. 6, 2006, now Pat. No. 7,999,102.

(30) Foreign Application Priority Data

| Oct. 6, 2005 | (JP) | 2005-294126 |
| Oct. 6, 2005 | (JP) | 2005-294127 |
| Oct. 12, 2005 | (JP) | 2005-297803 |
| Oct. 12, 2005 | (JP) | 2005-297804 |
| Jan. 25, 2006 | (JP) | 2006-016877 |
| Jun. 30, 2006 | (JP) | 2006-182314 |

(51) Int. Cl.
*C07D 237/08* (2006.01)
*C07D 241/16* (2006.01)
*C07D 221/22* (2006.01)

(52) U.S. Cl.
CPC ............ *C07D 221/22* (2013.01); *C07D 237/08* (2013.01); *C07D 241/16* (2013.01)
USPC ............................ 544/238; 544/336; 546/122

(58) Field of Classification Search
CPC ... C07D 221/22; C07D 237/08; C07D 241/16
USPC .................................. 544/238, 336; 546/112
See application file for complete search history.

(56) References Cited

U.S. PATENT DOCUMENTS

| 4,451,473 A | 5/1984 | Nador et al. |
| 4,968,704 A | 11/1990 | Cross et al. |
| 4,985,063 A | 1/1991 | Fischer et al. |
| 5,001,125 A | 3/1991 | Stokbroekx et al. |
| 5,057,528 A | 10/1991 | Cross et al. |
| 5,364,865 A | 11/1994 | Diana |
| 5,500,423 A | 3/1996 | Glamkowski et al. |
| 5,571,815 A | 11/1996 | Schaper et al. |
| 5,801,173 A | 9/1998 | Lohray et al. |
| 5,859,024 A | 1/1999 | Hotson et al. |
| 5,912,254 A | 6/1999 | Bishop et al. |
| 5,919,782 A | 7/1999 | Lohray et al. |
| 5,922,732 A | 7/1999 | Urch et al. |
| 5,935,953 A | 8/1999 | Kuhar et al. |
| 5,968,947 A | 10/1999 | Urch et al. |
| 6,174,894 B1 | 1/2001 | Urch et al. |

(Continued)

FOREIGN PATENT DOCUMENTS

| EP | 0605031 | 7/1994 |
| EP | 1457490 | 9/2004 |

(Continued)

OTHER PUBLICATIONS

Japanese Patent Office, International Search Report (translated) and Written Opinion dated Oct. 31, 2006, from related International Patent Application No. PCT/JP2006/320133, filed on Oct. 6, 2006 (in Japanese).

(Continued)

*Primary Examiner* — Niloofar Rahmani
(74) *Attorney, Agent, or Firm* — Kenyon & Kenyon LLP

(57) ABSTRACT

Cyclic amine compounds represented by formula (1)

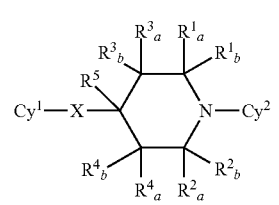

or salts thereof or N-oxides thereof, wherein $Cy^1$ represents an unsubstituted or substituted aromatic ring; X represents oxygen, sulfur, unsubstituted or substituted nitrogen, sulfinyl, or sulfonyl; $R^1_a$ and $R^2_a$, $R^1_a$ and $R^4_a$, $R^2_a$ and $R^3_a$, or $R^3_a$ and $R^4_a$ form saturated rings together; $R^1_a$, $R^1_b$, $R^2_a$, $R^2_b$, $R^3_a$, $R^3_b$, $R^4_a$, $R^4_b$, and $R^5$ which do not form the saturated rings are each independently hydrogen, hydroxyl, halogen, unsubstituted or substituted amino, nitro, or an organic group; $Cy^2$ represents an unsubstituted or substituted aromatic ring with a proviso that $Cy^2$ is an unsubstituted or substituted heteroaromatic ring when $R^1_a$ and $R^2_a$ form a saturated ring together and $Cy^1$ is an unsubstituted or substituted phenyl, and $Cy^2$ is a substituted pyridin-2-yl having one or more cyano as a substituent when $Cy^1$ is an unsubstituted or substituted phenyl and $Cy^2$ is a pyridin-2-yl.

4 Claims, No Drawings

(56) References Cited

U.S. PATENT DOCUMENTS

| | | | |
|---|---|---|---|
| 6,177,442 B1 | 1/2001 | Urch et al. | |
| 6,750,228 B1 | 6/2004 | Barta et al. | |
| 7,199,147 B2 | 4/2007 | Imazaki et al. | |
| 7,485,727 B2 | 2/2009 | Hamamoto et al. | |
| 7,999,102 B2 * | 8/2011 | Hamamoto et al. | 544/238 |
| 8,536,340 B2 * | 9/2013 | Hamamoto et al. | 546/125 |
| 2004/0138286 A1 | 7/2004 | Imazaki et al. | |
| 2004/0147555 A1 | 7/2004 | Fujimoto et al. | |
| 2006/0094767 A1 | 5/2006 | Tsubouchi et al. | |
| 2008/0045569 A1 | 2/2008 | Hamamoto et al. | |
| 2008/0319003 A1 | 12/2008 | Hamamoto et al. | |
| 2009/0099200 A1 | 4/2009 | Li et al. | |
| 2009/0118296 A1 | 5/2009 | Black et al. | |
| 2009/0143443 A1 | 6/2009 | Hamamoto et al. | |
| 2009/0259046 A1 | 10/2009 | Hamamoto et al. | |

FOREIGN PATENT DOCUMENTS

| | | |
|---|---|---|
| JP | 58-49383 | 3/1983 |
| JP | 02-111773 | 4/1990 |
| JP | 6-211839 | 8/1994 |
| JP | 7-506347 | 7/1995 |
| JP | T-09-502446 | 3/1997 |
| JP | WO 97/41120 | 11/1997 |
| JP | 2001-081071 | 3/2001 |
| JP | 2001-504476 | 4/2001 |
| JP | 2001-506989 | 5/2001 |
| JP | 2003-40773 | 2/2003 |
| JP | 2003-137865 | 5/2003 |
| JP | 2001-081071 | 3/2007 |
| TW | 200642591 | 12/2006 |
| WO | WO 97/28128 | 8/1997 |
| WO | 98/22462 | 5/1998 |
| WO | 01/38325 | 5/2001 |
| WO | WO 02/81448 | 10/2002 |
| WO | WO 02/89803 | 11/2002 |
| WO | 02/100833 | 12/2002 |
| WO | 03/097604 | 11/2003 |
| WO | 2004/033463 | 4/2004 |
| WO | WO 2004/099160 | 11/2004 |
| WO | 2005/014578 | 2/2005 |
| WO | WO 2005/036961 | 4/2005 |
| WO | 2005/095380 | 10/2005 |
| WO | WO 2006/075004 A2 | 7/2006 |

OTHER PUBLICATIONS

Taiwanese Preliminary Examination Report, Taiwanese Patent Application No. 095137297, dated Aug. 25, 2009 (English-language translation provided).
European Search Report, European Patent Application No. EP 06 81 1460, dated Jul. 22, 2010.
Korean Notice of Allowance, issued Dec. 1, 2010 during the prosecution of Korean Application No. 2008-7007883.
Search Report, European Patent Application No. 06 81 1453, dated Aug. 3, 2010.
Lohray et al., "Novel Euglycemic and hypolipidemic agents. 4. pyridyl- and quinolinyl-containing thiazolidinediones," *J Med. Chem*, 1999, vol. 42, pp. 2569-2581.
Chemical abstracts, Lohray et al., "Novel Euglycemic and hypolipidemic agents. 4. pyridyl- and quinolinyl-containing thiazolidinediones,", XP002573019, Database accession No. 1999: 384967.
Chemical abstracts, Lohray et al., "Thiazolidinedione compounds having antidiabetic, hypolipidemic, antihypertensive properties, process for their preparation and pharmaceutical compositions," XP002573018, Database accession No. 1999: 430613, pp. 1-2.
International Search Report, International Application No. PCT/JP2005/006887, dated Jun. 21, 2005.
Supplementary Search Report, European Application No. EP 05 72 8646 dated Mar. 26, 2010.
Indian Examination Report, Indian Patent Application No. 2652/KOLNP/2006, dated Jun. 22, 2010.
Office Action, U.S. Appl. No. 12/333,227, dated Jul. 19, 2010.
Office Action, U.S. Appl. No. 12/142,637, dated Aug. 2, 2010.
Patent Abstracts of Japan for JP 2001-081070 published Mar. 27, 2001.
Cooper, R. D. G., et al., "A Chiral Synthesis of D-Homoserine and its Application to the Synthesis of Nocardicin A," *Tetrahedron Letters*, 1978, No. 26., p. 2243-2246.
Albert, Jeffrey S., et al., "Design, Synthesis, and SAR of Tachykinin Antagonists: Modulation of Balance in NK1/NK2 Receptor Antagonist Activity," *Journal of Medicinal Chemistry*, 2002, vol. 45, No. 18, p. 3972-3983.
Eichler, Eva, et al., "1,8-Naphthyridines. Part 1. Synthesis of Some Trifluoromethyl-1,8-naphthyridine Derivatives," *Journal of Heterocyclic Chemistry*, vol. 13, No. 1, Feb. 1976, p. 41-42.
Lowe, John A., et al., "Aza-Tricyclic Substance P Antagonists," *Journal of Medicinal Chemistry*, vol. 37, No. 18, Sep. 2, 1994, p. 2831-2840.
Ek, Fredrik, et al., "Aromatic Allylation via Diazotization: Metal-Free C-C Bond Formation," *Journal of Organic Chemistry*, vol. 67, 2002, p. 6376-6381.
Kim, Deog-Il, et al., "Synthesis and Pharmacology of Site Specific Cocaine Abuse Treatment Agents: 8-Substituted Isotropane (3-Azabicyclo[3.2.1]octane) Dopamine Uptake Inhibitors," *Journal of Medicinal Chemistry*, vol. 46, No. 8, Apr. 10, 2003, p. 1456-1464.
Ferguson, John R., et al., "Efficient New Syntheses of (+)- and (−)-Anatoxin-a, Revised Configuration of Resolved 9-Methyl-9-azabicyclo[4.2.1]nonan-2-one," *Tetrahedron Letters*, vol. 36, No. 48, 1995, pg. 8867-8870.
Comins, Daniel L., et al., "Reduction of N-Acyl-2,3-dihydro-4-pyridones to N-Acyl-4-piperidones Using Zinc/Acetic Acid," *Journal of Organic Chemistry*, vol. 66, 2001, p. 2181-2182.
Montska, Thomas A., et al., "2,2,2-Trichloroethyl Chloroformate: A General Reagent for Demethylation of Tertiary Methylamines," *Tetrahedron Letters*, No. 14, 1974, p. 1325-1327.
Comins, Daniel L., et al., Addition of Grignard Reagents to 1-Acyl-4-Methoxypyridinium Salts. An Approach to the Synthesis of Quinolizidinones,: *Tetrahedron Letters*, vol. 27, No. 38, 1986, p. 4549-4552.
Taylor, Edward C., et al., A Convenient Synthesis of 1-Aryl-4-Piperidones,: *International Journal of Methods in Synthetic Organic Chemistry*, No. 8, 1981, p. 606-608.
Boswell, Robert F., et al., "Synthesis of Some N-Carboxylic Acid Derivatives of 3-Phenoxypyrrolidines, 4-Phenoxypiperidines, and 3-Phenoxynortropanes with Muscle Relaxant and Anticonvulsant Activities," *Journal of Medicinal Chemistry*, vol. 17, No. 9, 1974, p. 1000-1008.
Idoux, John P., et al., "Aromatic Fluoroalkoxylation via Direct Aromatic Nucleophilic Substitution," *Journal of Organic Chemistry*, vol. 48, No. 21, Oct. 21, 1983, p. 3771-3773.
Gupton, John T., et al., "Regioselective Fluoroalkoxylation and Polyfluoroalkoxylation of Activated Polyhalobenzenes," *Synthetic Communications*, vol. 14, No. 7, 1984, p. 621-629.
González, Concepción, et al., "Chapter 6: Synthesis of Phenols," *The Chemistry of Phenols*, Part 1, 2003, p. 395-489.
McCarthy, James R., et al., "Stereospecific Syntheses of the Four Diastereomeric 2-Amino-5-phenoxycyclopentanols," *Journal of Organic Chemistry*, vol. 50, No. 17, Aug. 23, 1985, p. 3095-3103.
Garner, G.V., et al., "Syntheses of Heterocyclic Compounds, Part XXIV. Cyclisation Studies with ortho-Substituted Arylcarbene and Arylnitrene Precursors," *J. Chem. Soc.*, 1971, p. 3693-3701.
Thomas A. Magee, et al., "Insecticidal Substituted 2-Butanone O-(Methylaminocarbonyl)oximes," *Journal of Agricultural and Food Chemistry*, 1977, 25, 1376-1382.
Kurtz, et al., "Novel Insecticidal Oxathiolane and Oxathiane Oxime Carbamates," *Journal of Agricultural and Food Chemistry*, 1987, 35, p. 106-114.
Henrick et al., "Ovicidal Activity and its Relation to Chemical Structure for the Two-spotted Spider Mite (Tetranychus urticae Koch) in a New Class of Miticides Containing the Cyclopropyl Group," *Journal of Agricultural and Food Chemistry*, 1976, vol. 24, No. 5, p. 1023-1029.

(56) References Cited

OTHER PUBLICATIONS

Dekeyser et al., "Synthesis and Miticidal and Insecticidal Activities of 4- (2-Flurooethyl)—5,6—dihydro—4H-1,3,4 -oxadiazines," *Journal of Agricultural and Food Chemistry*, 1993, 41, p. 1329-1331.

Plimmer, Jack R., et al., "Pesticide" *Encyclopedia of Agrochemicals*, vols. 1-3, Wiley: Hoboken, 2003 p. 1199.

Varma et al., "A Facile One-Pot Synthesis of 2,5-Disubstituted Oxazoles Using Iodobenzene Diacetate," J. Heterocyclic Chem., vol. 35, pp. 1533-1534, Nov.-Dec. 1998.

Office Action issued in U.S. Appl. No. 12/333,227 dated Feb. 23, 2010.

Office Action issued in U.S. Appl. No. 12/142,637 dated Feb. 25, 2010.

Japanese Patent Office, International Search Report (translated) and Written Opinion dated Nov. 7, 2006, from related International Patent Application No. PCT/JP2006/320126, filed on Oct. 6, 2006 (in Japanese).

Office Action issued in U.S. Appl. No. 12/083,127 dated May 17, 2011.

Francoise Bardone-Gaudemar, Allenic and Acetylenic Mono- and Diketones, 3 Ann. Chim. 52-107, Paris 1958 (Abstract Only).

Office Action issued in IL Patent Application No. 178,075 dated Jul. 24, 2011 with English Translation, 3 pages.

Office Action issued in EP Patent Application No. 05728646.0 dated Jun. 9, 2011, 5 pages.

Office Action issued in U.S. Appl. No. 12/083,127 dated Oct. 3, 2011.

Office Action issued in U.S. Appl. No. 12/083,127 dated Jun. 19, 2012, 9 pages.

Non-Final Office Action issued in U.S. Appl. No. 12/083,137 dated Jul. 16, 2010, 14 pages.

Non-Final Office Action issued in U.S. Appl. No. 12/083,137 dated Oct. 22, 2010, 22 pages.

Final Office Action issued in U.S. Appl. No. 12/083,137 dated Mar. 18, 2011, 5 pages.

Non-Final Office Action issued in U.S. Appl. No. 13/165,223 dated Dec. 12, 2012, 10 pages.

Non-Final Office Action issued in U.S. Appl. No. 13/165,223 dated Jan. 31, 2013, 6 pages.

\* cited by examiner

CROSS-LINKED CYCLIC AMINE COMPOUNDS AND AGENTS FOR PEST CONTROL

CROSS-REFERENCE TO RELATED APPLICATIONS

This application is a divisional application of U.S. application Ser. No. 13/165,223, filed on Jun. 21, 2011, which is a divisional application of U.S. application Ser. No. 12/083,137, filed on Apr. 3, 2008, which is a national phase application of PCT/JP2006/320133 filed on Oct. 6, 2006 which claims priority under 35 U.S.C. 119 to Japanese Patent Application No. 2005-294126, filed Oct. 6, 2005, Japanese Patent Application No. 2005-294127, filed Oct. 6, 2005, Japanese Patent Application No. 2005-297803, filed Oct. 12, 2005, Japanese Patent Application No. 2005-297804, filed Oct. 12, 2005, Japanese Patent Application No. 2006-016877, filed Jan. 25, 2006, and Japanese Patent Application No. 2006-182314, filed Jun, 30, 2006, the contents of which are incorporated herein by reference.

FIELD OF THE INVENTION

The present invention relates to novel cyclic amine compounds and agents for pest control which contain these cyclic amine compounds or the like as active ingredients.

DESCRIPTION OF THE RELATED ART

Although many compounds which have insecticidal/acaricidal activities are conventionally known, there are problems such as insufficient effect thereof, limitation of use thereof because of drug resistance problems, occurrence of phytotoxicity or contamination in plant bodies, or strong toxicity against mammalians, fish, or the like. As compounds with backbones similar to those of the compounds of the present invention, compounds represented by the formula below are known.

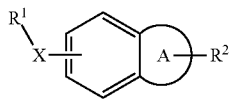

In the formula, X represents —O—, —N($R^3$)—, —S—, or the like and $R^1$ represents a substituted saturated heterocyclic group or the like. As a representative of such compounds, the compound represented by the formula below is known (refer to Patent document 1).

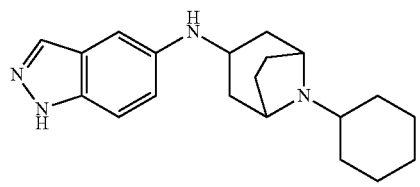 [SMILES: c1cc2[nH]ncc2cc1NC1CC2CCC(C1)N2C1CCCCC1]

Moreover, the compounds represented by the formula below are known.

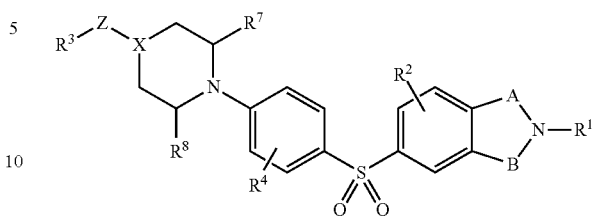

In the formula, X represents —CH— or the like; Z represents a bonding or the like; $R^3$ represents an optionally substituted aryl or an optionally substituted heteroaryl; and $R^7$ and $R^8$ represent —$(CH_2)_s$— or the like together. However, when $R^7$ and $R^8$ represent —$(CH_2)_s$— together, only the compounds where $R^3$ is a substituted phenyl like the compound represented by the formula below are specifically shown as examples (refer to Patent document 2).

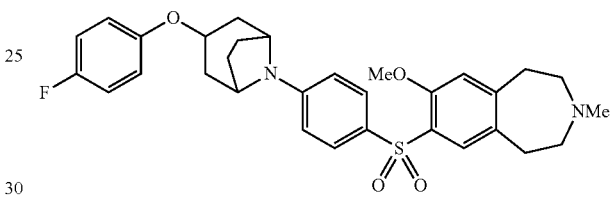

Furthermore, the compounds known in Patent documents 1 and 2 are for medical purposes and their use in the agents for pest control is not described.

[Patent document 1] WO 02/100833
[Patent document 2] WO 05/14578

Problems to be Solved by the Invention

An object of the present invention is to provide agents for pest control, which can be synthesized industrially favorably, which have excellent bioactivities, and which are problem-free in terms of safety.

Means for Solving the Problem

As a result of intensive research in order to solve the above problems, the present inventors discovered that novel cyclic amine compounds with a specific structure have excellent insecticidal/acaricidal activities to complete the present invention. In other words, the present invention firstly provides cyclic amine compounds represented by the formula (1), salts thereof, or N-oxides thereof.

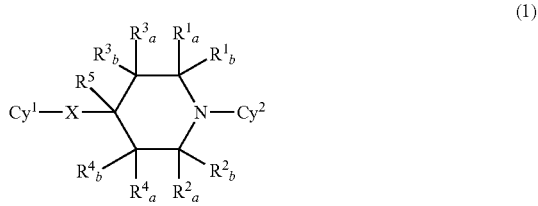

(1)

In the formula, $Cy^1$ represents an unsubstituted or substituted aromatic ring. X represents oxygen, sulfur, unsubstituted or substituted nitrogen, sulfinyl, or sulfonyl. $R^1_a$ and $R^2_a$, $R^1_a$ and $R^4_a$, $R^2_a$ and $R^3_a$, or $R^3_a$ and $R^4_a$ form saturated rings together. $R^1_a$, $R^1_b$, $R^2_a$, $R^2_b$, $R^3_a$, $R^3_b$, $R^4_a$, $R^4_b$, and $R^5$ which do not form the aforementioned saturated rings each independently represents hydrogen, hydroxyl, halogen, unsubstituted or substituted amino, nitro, or an organic group. $Cy^2$ represents an unsubstituted or substituted aromatic ring with a proviso that $Cy^2$ is an unsubstituted or substituted heteroaromatic ring when $R^1_a$ and $R^2_a$ form a saturated ring together and $Cy^1$ is an unsubstituted or substituted phenyl; and $Cy^2$ is a substituted pyridin-2-yl having one or more cyano as a substituent when $Cy^1$ is an unsubstituted or substituted phenyl and $Cy^2$ is a pyridin-2-yl.

Moreover, the present invention secondly provides cyclic amine compounds represented by the formula (2), salts thereof, or N-oxides thereof.

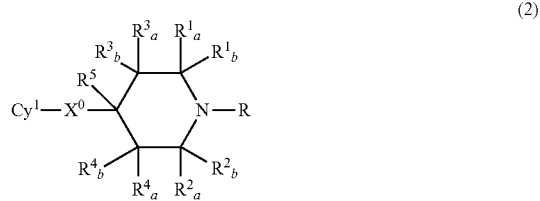

(2)

In the formula, $Cy^1$ represents an unsubstituted or substituted aromatic ring. $X^0$ represents oxygen, sulfur, sulfinyl, or sulfonyl. $R^3_a$ and $R^4_a$ form a saturated ring together. $R^1_a$, $R^1_b$, $R^2_a$, $R^2_b$, $R^3_b$, $R^4_b$, and $R^5$ each independently represents hydrogen, hydroxyl, halogen, unsubstituted or substituted amino, nitro, or an organic group. R represents hydrogen, alkoxycarbonyl, alkylcarbonyl, or 1-alkoxyalkyl.

Furthermore, the present invention thirdly provides agents for pest control, which contains at least one of cyclic amine compounds represented by the formula (3), salts thereof, or N-oxides thereof, as active ingredients.

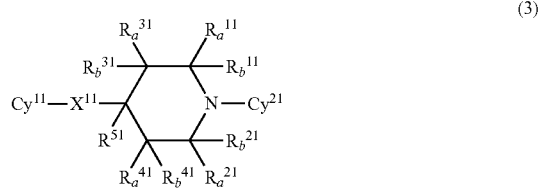

(3)

In the formula, $Cy^{11}$ represents an unsubstituted or substituted aromatic ring. $X^{11}$ represents oxygen, sulfur, unsubstituted or substituted nitrogen, sulfinyl, or sulfonyl. $R^{11}_a$ and $R^{21}_a$, $R^{11}_a$ and $R^{41}_a$, $R^{21}_a$ and $R^{31}_a$, or $R^{31}_a$ and $R^{41}_a$ form saturated rings together. $R^{11}_a$, $R^{11}_b$, $R^{21}_a$, $R^{21}_b$, $R^{31}_a$, $R^{31}_b$, $R^{41}_a$, $R^{41}_b$, and $R^{51}$ which do not form the aforementioned saturated rings each independently represents hydrogen, hydroxyl, halogen, unsubstituted or substituted amino, nitro, or an organic group. $Cy^{21}$ represents an unsubstituted or substituted aromatic ring.

Effects of the Invention

According to the present invention, it is possible to provide cyclic amine compounds with a novel structure, salts thereof, N-oxides thereof, or intermediates thereof during the production, and especially agents for pest control with insecticidal/acaricidal activities for particularly crop-damaging insects and acarids whereby high safety can be provided.

PREFERRED EMBODIMENTS OF THE INVENTION

The present invention will be described in detail below.
1) Cyclic Amine Compounds Represented by the Formulae (1) and (2), Salts Thereof, or N-Oxides Thereof.

In the cyclic amine compounds represented by the formula (1), $Cy^1$ represents an unsubstituted or substituted aromatic ring.

Specific examples of the aromatic rings include aromatic hydrocarbons such as phenyl, naphthalen-1-yl, naphthalen-2-yl; and heteroaromatic rings such as furan-2-yl, furan-3-yl, thiophen-2-yl, thiophen-3-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-5-yl, pyrazol-3-yl, pyrazol-4-yl, pyrazol-5-yl, 1,3,4-oxadiazol-2-yl, 1,3,4-thiadiazol-2-yl, 1,2,3-triazol-4-yl, 1,2,4-triazol-3-yl, 1,2,4-triazol-5-yl, pyridin-2-yl, pyridin-3-yl, pyridin-4-yl, pyridazin-3-yl, pyridazin-4-yl, pyrazin-2-yl, pyrimidin-2-yl, pyrimidin-5-yl, 1,3,5-triazin-2-yl, and 1,2,4-triazin-3-yl; and phenyl is preferable.

Specific examples of the substituents of the aromatic rings include hydroxyl; thiol; halogen such as fluorine, chlorine, bromine, and iodine; cyano; nitro; formyl; unsubstituted or substituted amino such as amino, methylamino, benzylimino, anilino, dimethylamino, diethylamino, and phenylethylamino; alkyl (preferably $C_{1-6}$ alkyl) such as methyl, ethyl, n-propyl, isopropyl, n-butyl, s-butyl, isobutyl, t-butyl, n-pentyl, and n-hexyl; alkenyl such as vinyl, allyl, and 2-methoxyethenyl; alkynyl such as ethynyl, 1-propynyl, 2-phenylethynyl, and propargyl; alkoxy (preferably $C_{1-6}$ alkoxy) such as methoxy, ethoxy, n-propoxy, isopropoxy, n-butoxy, s-butoxy, isobutoxy, and t-butoxy; alkenyloxy such as vinyloxy and allyloxy; alkynyloxy such as ethynyloxy and propargyloxy; aryloxy such as phenoxy and bezyloxy; heteroaryloxy such as 2-pyridyloxy; haloalkyl (preferably $C_{1-6}$ haloalkyl) such as chloromethyl, fluoromethyl, bromomethyl, dichloromethyl, difluoromethyl, dibromomethyl, trichloromethyl, trifluoromethyl, bromodifluoromethyl, 1,1,1-trifluoroethyl, 1-chloroethyl, 2-chloroethyl, 1-bromoethyl, and pentafluoroethyl; haloalkoxy (preferably $C_{1-6}$ haloalkoxy) such as fluoromethoxy, chloromethoxy, bromomethoxy, difluoromethoxy, dichloromethoxy, dibromomethoxy, trifluoromethoxy, trichloromethoxy, tribromomethoxy, 1,1,1-trifluoroethoxy, pentafluoroethoxy, and heptafluoronpropoxy; alkylthiocarbonyl (preferably $C_{1-6}$ alkylthiocarbonyl) such as methylthiocarbonyl, ethylthiocarbonyl, n-propylthiocarbonyl, isopropylthiocarbonyl, n-butylthiocarbonyl, isobutylthiocarbonyl, s-butylthiocarbonyl, and t-butylthiocarbonyl; alkylsulfonylamino (preferably $C_{1-6}$ alkylsulfonylamino) such as methylsulfonylamino, ethylsulfonylamino, n-propylsulfonylamino, isopropylsulfonylamino, n-butylsulfonylamino, and t-butylsulfonylamino; arylsulfonylamino (preferably $C_{6-12}$ arylsulfonylamino) such as phenylsulfonylamino; heteroarylsulfonylamino (preferably $C_{3-12}$ heteroarylsulfonylamino) such as piperazinylsulfonylamino; alkylcarbonylamino (preferably $C_{1-6}$ alkylcarbonylamino) such as methylcarbonylamino, ethylcarbonylamino, n-propylcarbonylamino, and isopropylcarbonylamino; alkoxycarbonylamino (preferably $C_{1-6}$ alkoxycarbonylamino) such as methoxycarbonylamino, ethoxycarbonylamino, n-propoxycarbonylamino, and isopropoxycarbonylamino; haloalkylsulfonylamino (preferably $C_{1-6}$ haloalkylsulfonylamino) such as fluoromethylsulfonylamino, chloromethylsulfonylamino, bromomethylsulfonylamino, difluoromethylsulfonylamino, dichloromethylsulfonylamino, 1,1-difluoroethylsulfonylamino, trifluoromethylsulfonylamino, 1,1,1-trifluoroethylsulfonylamino and pentafluoroethylsulfonylamino; bis(alkylsulfonyl)amino (preferably bis($C_{1-6}$ alkylsulfonyl)amino) such as bis(methylsulfonyl)amino, bis(ethylsulfonyl)amino, (ethylsulfonyl)(methylsulfonyl)amino, bis(n-propylsulfonyl)amino, bis(isopropylsulfonyl)amino, bis(n-butylsulfonyl)amino, and bis(t-butylsulfonyl)amino; bis(haloalkylsulfonyl)amino (preferably bis($C_{1-6}$ haloalkylsulfonyl)amino) such as bis(fluoromethylsulfonyl)amino, bis(chloromethylsulfonyl)amino, bis(bromomethylsulfonyl)amino, bis(difluoromethylsulfonyl)amino, bis(dichloromethylsulfonyl)amino, bis(1,1-difluoroethylsulfonyl)amino, bis(trifluoromethylsulfonyl)amino, bis(1,1,1-trifluoroethylsulfonyl)amino, and bis(pentafluoroethylsulfonyl)amino; unsubstituted or substituted hydrazino such as hydrazino, N'-phenylhydrazino, N'-methoxycarbonylhydrazino, N'-acetylhydrazino, and N'-methylhydrazino; alkoxycarbonyl (preferably $C_{1-6}$ alkoxycarbonyl) such as methoxycarbonyl, ethoxycarbonyl, n-propoxycarbonyl, isopropoxycarbonyl, n-butoxycarbonyl, and t-butoxycarbonyl; aryl (preferably $C_{6-12}$ aryl) such as phenyl, 1-naphthyl, and 2-naphthyl; aralkyl (preferably $C_{7-20}$ aralkyl) such as benzyl, and phenethyl; unsaturated 5-membered heterocycle such as furan-2-yl, furan-3-yl, thiophen-2-yl, thiophen-3-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, pyrazol-3-yl, pyrazol-4-yl, pyrazol-5-yl, 1,3,4-oxadiazol-2-yl, 1,3,4-thiadiazol-2-yl, 1,2,3-triazol-4-yl, 1,2,4-triazol-3-yl, and 1,2,4-triazol-5-yl; unsaturated 5-membered heterocycle alkyl such as 5-phenyl-5-trifluoromethyl-isoxazolin-3-yl, 2-furfurylmethyl, 3-thienylmethyl, and 1-methyl-3-pyrazolomethyl; unsaturated 6-membered heterocycle such as pyridin-2-yl, pyridin-3-yl, pyridin-4-yl, pyridazin-3-yl, pyridazin-4-yl, pyrazin-2-yl, pyrimidin-2-yl, pyrimidin-4-yl, pyrimidin-5-yl, 1,3,5-triazin-2-yl, and 1,2,4-triazin-3-yl; unsaturated 6-membered heterocycle alkyl such as 2-pyridylmethyl, 3-pyridylmethyl, 6-chlor-3-pyridylmethyl, and 2-pyrimidylmethyl; saturated heterocyclic group such as tetrahydrofuran-2-yl, tetrahydrapyran-4-yl, pyrrolidin-2-yl, morpholino, piperidino, and N-methylpiperazinyl; saturated heterocyclic alkyl such as 2-tetrahydrafuranylmethyl, 3-piperazylmethyl, N-methyl-3-pyrrolidylmethyl, and morpholinomethyl; N-unsubstituted- or N-substituted iminoalkyl such as N-dimethylaminoiminomethyl, 1-N-phenyliminoethyl, N-hydroxyiminomethyl, and N-methoxyiminomethyl; N-unsubstituted- or N-substituted hydrazinocarbonyl such as N'-methylhydrazinocarbonyl, N'-phenylhydrazinocarbonyl, and hydrazinocarbonyl; N-unsubstituted- or N-substituted aminocarbonyl such as aminocarbonyl, dimethylaminocarbonyl, and N-phenyl-N-methylaminocarbonyl; allylthio such as methylthio, ethylthio, and t-butylthio; alkenylthio such as vinylthio and allylthio; alkynylthio such as ethynylthio and propargylthio; arylthio such as phenylthio, and 4-chlorophenylthio; heteroarylthio such as 2-piperidylthio and 3-pyridazylthio; aralkylthio such as benzylthio and phenethylthio; alkylsulfonyl such as methylsulfonyl, ethylsulfonyl, and t-butylsulfonyl; alkenylsulfonyl such as allylsulfonyl; alkynylsulfonyl such as propargylsulfonyl; arylsulfonyl such as phenylsulfonyl; heteroarylsulfonyl such as 2-pyridylsulfonyl and 3-pyridylsulfonyl; aralkylsulfonyl such as benzylsulfonyl and phenethylsulfonyl; groups represented by the formulae (a) to (c) below;

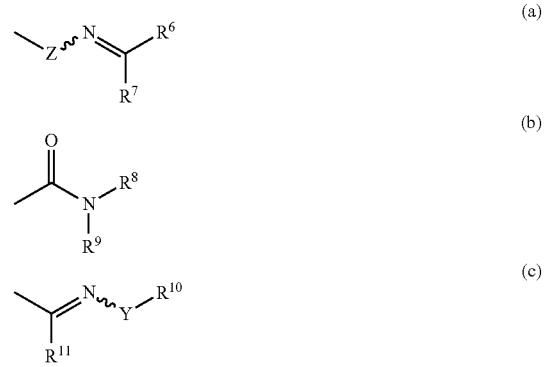

[In the formulae (a), (b), and (c), $R^6$ and $R^7$ each independently represents hydrogen, unsubstituted or substituted hydrocarbon, unsubstituted or substituted heterocyclic group, unsubstituted or substituted amino, hydrocarbonoxy, or hydrocarbonthio; $R^8$ and $R^{11}$ each independently represents hydrogen, unsubstituted or substituted hydrocarbon, unsubstituted or substituted heterocyclic group, or unsubstituted or substituted amino; $R^9$ represents hydrogen or unsubstituted or substituted hydrocarbon; $R^{10}$ represents hydrogen, unsubstituted or substituted hydrocarbon, or unsubstituted or substituted heterocyclic group; Y and Z each independently represents oxygen, or unsubstituted or substituted nitrogen; $R^6$ and $R^7$, $R^8$ and $R^9$, and $R^{10}$ and $R^{11}$ may bond to form rings and in that case, both two groups in the pair represent functional groups, which may integrate to form a ring. Specific examples of hydrocarbons commonly present in $R^6$ to $R^{11}$ include alkyl such as methyl, ethyl, isopropyl, n-propyl, n-hexyl, and n-octyl; alkenyl such as vinyl, allyl, 1-propenyl, and 2-phenylethenyl; alkynyl such as ethynyl and propargyl; and aromatic hydrocarbon such as phenyl, 1-naphthyl, and 9-anthracel. Specific examples of heterocyclic groups commonly present in $R^6$, $R^7$, $R^8$, $R^{10}$, and $R^{11}$ include unsaturated 5-membered heterocycle such as furan-2-yl, furan-3-yl, thiophen-2-yl, thiophen-3-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, pyrazol-3-yl, pyrazol-4-yl, pyrazol-5-yl, 1,3,4-oxadiazol-2-yl, 1,3,4-thiadiazol-2-yl, 1,2,3-triazol-4-yl, 1,2,4-triazol-3-yl, and 1,2,4-triazol-5-yl; unsaturated 5-membered heterocycle alkyl such as 5-phenyl-5-trifluoromethyl-isoxazolin-3-yl, 2-furfurylmethyl, 3-thienylmethyl, and 1-methyl-3-pyrazolomethyl; unsaturated 6-membered heterocycle such as pyridin-2-yl, pyridin-3-yl, pyridin-4-yl, pyridazin-3-yl, pyridazin-4-yl, pyrazin-2-yl, pyrimidin-2-yl, pyrimidin-4-yl, pyrimidin-5-yl, 1,3,5-triazin-2-yl, and 1,2,4-triazin-3-yl; unsaturated 6-membered heterocycle alkyl such as, 2-pyridylmethyl, 3-pyridylmethyl, 6-chlor-3-pyridylmethyl, and 2-pyrimidylmethyl; and saturated heterocycle such as tetrahydrofuran-2-yl, tetrahydrapyran-4-yl, piperidin-3-yl, pyrrolidin-2-yl, morpholino, piperidino, and N-methylpiperazinyl; saturated heterocyclic alkyl group such as 2-tetrahydrofuranylmethyl, 3-piperazylmethyl, N-methyl-3-pyrrolidylmethyl, and morpholinomethyl. Specific examples of hydrocarbonoxy and hydrocarbonthio commonly present in $R^6$ and $R^7$ include methoxy, ethoxy, isopropoxy, phenoxy, benzyloxy, methylthio, ethylthio, phenylthio, and benzylthio. Specific examples of substituents of functional groups present in $R^6$ to $R^{11}$ include the same as those shown as specific examples of the substituents of $Cy^1$.

Y and 2 each independently represent oxygen, or unsubstituted or substituted nitrogen and specific examples of a substituent on nitrogen include the same as those shown as specific examples of the substituents of $Cy^1$.

Specific examples of the group represented by the formulae (a) to (c) include the group represented by the formula below.

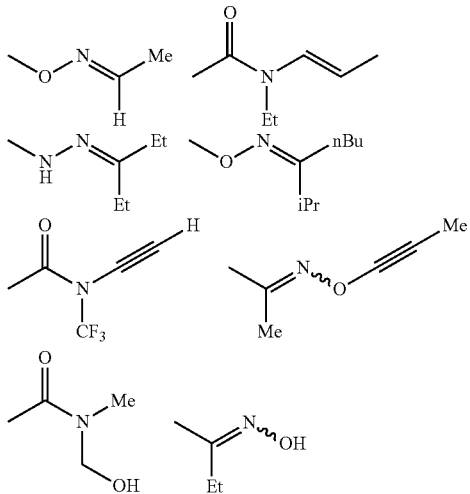

]$C_{1-6}$ haloalkyl is particularly preferable. By associating two or more substituents listed above by substituting one substituent onto another, the resulting substituent can be used in a similar manner as a new substituent.

In formula (1), X represents oxygen; sulfur; unsubstituted or substituted nitrogen; sulfinyl; or sulfonyl and oxygen is preferable. It should be noted that when nitrogen is unsubstituted, hydrogen is bonded to nitrogen.

When X is substituted nitrogen, specific examples of substituents on nitrogen include those similar to the specific examples of the substituents of $Cy^1$.

Moreover, in formula (1), $R^1{}_a$ and $R^2{}_a$, $R^1{}_a$ and $R^4{}_a$, $R^2{}_a$ and $R^3{}_a$, or $R^3{}_a$ and $R^4{}_a$ form saturated rings together and it is preferable that $R^1{}_a$ and $R^2{}_a$ or $R^3{}_a$ and $R^4{}_a$ come together to form a ring and the number of atoms at the cross-linking site of the piperidine ring, which forms the saturated ring, is preferably 2 or 3.

In addition, elements which constitute the cross-linking site of the piperidine ring of the saturated ring are not particularly limited as long as they are within a chemically acceptable range and specific examples thereof include carbon, oxygen, sulfur, nitrogen, or silicon and the saturated rings can be constituted by combining 2 or more of these elements within a chemically acceptable range. Moreover, each atom can have hydrogen or substituents within the chemically acceptable range thereon and $R^1{}_a$ and $R^2{}_a$, $R^1{}_a$ and $R^4{}_a$, $R^2{}_a$ and $R^3{}_a$, or $R^3{}_a$ and $R^4{}_a$ may bind oxygen, sulfur, or nitrogen via a double bond within a chemically acceptable range to form carbonyl, thiocarbonyl, imino, or the like.

$R^1{}_a$, $R^2{}_a$, $R^2{}_b$, $R^3{}_a$, $R^3{}_b$, $R^4{}_a$, $R^4{}_b$, and $R^5$ which do not form the aforementioned saturated rings together each independently represents hydrogen, halogen, unsubstituted or substituted amino, nitro, hydroxyl, or an organic group. The organic group represents functional groups generally which contain carbon and the specific examples thereof include cyano; formyl; alkyl; alkoxycarbonyl; alkoxy; haloalkyl; haloalkoxy; alkylthiocarbonyl; alkylsulfonylamino; haloalkylsulfonylamino; bis(alkylsulfonyl)amino; bis(haloalkylsulfonyl)amino; and aryl; or the like. As the organic groups, alkyl; alkoxycarbonyl; and alkoxy are preferable and $C_{1-6}$ alkyl; $C_{1-6}$ alkoxycarbonyl; and $C_{1-6}$ alkoxy are more preferable. Specific examples thereof include the same as those shown as specific examples of the substituents of $Cy^1$.

Specific examples of a piperidine ring, which is constituted in formula (1), include the structures represented by the formulae shown below.

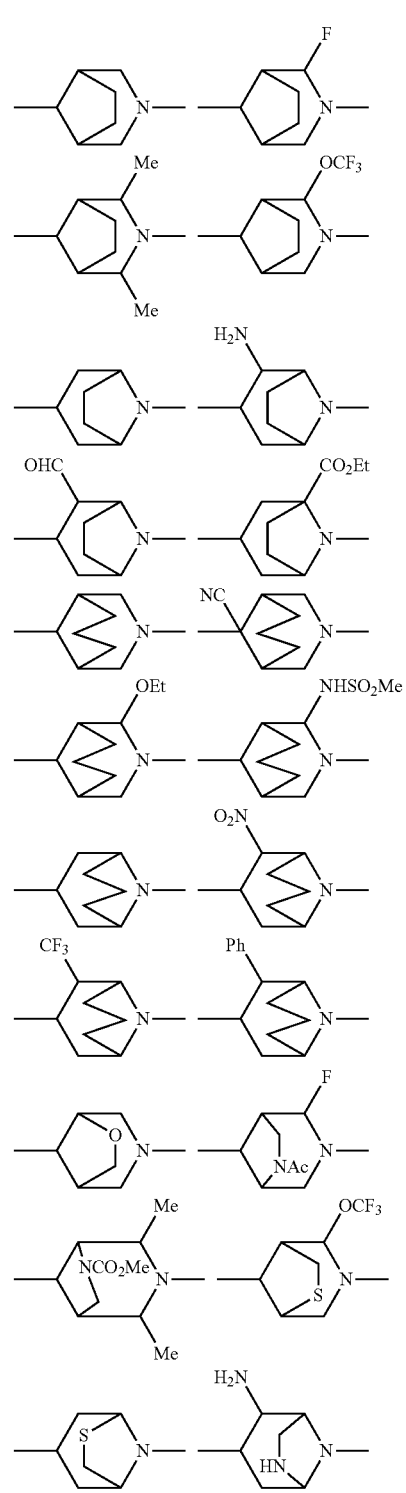

-continued

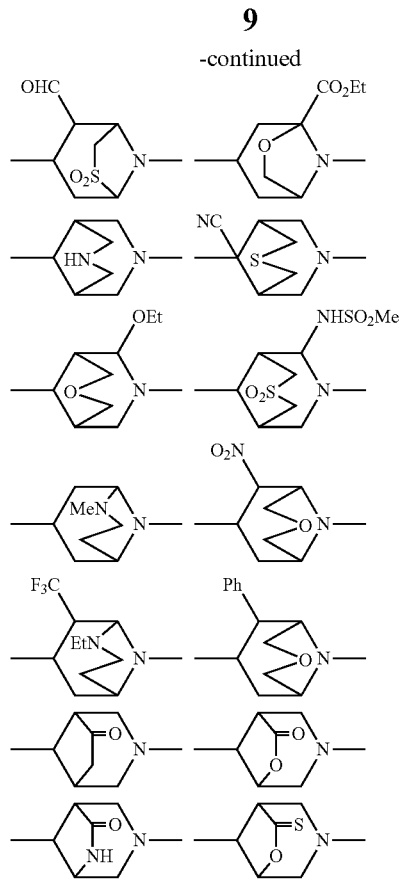

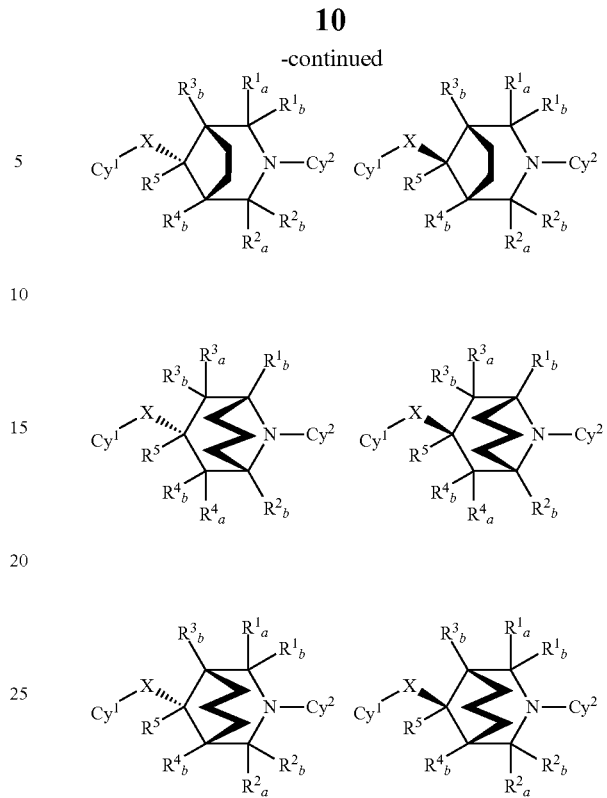

The following compounds can be shown as examples of N-oxides of the compounds represented by the formula (1); i.e. the compounds represented by the formula (1) where nitrogen represented by X or nitrogen in the cyclic amine parts of the tropane ring, isotropane ring, or the like is oxidized.

Moreover, examples of salts of the compounds represented by the formula (1) include salts of inorganic acids such as hydrochloride salts, nitrate salts, sulfate salts, and phosphate salts; and salts of organic acids such as acetate salts, lactate salts, propionate salts, and benzoate salts.

$X^0$ in the formula (2) corresponds to X in the formula (1) except that $X^0$ does not include nitrogen and $R^1_a$ to $R^5$ in the formula (2) are the same as $R^1_a$ to $R^5$ in the formula (1) except that only $R^3_a$ and $R^4_a$ form a saturated ring together.

R represents hydrogen; alkoxycarbonyl such as 1-chloroethoxycarbonyl, methoxymethoxycarbonyl, 1-ethoxyethoxycarbonyl, 1,1,1-trichloroethoxycarbonyl, and others similar to those examples of the specific examples of the substituents of $Cy^1$ such as alkoxycarbonyl (preferably $C_{1-6}$ alkoxycarbonyl); alkylcarbonyl (preferably $C_{1-6}$ alkylcarbonyl) such as methylcarbonyl, ethylcarbonyl, n-propylcarbonyl, isopropylcarbonyl, n-butylcarbonyl, isobutylcarbonyl, s-butylcarbonyl, and t-butylcarbonyl; or 1-alkoxyalkyl (preferably 1-$C_{1-6}$ alkoxyalkyl) such as methoxymethyl, ethoxymethyl, and 1-ethoxyethyl.

Although specific examples of an aromatic ring of $Cy^2$ include those similar to the specific examples of $Cy^1$, pyridazyl is preferable, and pyridazin-3-yl is more preferable with a proviso that $R^1_a$ and $R^2_a$ come together to form a saturated ring and $Cy^2$ is an unsubstituted or substituted heteroaromatic ring when $Cy^1$ is unsubstituted or substituted phenyl. Moreover, $Cy^2$ is a substituted pyridin-2-yl having one or more cyano as a substituent when $Cy^1$ is an unsubstituted or substituted phenyl and $Cy^2$ is a substituted pyridin-2-yl. $Cy^2$ does not include unsubstituted pyridin-2-yl, when $Cy^1$ is an unsubstituted or substituted phenyl. The substituted pyridin-2-yl having one or more cyano as a substituent means that the substituted pyridin-2-yl has only cyano as a substituent or cyano and another substituent as substituents.

Several pairs of isomers exist when $R^1_a$ and $R^2_a$ or $R^3_a$ and $R^4_a$ of the compound (1) of the present invention come together to form a saturated ring. These isomers are all included in the present invention. It should be noted that the same also applies when $R^1_a$ and $R^4_a$ or $R^2_a$ and $R^3_a$ come together to form a saturated ring. Moreover, the same applies to the compounds (2) of the present invention which will be described later.

2) Production Method (1) When X is Oxygen or Optionally Oxidized Sulfur

The compound (1) can be obtained by, for example, obtaining the compound represented by the formula (5) by eliminating protecting group such as methyl and benzyl from the compound represented by the formula (4) (hereinafter referred to as the "compound (4)") as shown below and coupling the compound (5) with the compound represented by the formula (6) by the general method.

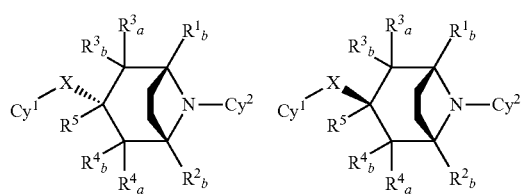

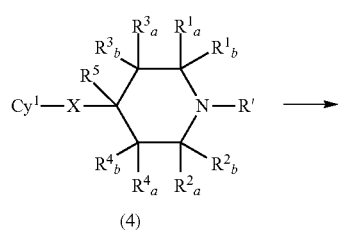

(4)

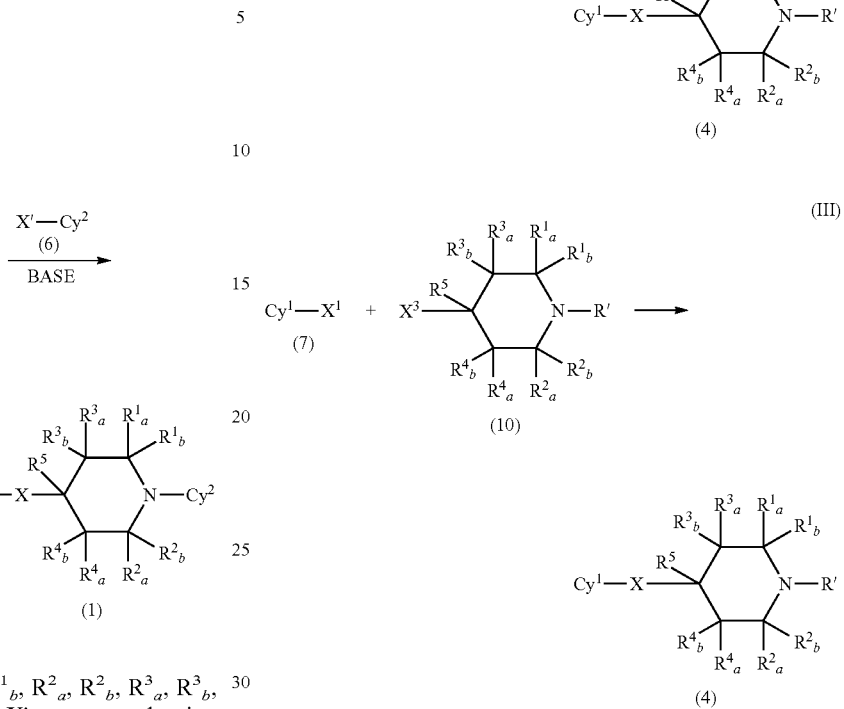

(In the formula, $Cy^1$, $Cy^2$, X, $R^1_a$, $R^1_b$, $R^2_a$, $R^2_b$, $R^3_a$, $R^3_b$, $R^4_a$, $R^4_b$, and $R^5$ are the same as above. X' represents a leaving group such as halogen and R' represents a protecting group.)

The compound (4), which is an intermediate during the production, can be produced by general reaction conditions as described next.

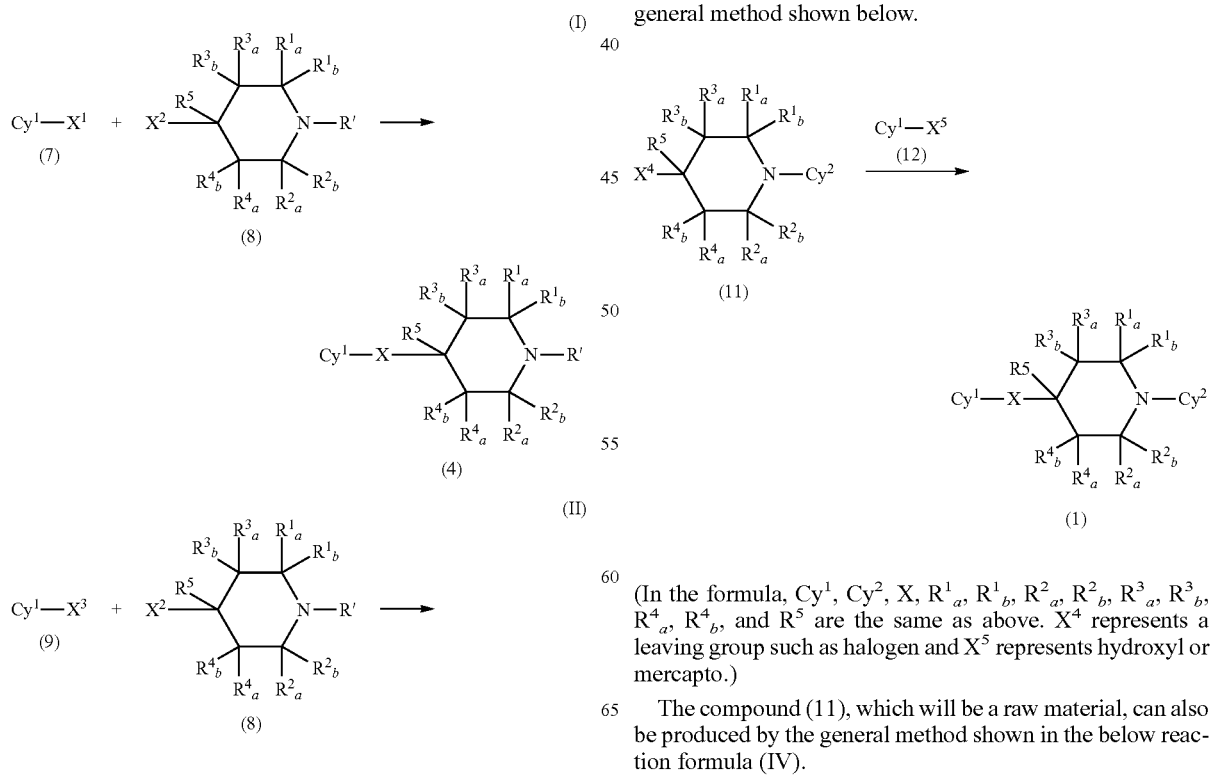

(In the formula, $Cy^1$, X, $R^1_a$, $R^1_b$, $R^2_a$, $R^2_b$, $R^3_a$, $R^3_b$, $R^4_a$, $R^4_b$, $R^5$ and R' are the same as above. $X^1$ and $X^2$ each independently represents hydroxyl or mercapto and $X^3$ represents a leaving group such as halogen.)

Moreover, the compound (1) can also be produced by the general method shown below.

(In the formula, $Cy^1$, $Cy^2$, X, $R^1_a$, $R^1_b$, $R^2_a$, $R^2_b$, $R^3_a$, $R^3_b$, $R^4_a$, $R^4_b$, and $R^5$ are the same as above. $X^4$ represents a leaving group such as halogen and $X^5$ represents hydroxyl or mercapto.)

The compound (11), which will be a raw material, can also be produced by the general method shown in the below reaction formula (IV).

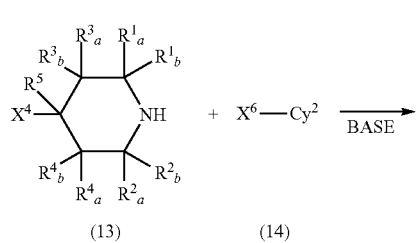

(IV)

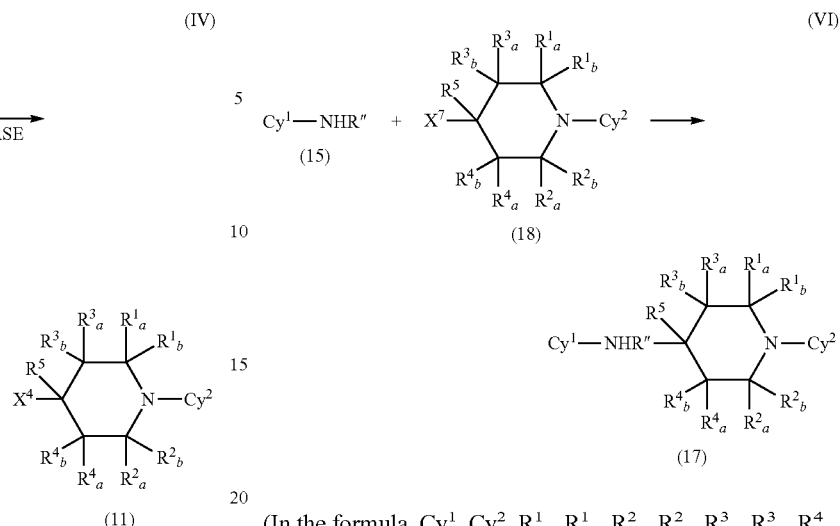

(VI)

(In the formula, $Cy^2$, $X^4$, $R^1_a$, $R^1_b$, $R^2_a$, $R^2_b$, $R^3_a$, $R^3_b$, $R^4_a$, $R^4_b$, and $R^5$ are the same as above. $X^6$ represents a leaving group such as halogen.)

(2) When X is Optionally Substituted Nitrogen

The compounds represented by the formula (17) can be produced by reacting the compounds represented by the formula (15) with the compounds represented by the formula (16) by the general method as shown in the below reaction formula (V).

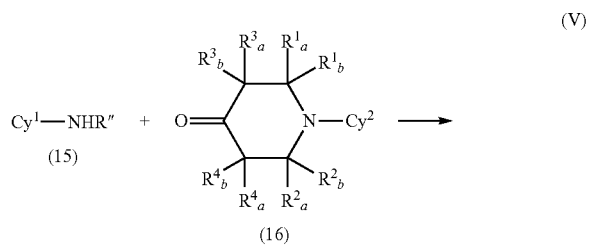

(In the formula, $Cy^1$, $Cy^2$, $R^1_a$, $R^1_b$, $R^2_a$, $R^2_b$, $R^3_a$, $R^3_b$, $R^4_a$, and $R^4_b$ are the same as above. R" represents a substituent on nitrogen such as hydrogen, trifluoroacetyl, or trifluoromethylsulfonyl.)

The compound (17), which is a compound of the present invention, can also be produced by coupling the compound (15) and the compound represented by the formula (18) by the general method as shown in the below reaction formula (VI).

(In the formula, $Cy^1$, $Cy^2$, $R^1_a$, $R^1_b$, $R^2_a$, $R^2_b$, $R^3_a$, $R^3_b$, $R^4_a$, $R^4_b$, $R^5$, and R" are the same as above. $X^7$ represents a leaving group such as halogen and sulfonyloxy.)

The compound (17), which is a compound of the present invention, can also be produced by coupling the compound (19) and the compound represented by the formula (20) by the general method as shown in the below reaction formula (VII).

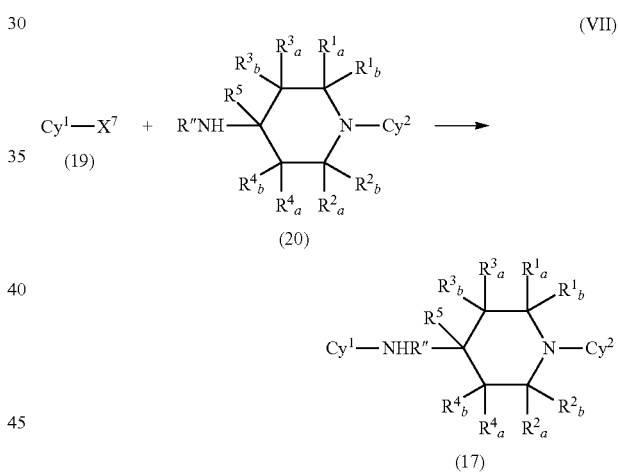

(In the formula, $Cy^1$, $Cy^2$, $X^7$, $R^1_a$, $R^1_b$, $R^2_a$, $R^2_b$, $R^3_a$, $R^3_b$, $R^4_a$, $R^4_b$, $R^5$, and R" are the same as above.)

3) Agents for Pest Control Represented by Formula (3)

The agents for pest control of the present invention are characterized by having the compounds represented by the formula (3), salts thereof or N-oxides thereof, as active ingredient.

The present invention relates to agents for pest control which contain the compounds represented by the formula (3), salts thereof or N-oxides thereof, as active ingredients.

In the formula (3), $Cy^{11}$, $Cy^{21}$, $X^{11}$, and $R^{11}_a$ to $R^{51}$ are the same as corresponding $Cy^1$, $Cy^2$, X, and $R^1_a$ to $R^5$ in the formula (1), respectively, except that there is no proviso regarding $Cy^{11}$ and $Cy^{21}$.

Since the compounds of the present invention (the compounds represented by the formula (1), salts thereof, or N-oxides thereof) have adulticidal, nymphicidal, larvicidal, or ovicidal activities, they can be used for controlling crop-damaging insect, acarid, sanitary insects, stored grain pest insects, clothes pests, household pests, or the like. Specific organisms to be the target of control include the following.

Preferably, pests which belong to the order of Lepidoptera such as *Spodoptera litura, Mamestra brassicae, Agrotis ipsilon*, green caterpillars, *Autographa nigrisigna, Plutella xylostella, Adoxophyes honmai, Homona magnanima, Carposina sasakii, Grapholita molesta, Phyllocnistis citrella, Caloptilia theivora, Phyllonorycter ringoniella, Lymantria dispar, Euproctis pseudoconspersa, Chilo suppressalis, Cnaphalocrocis medinalis, Ostrinia nubilasis, Hyphantria cunea, Cadra cautella*, genus *Heliothis*, genus *Helicoverpa*, genus *Agrothis, Tinea translucens, Cydia pomonella*, and *Pectinophora gossypiella*;

pests which belong to the order of Hemiptera such as *Myzus persicae, Aphis gossypii, Lipaphis erysimi, Rhopalosiphum padi, Riptortus clavatus, Nezara antennata, Unaspis yanonensis, Pseudococcus comstocki, Trialeurodes vaporariorum, Bemisia tabaci, Bemisia argentifolii, Psylla pyrisuga, Stephanitis nashi, Nilaparuata lugens, Laodelphax stratella, Sogatella furcifera*, and *Nephotettix cincticeps*;

pests which belong to the order of Coleoptera such as *Phyllotreta striolata, Aulacophora femoralis, Leptinotarsa decemlineata, Lissorhoptrus oryzophilus, Sitophilis zeamais, Callosobruchus chinensis, Popillia japonica, Anomala rufocuprea*, genus *Diabrotica, Lasioderma serricorne, Lyctus brunneus, Monochamus alternatus, Anoplophora malasiaca*, genus *Agriotis, Epilachna vigintioctopunctata, Tenebroides mauritanicus*, and *Anthonomus grandis*;

pests which belong to the order of Diptera such as *Musca domestica, Calliphora lata, Boettcherisca peregrine, Zeugodacus cucurbitae, Bactrocera dorsalis, Delia platura, Agromyza wyzae, Drosophila melanogaster, Stomoxys calcitrans, Culex tritaeniorhynchus, Aedes aegypti*, and *Anopheles sinensis*;

pests which belong to the order of Thysanoptera such as *Thrips palmi* and *Scirtothrips dorsalis*;

pests which belong to the order of Hymenoptera such as *Monomorium pharaonis, Vespa simillima xanthoptera*, and *Athalia rosae ruficornis*;

pests which belong to the order of Orthoptera such as *Locusta migratoria, Blattella germanica, Periplaneta americana*, and *Periplaneta fuliginosa*;

pests which belong to the order of Isoptera such as *Coptotermes formosanus* and *Reticulitermes speratus speratus*;

pests which belong to the order of Siphonaptera such as *Pulex irritans* and *Ctenocephalides felis felis*;

pests which belong to the order of Phthiraptera such as *Pediculus humanus*; Acarina such as *Tetranychus urticae, Tetranychus cinnabarinus, Tetranychus kanzawai, Panonychus citri, Panonychus ulmi, Aculops pelekassi, Aculus schlechtendali, Polyphagotarsonemus latus*, genus *Brevipalpus*, genus *Eotetranichus, Rhizoglyphus robini, Tyrophagus putrescentiae, Dermatophagoides farinae, Boophilus microplus*, and *Haemaphysalis longicornis*; and plant parasitic nematodes such as *Meloidogyne incognita, Pratylenchus* spp., *Heterodera glycines, Aphelenchoides besseyi*, and *Bursaphelenchus xylophilus*.

Pests to which the present invention is preferably applied are pests which belong to the order of Lepidoptera, pests which belong to the order of Hemiptera, Acarina, pests which belong to the order of Thysanoptera, and pests which belong to the order of Coleoptera, and particularly preferably Acarina.

Moreover, drugs which are also effective for pests or Acarnia that are of resistant lineage are desired because in recent years, resistance to organophosphorus pesticides, carbamate pesticides, or acaricides developed among many pests such as *Plutella xylostella, Delphacidae, Deltocephalidae*, and *Aphididae* has caused problems because of insufficient effects of these drugs. The compounds of the present invention are drugs having excellent insecticidal and acaricidal effects not only on those of sensitive lineages but also on pests of lineages resistant to organophosphorus pesticides, carbamate pesticides, and pyrethroid pesticides, and on Acarnia of lineages resistant to acaricides.

Additionally, the compounds of the present invention are drugs that show less herbicide injuries, have lower toxicity to fish and warm-blooded animals, and higher safety.

The compounds of the present invention can also be used as an antifoulant to prevent aquatic organisms attaching to objects which contact water such as ship bottoms (or hulls, alternatively) and fishing nets.

Some of the compounds of the present invention exhibit germicidal activities, herbicidal activities, or plant-growth regulating activities. Moreover, some intermediates of the compounds of the present invention, which are represented by the formula (1) or (3), exhibit insecticidal/acaricidal activities.

The agents for pest control of the present invention have the compounds of the present invention, which are represented by the formula (1) or (3), as active ingredients and the agents can be used either singularly or by mixing two or more thereof. The compounds of the present invention can be used as they are without adding any other components. However, when used practically, they are normally further mixed with solid, liquid, or gaseous carriers, or are impregnated in substrates such as porous ceramic plates and nonwoven fabrics, and by adding surfactants and/or other adjuvants where necessary, used as formulations in the form which general agrochemicals may adopt, that is, wettable powder, granule, dusting powder, emulsion, water-soluble powder, suspending agent, granulated wettable powder, floable, aerosol, transpiration agent by heating, fumigant, poison bait, microcapsule, or the like.

As additives and carriers, vegetable powders such as soy flour and wheat flour; fine mineral powder such as diatomaceous earth, apatite, gypsum, talc, bentonite, pyrophyllite, and clay; and organic and inorganic compounds such as sodium benzoate, urea, and sodium sulfate are used when solid formulation is required. When liquid form of formulation is required, petroleum fractions such as kerosene, xylene, and solvent naphtha, and cyclohexane, cyclohexanone, dimethylformamide, dimethyl sulfoxide, alcohol, acetone, methyl isobutyl ketone, mineral oil, vegetable oil, water, or the like are used as a solvent. As gaseous carriers used in propellant, butane (gas), LPG, dimethyl ether, and carbon dioxide gas can be used.

As a substrate of poison bait, bait components such as grain powder, vegetable oil, sugar, and crystalline cellulose; antioxidants such as dibutylhydroxytoluene and nordihydroguaiaretic acid; preservatives such as dehydroacetic acid; agents for preventing accidental ingestion by children or pets such as *capsicum* powder; and pest-insect attracting scents such as cheese scents and onion scents can be used.

Additionally, in order to achieve homogenous and stable forms in these formulations, it is also possible to add surfactants if necessary. Although surfactants are not particularly limited, examples thereof include, for instance, nonionic surfactants such as alkyl ether where polyoxyethylene is added, higher fatty acid ester where polyoxyethylene is added, sorbitan higher fatty acid ester where polyoxyethylene is added, and tristyryl phenyl ether where polyoxyethylene is added; sulfate ester salt of alkyl phenyl ether where polyoxyethylene is added, alkyl naphthalene sulfonate salt, polycarboxylate salt, lignin sulfonate salt, formaldehyde condensate of alkyl naphthalene sulfonate, and isobutylene-maleic anhydride copolymer.

When the compounds of the present invention are used as agents for pest control in agriculture, the amount of active ingredient in the formulation is 0.01 to 90 weight % and particularly preferably 0.05 to 85 weight % and wettable powder, emulsion, suspending agents, floable agents, water-soluble powder, granulated wettable powder which are diluted to predetermined concentrations with water, and dusting powder and granules as they are, can be applied onto plants or soil.

In addition, when the compounds of the present invention are used as agents for pest control in quarantine purposes, emulsion, wettable powder, floable agents, and the like are applied by diluting to predetermined concentrations with water and oil solution, and aerosol, poison bait, anti-acarid sheet, and the like can be applied as they are.

When the compounds of the present invention are used as agents for pest control in controlling ectoparasites of livestock such as cattle and pigs or of pets such as dogs and cats, formulations using the compounds of the present invention are used in known methods in the field of veterinary medicine. As such methods, examples thereof include a method for administering in forms such as tablets, capsules, immersion liquid, feedstuff mix, suppository, and injection (intramuscular, subcutaneous, intravenous, intraperitoneal, or the like) when systemic control is required and a method for administering by spraying, pouring-on, or spotting-on oily- or aqueous liquid formulations or a method for mounting objects, which are resin formulations shaped into collars, ear tags, or the like, when non-systemic control is required. In this case, the proportion can be normally used where 0.01 to 1000 mg of the compounds of the present invention are applied per 1 kg of host animal.

It should be noted that although the compounds of the present invention are, needless to say, sufficiently effective even when used solely, they can also be used by mixing or combining with one or more of other agents for pest control, germicides, insecticides/acaricides, herbicides, plant growth regulators, synergists, fertilizers, soil conditioners, animal feed, or the like.

Representative examples of active ingredients of germicides, acaricides, plant growth regulators, or the like which can be used by mixing or combining with the compounds of the present invention are shown below.

Germicides:

captan, folpet, thiuram, ziram, zineb, maneb, mancozeb, propineb, polycarbamate, chlorothalonin, quintozene, captafol, iprodione, procymidone, fluoroimide, mepronil, flutolanil, pencycuron, oxycarboxin, fosetyl-aluminum, propamocarb, triadimefon, triadimenol, propiconazole, diclobutrazol, bitertanol, hexaconazole, myclobutanil, flusilazole, etaconazole, fluotrimazole, flutriafen, penconazole, diniconazole, cyproconazole, fenarimol, triflumizole, prochloraz, imazalil, pefurazoate, tridemorph, fenpropimorph, triforine, buthiobate, pyrifenox, anirazine, polyoxins, metalaxyl, oxadixyl, furalaxyl, isoprothiolane, probenazole, pyrrolnitrin, blasticidin S, kasugamycin, validamycin, dihydrostreptomycin sulfate, benomyl, carbendazim, thiophanate-methyl, hymexazol, basic copper chloride, basic copper sulfate, fentinacetate, triphenyltin hydroxide, diethofencarb, chinomethionat, binapacryl, lecithin, baking soda, dithianon, dinocap, fenaminosulf, diclomezine, guazatine, dodine, IBP, edifenphos, mepanipyrim, fermzone, trichlamide, methasulfocarb, fluazinam, ethoquinolac, dimethomorph, pyroquilon, tecloftalam, phthalide, phenazine oxide, thiabendazole, tricyclazole, vinclozolin, cymoxanil, cyclobutanil, guazatine, propamocarb hydrochloride, oxolinic acid, cyflufenamid, iminoctadine, kresoxim-methyl, triazine, fenhexamid, cyazofamid, cyprodinil, prothioconazole, fenbuconazole, trifloxystrobin, azoxystrobin, hexaconazole, imibenconazole, tebuconazole, difenoconazole, and carpropamid;

Insecticides/acaricides:

organophosphorus and carbamate pesticides:

fenthion, fenitrothion, diazinon, chlorpyrifos, ESP, vamidothion, phenthoate, dimethoate, formothion, malathion, trichlorphon, thiometon, phosmet, dichlorvos, acephate, EPBP, methyl parathion, oxydemeton methyl, ethion, salithion, cyanophos, isoxathion, pyridafenthion, phosalone, methidathion, sulprofos, chlorfenvinphos, tetrachlorvinphos, dimethylvinphos, propaphos, isofenphos, ethylthiometon, profenofos, pyraclofos, monocrotophos, azinphos-methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, fenoxycarb, cartap, thiocyclam, bensultap, and the like; pyrethroid pesticides:

permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, etofenprox, cyclopro-thrin, tralomethrin, silafluofen, and acrinathrin;

benzoylurea and other pesticides:

diflubenzuron, chlorfluazuron, hexaflumuron, triflumuron, flufenoxuron, flucycloxuron, buprofezin, pyriproxyfen, methoprene, benzoepin, diafenthiuron, imidacloprid, fipronil, nicotine sulfate, rotenone, metaldehyde, acetamiprid, chlorfenapyr, nitenpyram, thiacloprid, clothianidin, thiamethoxam, dinotefuran, indoxacarb, pymetrozine, spinosad, emamectin, pyridalyl, tebufenozide, chromafenozide, methoxyfenozide, tolfenpyrad, machine oil, microbial pesticides such as BT and entomopathogenic viruses;

nematicides:

fenamiphos, fosthiazate, cadusafos, and the like;

acaricides:

chlorobenzilate, phenisobromolate, dicofol, amitraz, BPPS, benzomate, hexythiazox, fenbutatin oxide, polynactin, chinomethionat, CPCBS, tetradifon, avermectin, milbemectin, clofentezine, cyhexatin, pyridaben, fenpyroximate, tebufenpyrad, pyrimidifen, fenothiocarb, dienochlor, fluacrypyrim, acequinocyl, bifenazate, etoxazole, spirodiclofen, fenazaquin, and the like;

plant growth regulators:

gibberellins (for example, gibberellin A3, gibberellin A4, or gibberellin A7), IAA, NAA.

EXAMPLE

Next, the present invention will be described in further detail by using Examples. However, the present invention is not limited to the Examples below in any aspects.

Production Example 1

Example 1

Production of 3α-(5-trifluoromethyl-2-pyridyloxy)-8-(5-trifluoromethyl-pyridin-2-yl)-8-azabicyclo[3.2.1]octane

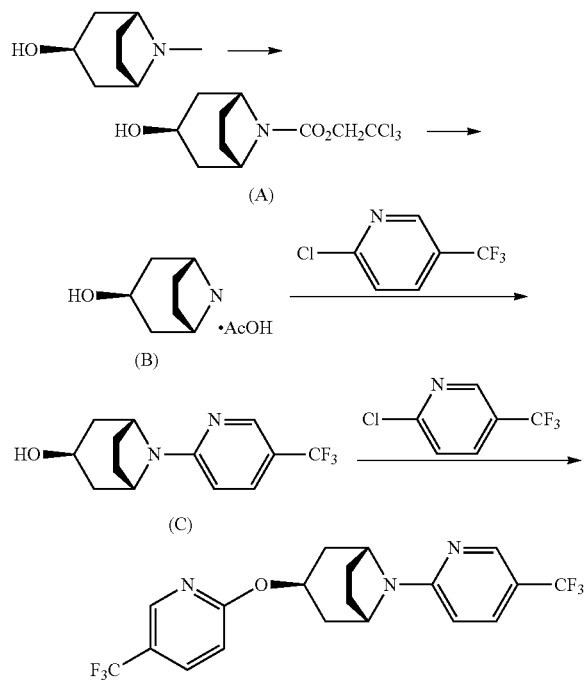

23.3 g of 2,2,2-trichloroethyl chloroformate ester was added to 150 ml of the benzene suspension containing 14.1 g of tropine and 1.4 g of potassium carbonate at room temperature and the entire mixture was refluxed for 3.5 hours. After being cooled to room temperature, the reaction mixture was poured into water and extracted with ethyl acetate. The organic layer was washed with saline and dried with anhydrous magnesium sulfate. 30.1 g of an oily carbonate (A) was obtained by evaporating the solvents under reduced pressure and this carbonate was used directly in the next reaction.

Next, 65 g of zinc powder was added to 250 ml of the acetate solution of this carbonate (A). After being stirred for 5 minutes, the mixture was heated at 80° C. for 1 hour. After being cooled to room temperature, the mixture was subjected to celite filtration. 15.5 g of a crude product of the compound (B) was obtained by vacuum-concentrating the filtrate.

150 ml of acetonitrile suspension containing 5.64 g of the crude product of the compound (B) obtained as above, 41.5 g of potassium carbonate, and 8.2 g of 2-chloro-5-trifluoromethylpyridine was refluxed for 3.5 hours. After being cooled to room temperature, the reaction mixture was poured into water and extracted with ethyl acetate. The organic layer was washed with saline and dried with anhydrous magnesium sulfate. 3.5 g of the compound (C) was obtained as crystals by evaporating the solvents under reduced pressure.

32 mg of 60% sodium hydride was added to 3 ml of dimethylformamide (DMF) solution containing 0.21 g of the compound (C) with ice-cooling and the entire mixture was stirred for 40 minutes. Subsequently, 0.17 g of 2-chloro-5-trifluoromethylpyridine was added to this mixture and the resulting mixture was heated to 100° C. and was stirred overnight with heating. After cooling to room temperature, the reaction mixture was poured into ice-cold water and extracted with ethyl acetate. After being washed with water and dried with anhydrous magnesium sulfate, the organic layer was filtered and then vacuum-concentrated. The residue was purified by column chromatography (developing solution: mixed solvent of n-hexane and ethyl acetate) to obtain 0.06 g of the target compound. Melting temperature: 104-105° C.

$^1$H-NMR(CDCl$_3$, δppm): 1.25(s, 1H), 1.55(s, 1H), 1.95-2.33(m, 6H), 4.58(brs, 2H), 5.37(t, 1H), 6.55(d, 1H), 6.80(d, 1H), 7.61(dd, 1H), 7.78(dd, 1H), 8.41(s, 2H)

Example 2

Production of 3α-[2-n-propoxy-4-(trifluoromethyl)phenoxy]-8-[3-fluoro-4-(trifluoromethyl)phenyl]-8-azabicyclo[3.2.1]octane

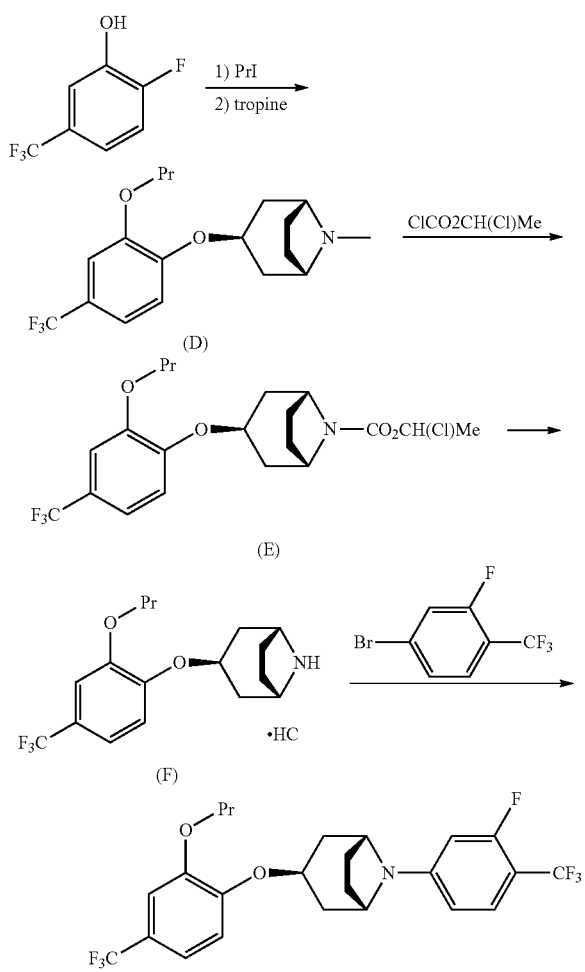

0.44 g of 60% sodium hydride was added to 15 ml of DMF solution containing 1.8 g of 4-fluoro-3-hydroxybenzotrifluoride and after stirring the entire mixture for 20 minutes, 3 ml of DMF solution containing 1.7 g of 1-iodopropane was added thereto and the resulting solution was further stirred for 4 hours at room temperature. 1.4 g of tropine and 0.43 g of 60% sodium hydride were added to the obtained mixture at room temperature and the resulting solution was heated to 100° C. and was stirred overnight with heating. After cooling to room temperature, the reaction mixture was poured into ice-cold water and extracted with ethyl acetate. After being washed with water and dried with anhydrous magnesium sulfate, the organic layer was filtered and then vacuum-concentrated. The residue was purified by column chromatography to obtain 1.1 g of an oily compound (D).

4 ml of methylene chloride solution containing 0.83 g of 1-chloroethyl chloroformate ester was added to 6 ml of methylene chloride solution containing 1.0 g of the compound (D) at room temperature and the entire mixture was refluxed overnight. The reaction mixture was diluted with methylene chloride, washed with saturated sodium bicarbonate water and then with saline, and dried with anhydrous magnesium sulfate. A crude carbonate (E) was obtained by evaporating the solvents under reduced pressure and was used directly in the next reaction.

6 ml of methanol was added to the compound (E) and the mixture was refluxed for 2.5 hours. The resulting mixture was vacuum-concentrated to obtain a crude compound (F). The crude compound (F) was alkali-treated to obtain a free amine and this amine was used directly in the next reaction.

0.4 g of t-butoxysodium, 13.7 mg of Pd$_2$(dba)$_3$, and 17.7 mg of 2-(dicyclohexylphosphino)-2'-(N,N-dimethylamino) biphenyl were added to 11 ml of toluene solution containing 1 g of the free form of the compound (F) obtained above and 0.73 g of 4-bromo-2-fluorobenzotrifluoride and the entire mixture was refluxed overnight under nitrogen atmosphere. After cooling to room temperature, the reaction mixture was poured into water and extracted with ethyl acetate. After being washed with water and dried with anhydrous magnesium sulfate, the organic layer was filtered and then vacuum-concentrated. The residue was purified by column chromatography (developing solution: mixed solvent of n-hexane and ethyl acetate) to obtain 0.54 g of the target compound. Viscous oil $^1$H-NMR(CDCl$_3$, δppm): 1.08(t, 3H), 1.81-1.97(m, 4H), 2.04-2.23(m, 4H), 2.45(q, 2H), 3.97(t, 2H), 4.19(brs, 2H), 4.57(brt, 1H), 6.44-6.51(m, 2H), 6.76(d, 1H), 7.13(s, 1H); 7.16(d, 1H), 7.38(t, 1H)

Example 3

Production of 3α-[5-(trifluoromethyl)-2-pyridyloxy]-8-(2-formyl-4-(trifluoromethyl)phenyl)-8-azabicyclo[3.2.1]octane

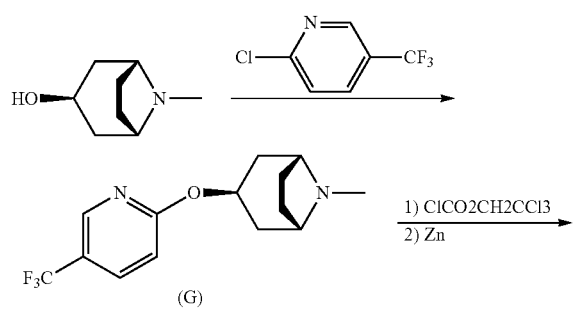

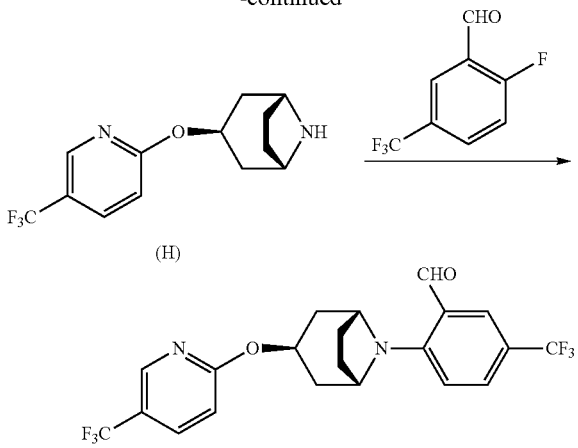

A total of 5.8 g of 60% sodium hydride was added at multiple steps to 240 ml of DMF solution containing 17.6 g of tropine and 21.6 g of 2-chloro-5-trifluoromethylpyridine at 80° C. and the entire mixture was stirred for 2 hours at the same temperature. After cooling to room temperature, the reaction mixture was poured into ice-cold water and extracted with ethyl acetate. After being washed with water and dried with anhydrous magnesium sulfate, the organic layer was filtered and then vacuum-concentrated. The residue was purified by column chromatography (NH-gel; DM-1020 was used; developing solution: mixed solvent of n-hexane and ethyl acetate) to obtain 25 g of the compound (G).

26 g of 2,2,2-trichloroethyl chloroformate ester was added to 150 ml of the benzene suspension containing 25 g of the compound (G) and 1.33 g of potassium carbonate at room temperature and the mixture was refluxed for 1 hour with heating. After being cooled to room temperature, the mixture was poured into water and extracted with ethyl acetate. The organic layer was washed with saline and dried with anhydrous magnesium sulfate. A solid carbonate was obtained by evaporating the solvents under reduced pressure and this carbonate was used directly in the next reaction.

42 g of zinc powder was added to 300 ml of the acetate solution containing the carbonate obtained above and the entire mixture was stirred for 1 hour with heating at 100° C. After being cooled to room temperature, the mixture was subjected to celite filtration and after adding chloroform and water to the resulting filtrate, the organic layer was separated. The aqueous layer was made weakly alkaline, extracted with chloroform, and mixed with the separated organic layer. The mixture was washed with water, dried with anhydrous magnesium sulfate, and then the solvents thereof were evaporated under reduced pressure to obtain 14.4 g of a crude compound (H).

30 ml of acetonitrile suspension containing 2 g of the compound (H), 3.04 g of potassium carbonate, and 1.41 g of 2-fluoro-5-trifluoromethylbenzaldehyde was refluxed for 3.5 hours. After being cooled to room temperature, the reaction mixture was poured into water and extracted with ethyl acetate. The organic layer was washed with saline and dried with anhydrous magnesium sulfate. 2.77 g of the target compound was obtained by evaporating the solvents under reduced pressure and purifying the residue with silica gel column chromatography (developing solution: mixed solvent of n-hexane and ethyl acetate). Melting temperature: 122-123° C.

$^1$H-NMR(CDCl$_3$, δppm): 1.99-2.05(m, 2H), 2.12(s, 1H), 2.17(s, 1H), 2.21-2.28(m, 2H), 2.41(t, 1H), 2.45(t, 1H), 4.04 (brs, 2H), 5.50(t, 1H), 6.79(d, 1H), 7.05(d, 1H), 7.61(d, 1H), 7.79(dd, 1H), 8.02(s, 1H), 8.44(s, 1H), 10.19(s, 1H)

Example 4

Production of 3α-[2-isopropoxycarbonyl-4-(trifluoromethyl)phenoxy]-8-[6-cyano-pyridazine-3-yl]-8-azabicyclo[3.2.1]octane

Step 1

Production of 3α-[2-isopropoxycarbonyl-4-(trifluoromethyl)phenoxy]-8-azabicyclo[3.2.1]octane (J)

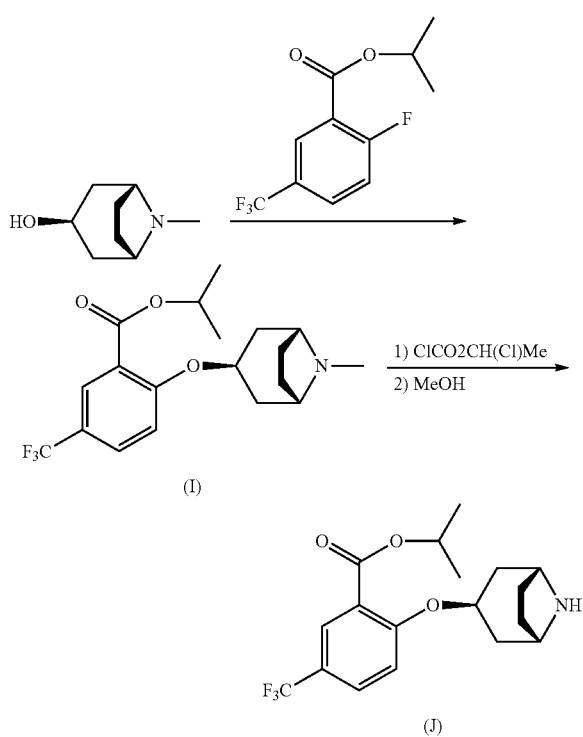

0.56 g of 60% sodium hydride was added to 20 ml of DMF solution containing 1.0 g of tropine. 1.76 g of 4-fluoro-3-isopropoxycarbonylbenzotrifluoride was added dropwise to this mixture. After being stirred overnight at room temperature, the mixture was poured into water and extracted with ethyl acetate. After being washed with water and dried with anhydrous magnesium sulfate, the organic layer was filtered and the resulting filtrate was evaporated under reduced pressure to obtain 1.15 g of a crude compound (I). The crude compound (I) was directly used in the next reaction. Note that 4-fluoro-3-isopropoxycarbonylbenzotrifluoride was obtained by isopropyl-esterifying the commercially available 2-fluoro-5-trifluoromethylbenzoate.

0.05 g of potassium carbonate and 0.52 g of 1-chloroethyl chloroformate ester were added to 20 ml of benzene solution containing 1.23 g of the crude compound (I) and the mixture was refluxed for 5 hours with heating. After being cooled to room temperature, the mixture was poured into water and extracted with ethyl acetate. The organic layer was washed with saline and dried with anhydrous magnesium sulfate. The concentrate obtained by evaporating the solvents under reduced pressure was dissolved in 20 ml of methanol and the entire solution was stirred overnight at room temperature. 1.0 g of a crude compound (J) was obtained by evaporating the solvents under reduced pressure and this compound was used directly in the next reaction.

Step 2

Production of 3α-[2-isopropoxycarbonyl-4-(trifluoromethyl)phenoxy]-8-[6-cyano-pyridazin-3-yl]-8-azabicyclo[3.2.1]octane

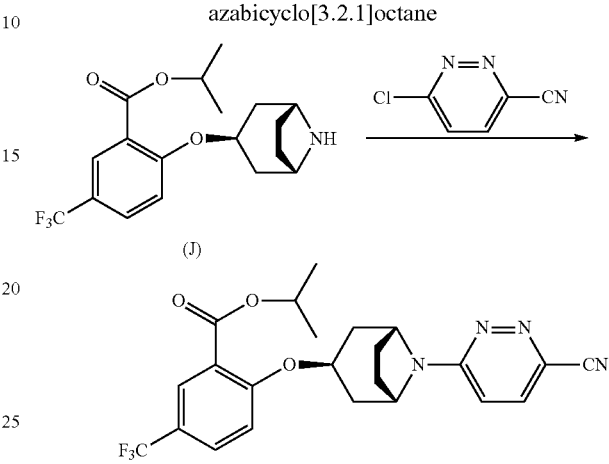

30 ml of acetonitrile suspension containing 1.0 g of the crude compound (J), 1.16 g of potassium carbonate, and 0.39 g of 3-chloro-6-cyanopyridazine was refluxed for 3 hours with heating. After being cooled to room temperature, the mixture was poured into water and extracted with ethyl acetate. The organic layer was washed with saline and dried with anhydrous magnesium sulfate. The concentrate obtained by evaporating the solvents under reduced pressure was purified with silica gel column chromatography (eluant: mixed solvent of n-hexane and ethyl acetate) to obtain 0.18 g of crystals. Furthermore, these crystals were washed with diethylether to obtain 0.04 g of the target compound. Melting temperature: 219-221° C.

$^1$H-NMR(CDCl$_3$, δppm): 1.39(d, 6H), 2.03-2.37(m, 6H), 2.48-2.51(m, 2H), 4.69(brs, 3H), 5.22-5.30(m, 1H), 6.75(d, 1H), 6.85(d, 1H), 7.44(d, 1H), 7.68(d, 1H), 7.98(s, 1H).

Example 5

Production of 8β-[2-propoxy-4-(trifluoromethyl)phenoxy]-3-[6-(trifluoromethyl)-pyridin-3-yl]-3-azabicyclo[3.2.1]octane

Step 1

Production of N-benzyl-8β-[2-propoxy-4-(trifluoromethyl)phenoxy]-3-azabicyclo[3.2.1]octane (L)

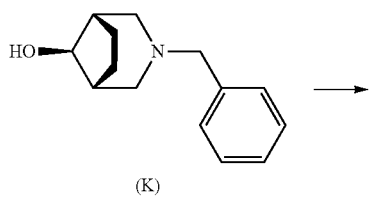

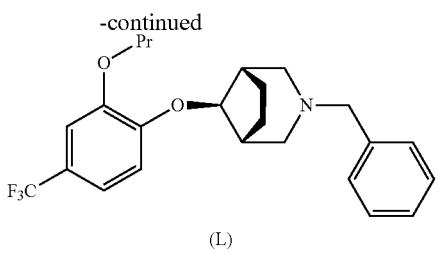

(L)

0.12 g of 60% sodium hydride was added to 4 ml of DMF solution containing 0.50 g of 4-fluoro-3-hydroxybenzotrifluoride with ice-cooling. After stirring the mixture at room temperature for 30 minutes, 0.51 g of 1-iodopropane was added thereto. The mixture was heated to 90° C. and the mixture was stirred for 30 minutes. 4 ml of DMF solution containing 0.41 g of the compound (K) and 0.09 g of 60% sodium hydride were added to the mixture at room temperature and after being stirred for 15 minutes, the resulting mixture was heated to 100° C. and stirred for 2 hours. After being cooled to room temperature, the mixture was poured into water and extracted with ethyl acetate. After being washed with water and dried with anhydrous magnesium sulfate, the organic layer was filtered and then vacuum-concentrated. The concentrate was purified by silica gel column chromatography (eluant: mixed solvent of n-hexane and ethyl acetate) to obtain 0.75 g of the compound (L) as an oily matter.

$^1$H-NMR(CDCl$_3$, δppm): 1.05(t, 3H), 1.75-1.91(m, 6H), 2.19(d, 2H), 2.34(brs, 2H), 2.74(d, 2H), 3.51(s, 2H), 3.96(t, 2H), 4.33(s, 1H), 6.94(d, 1H), 7.07(s, 1H), 7.13(d, 1H), 7.20-7.34(m, 5H)

Step 2

Production of 8β-[2-propoxy-4-(trifluoromethyl)phenoxy]-3-[6-(trifluoromethyl)-pyridin-3-yl]-3-azabicyclo[3.2.1]octane

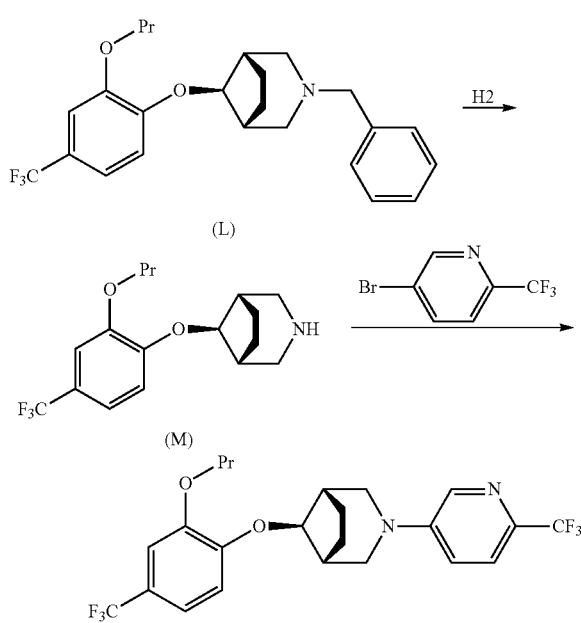

0.13 g of 10% palladium-carbon was added to 20 ml of the ethanol solution containing 0.66 g of the compound (L). The suspension was stirred overnight at room temperature under hydrogen atmosphere (1.01×10$^5$ Pa). The reaction solution was subjected to celite filtration and the resulting filtrate was evaporated under reduced pressure to obtain 0.55 g of a crude compound (M).

3-bromo-6-(trifluoromethyl)pyridine was derived from the commercially available 3-amino-6-(trifluoromethyl)pyridine by the usual Sandmeyer reaction.

0.16 g of 3-bromo-6-(trifluoromethyl)pyridine, 0.1 g of t-butoxy sodium, 6.47 mg of Pd$_2$(dba)$_3$, and 8.34 mg of 2-(dicyclohexylphosphino)-2'-(N,N-dimethylamino)biphenyl were added to 2 ml of the toluene solution containing 0.23 g of the crude compound (M) and the mixture was refluxed with heating overnight under nitrogen atmosphere. After cooling, the reaction mixture was poured into water and extracted with ethyl acetate. After being washed with water and dried with anhydrous magnesium sulfate, the organic layer was filtered and then vacuum-concentrated. The concentrate was purified by silica gel column chromatography (eluant: mixed solvent of n-hexane and ethyl acetate) to obtain 0.1 g of the target compound. Melting temperature: 79-80° C.

$^1$H-NMR(CDCl$_3$, δppm): 1.07(t, 3H), 1.67-1.71(m, 2H), 1.80-1.92(m, 2H), 2.09-2.12(m, 2H), 2.62(brs, 2H), 3.07(d, 2H), 3.69(dd, 2H), 3.98(t, 2H), 4.60(s, 1H), 7.01(d, 1H), 7.09-7.19(m, 3H), 7.50(d, 1H), 8.28(d, 1H)

Example 6

Production of 8β-[2-isopropylideneaminooxy-4-(trifluoromethyl)phenoxy]-3-(5-trifluoromethyl-1,3,4-thiadiazol-2-yl)-3-azabicyclo[3.2.1]octane Step 1

Production of 3-(5-trifluoromethyl-1,3,4-thiadiazol-2-yl)-3-azabicyclo[3.2.1]octan-8β-ol

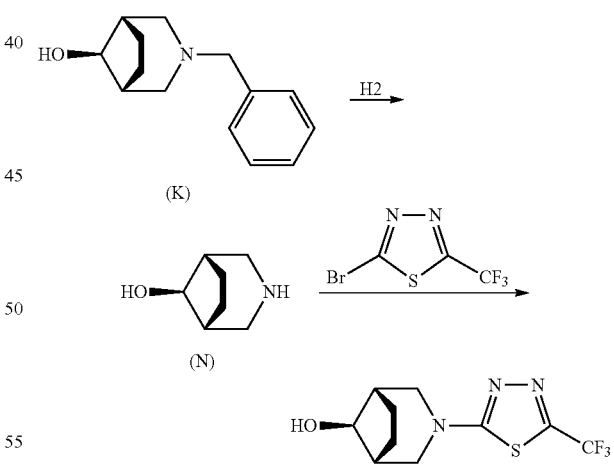

2.6 g of 10% palladium-carbon was added to 100 ml of the ethanol solution containing 4.32 g of the compound (K). The suspension was heated to 50° C. and stirred for 2 hours under hydrogen atmosphere and further stirred overnight at room temperature. The reaction solution was subjected to celite filtration and the resulting filtrate was evaporated under reduced pressure to obtain 2.5 g of the crude compound (N).

2-bromo-5-(trifluoromethyl)thiadiazole was derived from the commercially available 2-amino-5-(trifluoromethyl)thiadiazole by the usual Sandmeyer reaction.

0.37 g of 2-bromo-5-(trifluoromethyl)-1,3,4-thiadiazole, 0.65 g of potassium carbonate, and 10 mg of tetra-n-butylammoniumbromide were added to 6 ml of the acetonitrile solution containing 0.2 g of the crude compound (N) and the mixture was refluxed with heating overnight. After being cooled to room temperature, the mixture was poured into water and extracted with ethyl acetate. After being washed with water and dried with anhydrous magnesium sulfate, the organic layer was filtered and then vacuum-concentrated. The concentrate was purified by silica gel column chromatography (eluant: mixed solvent of n-hexane and ethyl acetate) to obtain 0.25 g of the target compound.

Step 2

Production of 8β-[2-hydroxy-4-(trifluoromethyl) phenoxy]-3-(5-trifluoromethyl-1,3,4-thiadiazol-2-yl)-3-azabicyclo[3.2.1]octane (Q)

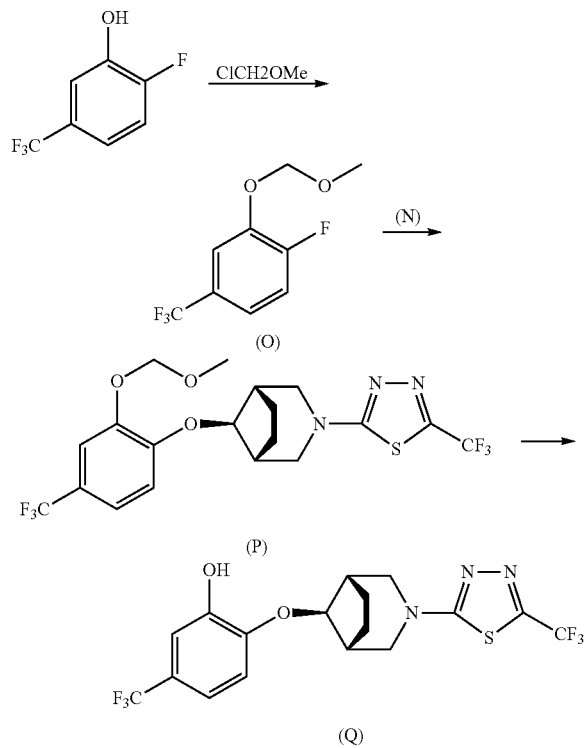

1.6 g of 60% sodium hydride was added to 60 ml of the DMF solution containing 6.0 g of 4-fluoro-3-hydroxybenzotrifluoride with ice-cooling. After stirring the mixture for 30 minutes at room temperature, 3.2 g of chloromethyl ether was added dropwise with ice-cooling. After reaching room temperature, the resulting mixture was stirred for 30 minutes, poured into water, and extracted with ethyl acetate. After being washed with water and dried with anhydrous magnesium sulfate, the organic layer was filtered and then vacuum-concentrated. The concentrate was purified by silica gel column chromatography (eluant: mixed solvent of n-hexane and ethyl acetate) to obtain 6.88 g of a compound (O).

0.34 g of the compound (N) was added to 6 ml of the DMF solution containing 0.36 g of the compound (O). The mixture was heated to 80° C. and 0.07 g of 60% sodium hydride was added thereto and the resulting mixture was kept heated to 80° C. for 2 hours. After being cooled to room temperature, the mixture was poured into water and extracted with ethyl acetate. After being washed with water and dried with anhydrous magnesium sulfate, the organic layer was filtered and then vacuum-concentrated. The concentrate was purified by silica gel column chromatography (eluant: mixed solvent of n-hexane and ethyl acetate) to obtain 0.28 g of a compound (P).

$^1$H-NMR(CDCl$_3$, δppm): 1.68-1.71(m, 2H), 2.10-2.13(m, 2H), 2.62(brs, 2H), 3.45(d 2H), 3.52(s, 3H), 3.84(d, 2H), 4.63(s, 1H), 5.20(s, 2H), 7.01(d, 1H), 7.25(d, 1H), 7.37(s, 1H)

4 ml of 10% hydrochloric acid was added to 4 ml of tetrahydrofuran (THF) solution containing 0.28 g of the compound (P) at room temperature. The mixture was refluxed with heating for 1 hour and then poured into water and extracted with ethyl acetate. The organic layer was washed with saturated sodium bicarbonate water and then with saline, and dried with anhydrous magnesium sulfate. 0.25 g of the target compound (Q) was obtained by evaporating the solvents under reduced pressure.

$^1$H-NMR(CDCl$_3$, δppm): 1.68-1.79(m, 2H), 2.05-2.10(m, 2H), 2.69(brs, 2H), 3.50(d, 2H), 3.89(d, 2H), 4.67(s, 1H), 5.58(s, 1H), 6.97(d, 1H), 7.15(d, 1H), 7.21(s, 1H)

Step 3

Production of 8β-[2-isopropylideneaminooxy-4-(trifluoromethyl)phenoxy]-3-(5-trifluoromethyl-1,3,4-thiadiazol-3-yl)-3-azabicyclo[3.2.1]octane

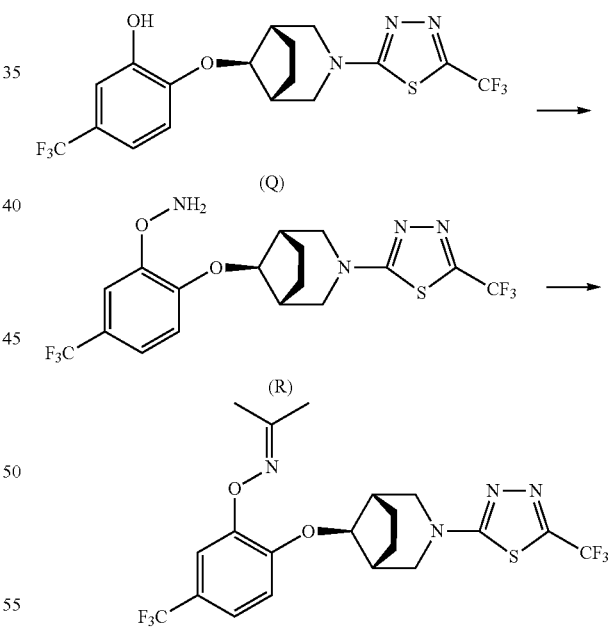

0.07 g of a compound (R) was synthesized by the method described in Japanese Patent Application Laid-Open No. 2001-81071 using 0.25 g of the compound (Q).

0.5 ml of acetone and 1 drop of concentrated hydrochloric acid were added to 1 nil of ethanol solution containing 0.07 g of the compound (R) and the entire mixture was stirred for 80 minutes at room temperature. The reaction mixture was poured into water and extracted with ethyl acetate. After being washed with water and dried with anhydrous magnesium sulfate, the organic layer was filtered and then vacuum-concentrated. The concentrate was purified by silica gel column chromatography (eluant: mixed solvent of n-hexane and ethyl acetate) to obtain 0.05 g of the target compound. Melting temperature: 113-115° C.

$^1$H-NMR(CDCl$_3$, δppm): δ1.64-1.70(m, 2H), 2.06(d, 6H), 2.03-2.13(m, 2H), 2.61(brs, 2H), 3.42(d, 2H), 3.82(dd, 2H), 4.64(s, 1H), 7.01(d, 1H), 7.21(d, 1H), 7.70(s, 1H)

Example 7

Production of 8β-[2-isopropylideneaminooxy-4-(trifluoromethyl)phenoxy]-3-(5-cyano-pyridin-2-yl)-3-azabicyclo[3.2.1]octane (e)

Step 1

Production of 8β-hydroxy-3-(5-cyano-pyridin-2-yl)-3-azabicyclo[3.2.1]octane (S)

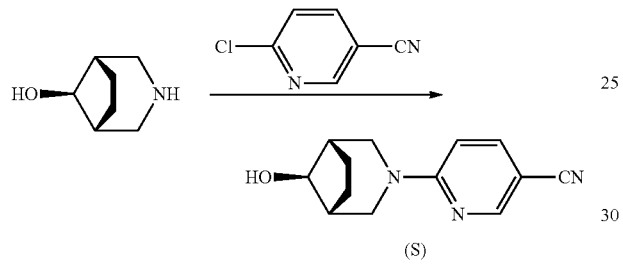

5 ml of acetonitrile suspension containing 0.15 g of 3-azabicyclo[3.2.1]octa-8-ol, 0.65 g of potassium carbonate, and 0.33 g of 2-chloro-5-cyanopyridine was refluxed with heating overnight. After being cooled to room temperature, the mixture was poured into water and extracted with ethyl acetate. The organic layer was washed with saline and dried with anhydrous magnesium sulfate. 0.16 g of a crude compound (S) was obtained by evaporating solvents under reduced pressure and this compound was directly used in the next step.

Step 2

Production of 8β-[2-methoxymethoxy-4-(trifluoromethyl)phenoxy]-3-(5-cyano-pyridin-2-yl)-3-azabicyclo[3.2.1]octane (T)

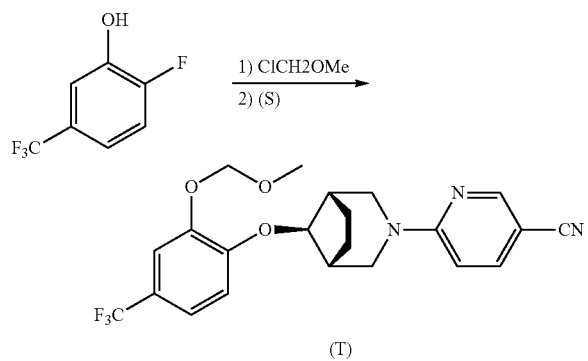

0.14 g of 60% sodium hydride was added to 10 ml of DMF solution containing 0.58 g of 4-fluoro-3-hydroxybenzotrifluoride with ice-cooling. After stirring the mixture for 30 minutes at room temperature, 0.28 g of chloromethyl ether was added dropwise thereto with ice-cooling. After completing the addition, the reaction solution was heated to room temperature and stirred for 30 minutes and then further heated to 80° C. and stirred for 30 minutes. 0.49 g of the compound (S) and 0.13 g of 60% sodium hydride were added to the reaction mixture at 80° C. and the resulting mixture was stirred for 30 minutes and then heated to 80° C. and was further stirred for 2 hours. The reaction mixture was cooled to room temperature, poured into water, and extracted with ethyl acetate. After being washed with water and dried with anhydrous magnesium sulfate, the organic layer was filtered and vacuum-concentrated. The concentrate was purified by silica gel column chromatography (eluant: mixed solvent of n-hexane and ethyl acetate) to obtain 0.82 g of the target compound (T).

$^1$H-NMR(CDCl$_3$, δppm): 1.55-1.63(m, 2H), 2.02-2.05(m, 2H), 2.60(brs, 2H), 3.13(d, 2H), 3.52(s, 3H), 4.22(d, 2H), 4.63(s, 1H), 5.20(s, 2H), 6.58(d, 1H), 7.03(d, 1H) 7.26(d, 1H), 7.37(s, 1H), 7.62(d, 1H), 8.41(s, 1H)

Step 3

Production of 8β-[2-hydroxy-4-(trifluoromethyl)phenoxy]-3-(5-cyano-pyridin-2-yl)-3-azabicyclo[3.2.1]octane (U)

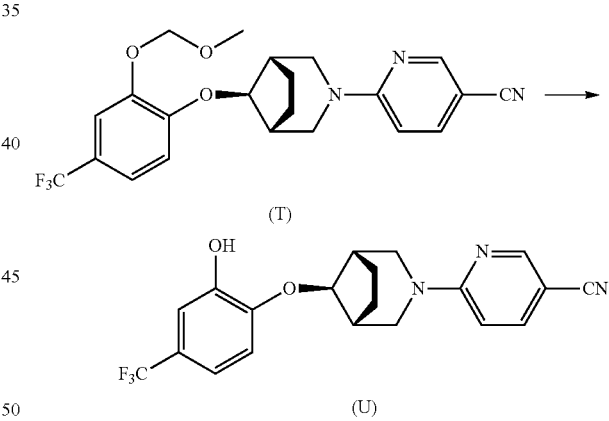

10 ml of 10% hydrochloric acid was added to 10 ml of THF solution containing 0.82 g of the compound (T) at room temperature. The mixture was refluxed with heating for 30 minutes, poured into water, and extracted with ethyl acetate. The organic layer was washed With saline and dried with anhydrous magnesium sulfate. 0.74 g of the target compound (U) was obtained by evaporating the solvents under reduced pressure.

$^1$H-NMR(CDCl$_3$, δppm): 1.62-1.75(m, 2H), 1.91-1.98(m, 2H), 2.65(brs, 2H), 3.17(d, 2H), 4.26(d, 2H), 4.66(s, 1H), 5.63(s, 1H), 6.60(d, 1H), 6.98(d, 1H), 7.13(d, 1H) 7.16(s, 1H), 7.63(d, 1H), 8.42(s, 1H)

This compound was directly used in the next step without purification.

Step 4

Production of 8β-[2-isopropylideneaminooxy-4-(trifluoromethyl)phenoxy]-3-(5-cyano-pyridin-2-yl)-3-azabicyclo[3.2.1]octane (W)

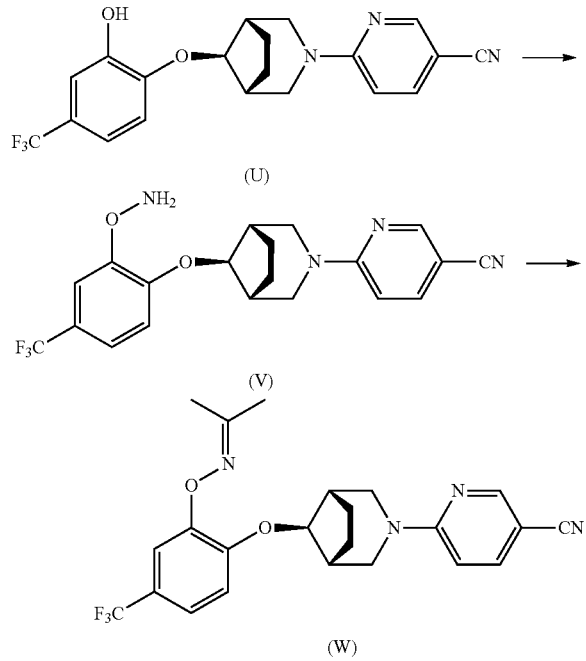

0.76 g of a compound (V) was synthesized by the method described in Japanese Patent Application Laid-Open No. 2001-81071 using 0.74 g of the compound (U).

$^1$H-NMR(CDCl$_3$, δppm): 1.55-1.68(m, 2H), 1.99-2.04(m, 2H), 2.59(brs, 2H), 3.13(d, 2H), 4.22(d, 2H), 4.60(s, 1H), 6.00(brs, 2H), 6.59(d, 1H), 6.98(d, 1H), 7.20(d, 1H), 7.60(d, 2H), 8.01(s, 1H), 8.41(s, 1H)

3 ml of acetone and 1 drop of concentrated hydrochloric acid were added to 3 ml of ethanol solution containing 0.76 g of the compound (V) and the entire mixture was stirred for 1 hour at room temperature. The mixture was poured into water and extracted with ethyl acetate. After being washed with water and dried with anhydrous magnesium sulfate, the organic layer was filtered and then vacuum-concentrated. The concentrate was purified by silica gel column chromatography (eluant: mixed solvent of n-hexane and ethyl acetate) to obtain 0.45 g of the target compound (W). The structure was confirmed by NMR. Melting temperature: 120-122° C.

Example 8

Production of 9β-[2-cyclopropylmethoxy-4-(trifluoromethyl)phenoxy]-7-[6-(trifluoromethyl)-3-pridazyl]-3-oxa-7-azabicyclo[3.3.1]nonane (AC)

Step 1

Production of N-benzyl-3-oxa-7-azabicyclo[3.3.1]nonan-9-ol (Z)

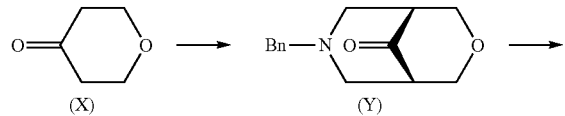

-continued

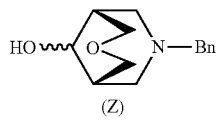

1.2 g of acetic acid, 80 ml of methanol, and 5.33 g of 90% formalin were added to 2.2 g of benzylamine in this order. Furthermore, while gradually heating the mixture from 20° C. to 45° C., 2.0 g of the compound (X) was added dropwise thereto and the resulting mixture was refluxed for 5.5 hours and stirred overnight at room temperature.

The solvents were evaporated under reduced pressure from the reaction mixture and 100 ml of water and 2 ml of concentrated hydrochloric acid were added to the obtained residue and washed with diethylether. pH of the aqueous layer was adjusted to 7 or more by adding sodium hydroxide and extracted with chloroform. After drying the organic layer with anhydrous magnesium sulfate, the solvents were evaporated under reduced pressure and the residue was purified by silica gel column chromatography (chloroform:methanol=10:1 (v/v)) to obtain 4.09 g of a compound (Y). Yield 88.5%

Subsequently, 1.86 g of sodium borohydride was added to 30 ml of 2-propanol solution containing 2.24 g of the compound (Y) at 0° C. and thereafter, 15 ml of water was added thereto and the resulting mixture was heated to room temperature and stirred for one day. After cooling the reaction mixture to 0° C., 75 ml of 10% hydrochloric acid was added thereto and thereafter, 45 ml of 10% sodium hydroxide was added thereto at the same temperature. The resulting mixture was extracted with chloroform and the organic layer was dried with anhydrous magnesium sulfate. The solvents were evaporated under reduced pressure to obtain 1.56 g of the compound (Z) as a viscous oil. Yield 83.8%

Step 2

Production of the Compound (AA)

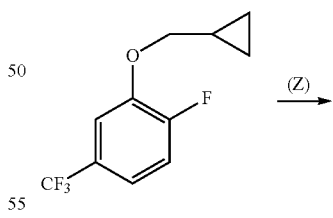

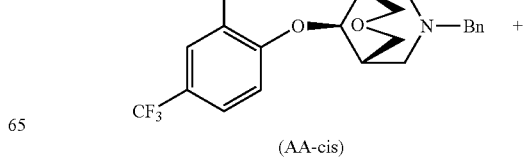

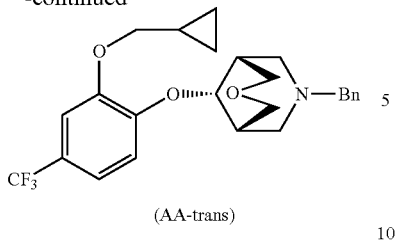

(AA-trans)

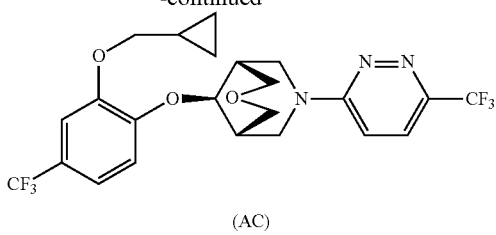

(AC)

0.40 g of 60% sodium hydride was added to 20 ml of DMF solution containing 1.56 g of the compound (Z) obtained in Step 1 and the resulting mixture was stirred for 15 minutes at room temperature. 2.35 g of 4-fluoro-3-(cyclopropyl-methoxy)benzotrifluoride was added to the mixture and the resultant mixture was stirred for 3 hours at 100° C. After cooling the reaction mixture to room temperature, water was poured thereto and extracted with ethyl acetate. After being washed with saturated saline and dried with anhydrous magnesium sulfate, the organic layer was filtered and vacuum-concentrated to obtain a crude compound (AA).

The obtained crude compound (AA) was purified by silica gel column chromatography (eluant: n-hexane:ethyl acetate=2:3 (v/v)) to obtain 0.98 g of a compound (AA-cis) as a viscous oil (yield 32.7%) and 0.76 g of a compound (AA-trans) as a viscous oil (yield 25.4%), respectively.

NMR data of AA-cis:

$^1$H-NMR(CDCl$_3$, δppm): 0.34-0.44(m, 2H), 0.60-0.67(m, 2H), 1.26-1.31(m, 2H), 1.94(brs, 2H), 2.49(d, 2H), 3.17(d, 2H), 3.57(s, 2H), 3.79(d, 2H), 3.88(d, 2H), 4.27(d, 2H), 4.43(t, 1H), 6.94(d, 1H), 7.10(s, 1H), 7.17(d, 1H), 7.20-7.40(m, 5H)

NMR data of AA-trans:

$^1$H-NMR(CDCl$_3$, δppm): 0.39-0.44(m, 2H), 0.62-0.71(m, 2H), 1.25-1.35(m, 1H), 2.04(brs, 2H), 2.84(brs, 4H), 3.55(s, 2H), 3.82(d, 2H), 3.89(d, 2H), 4.13(d, 2H), 4.59(t, 1H), 6.95(d, 1H), 7.10(s, 1H), 7.14(d, 1H), 7.20-7.42(m, 5H)

Step 3

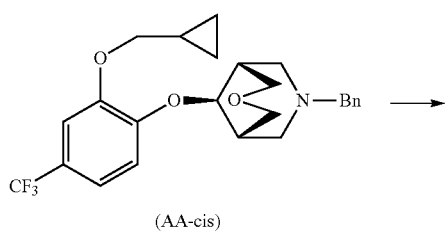

(AA-cis)

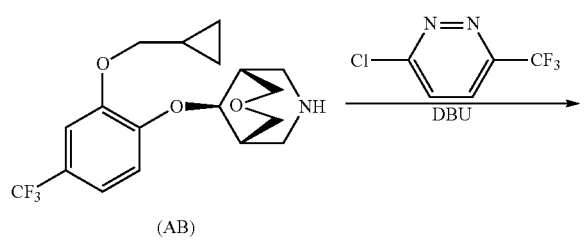

(AB)

0.20 g of 10% Pd/C was added to 20 ml of ethanol solution containing 0.98 g of the compound (AA-cis) obtained in Step 2 and the entire mixture was stirred for 6.5 hours at 60° C. under hydrogen atmosphere (atmospheric pressure). The reaction mixture was filtered and the filtrate was evaporated under reduced pressure to obtain 0.75 g of a debenzylated product (AB) as an oily matter. Yield 95.9%

$^1$H-NMR(CDCl$_3$, δppm): 0.35-0.40(m, 2H), 0.60-0.69(m, 2H), 1.23-1.34(m, 1H), 1.83(brs, 2H), 1.99(brs, 1H), 3.04(d, 2H), 3.38(d, 2H), 3.85-3.91(m, 4H), 4.35(d, 2H), 4.59(t, 1H), 6.95(d, 1H), 7.10(s, 1H), 7.12(d, 1H)

0.19 g of 3-chloro-6-(trifluoromethyl)pyridazine and 0.15 g of DBU were added to 3 ml of N-methylpyrrolidone solution containing the obtained compound (AB) and the resulting mixture was stirred for 3 hours at 120 to 130° C. After cooling the reaction mixture to room temperature, water was poured thereto and extracted with ethyl acetate. After being washed with saturated saline and dried with anhydrous magnesium sulfate, the organic layer was filtered and vacuum-concentrated. The obtained residue was purified by silica gel column chromatography (eluant: n-hexane:ethyl acetate=1:1 (v/v)) to obtain 0.24 g of the target compound (AC). Yield 57%, mp. 93 to 95° C.

Examples of the compounds of the present invention produced by the method according to the above Examples are shown in the Table below including the compounds produced in the above Examples. Note that in the Table below, R$^1$ and R$^2$ show substituents including substituents associated by two or more substituents so that the Table is simplified. Also, the description "vis" shows that the compound is a viscous oil and the description "amor" shows that the compound is amorphous. Moreover, nD21.8-1.5008 means that the refractive index at 21.8° C. is 1.5008 (the same also applies to others). In addition, the description "cPr" means cyclopropyl, the description "cHex" means cyclohexyl (the same also applies to others), the description "Ac" means acetyl, the description "nPr" means normal propyl, the description "iPr" means isopropyl, the description "nBu" means normal butyl, the description "iBu" means isobutyl, and the description "tBu" means tertiary butyl, and the description "TMS" means trimethylsilyl and the description "THF" means tetrahydrofuranyl.

TABLE 1

| Compound No. | R² | X | R¹ | Physical constant [ ]: Melting point °C. |
|---|---|---|---|---|
| 1-1 | 5-CF₃ | O | 2-OnPr-4-CF₃ | [90-92] |
| 1-2 | 5-CF₃ | O | 2-CHO-4-CF₃ | [122-123] |
| 1-3 | 5-CF₃ | O | 2-CH₂OH-4-CF₃ | vis |
| 1-4 | 5-CF₃ | O | 2-CH₂OCH(OMe)Me-4-CF₃ | [82-85] |
| 1-5 | 5-CF₃ | O | 2-CH₂OEt-4-CF₃ | vis |
| 1-6 | 5-CF₃ | O | 2-Cl-4-CF₃ | [92-93] |
| 1-7 | 5-CF₃ | O | 2-C(O)OiPr-4-CF₃ | vis |
| 1-8 | 5-CF₃ | O | 2,6-(NO₂)₂-4-CF₃ | vis |
| 1-9 | 5-CF₃ | O | 2-C(O)NHCH(Me)CH₂OH-4-CF₃ | amor |
| 1-10 | 5-CF₃ | O | 2-CH=NOEt-4-CF₃ | vis |
| 1-11 | 5-CF₃ | O | (E)-2-CH=NOiPr-4-CF₃ | [79-80] |
| 1-12 | 5-CF₃ | O | 2-CH=NO-propargyl-4-CF₃ | [84-86] |
| 1-13 | 5-CF₃ | O | 2-(5-Me-oxazoline-2-yl)-4-CF₃ | vis |
| 1-14 | 3-Cl-5-CF₃ | O | 2-CH₂OEt-4-CF₃ | vis |
| 1-15 | 5-CF₃ | O | 2-OMe-4-CF₃ | [127-130] |
| 1-16 | 5-CF₃ | O | (Z)-2-CH=NOiPr-4-CF₃ | vis |
| 1-17 | 5-CF₃ | O | 2-C(O)OEt-4-CF₃ | vis |
| 1-18 | 5-CF₃ | O | 2-C(O)OtBu-4-CF₃ | [95-98] |
| 1-19 | 3-Cl-5-CF₃ | O | 2-C(O)OiPr-4-CF₃ | vis |
| 1-20 | 5-CF₃ | O | 6-Cl-2-C(O)OiPr-4-CF₃ | vis |
| 1-21 | 5-CF₃ | O | 2-CH=NOMe-4-CF₃ | vis |
| 1-22 | 5-CF₃ | O | 2-CH=NOEt-4-CF₃ | |
| 1-23 | 5-CF₃ | O | 2-C(O)OCH₂cPr-4-CF₃ | vis |
| 1-24 | 5-CF₃ | O | 2-C(O)OCH₂CF₃-4-CF₃ | vis |
| 1-25 | 5-CF₃ | O | 2-C(O)OiBu-4-CF₃ | vis |
| 1-26 | 5-CF₃ | O | 2-C(O)OnPr-4-CF₃ | vis |
| 1-27 | 5-CF₃ | O | 2-CH(OH)CH₂CH(Me)₂-4-CF₃ | amor |
| 1-28 | 5-CF₃ | O | 2-C(O)OCH(Me)CH=CH₂-4-CF₃ | vis |
| 1-29 | 5-CF₃ | O | 2-C(O)OcPen-4-CF₃ | vis |
| 1-30 | 5-CF₃ | O | 2-C(O)ON=C(Me)₂-4-CF₃ | vis |
| 1-31 | 5-CF₃ | O | 2-OCH₂cPr-4-CF₃ | [88-90] |
| 1-32 | 5-CF₃ | O | 2-OEt-4-CF₃ | [102-105] |
| 1-33 | 5-CF₃ | O | 2-C(O)OCH₂CHF₂-4-CF₃ | vis |
| 1-34 | 5-CF₃ | O | 2-OnBu-4-CF₃ | [90-92] |
| 1-35 | 5-CF₃ | O | 2-OnPr-4-CN | [107-110] |
| 1-36 | 5-CF₃ | O | 2-C(O)OCH₂OMe-4-CF₃ | vis |
| 1-37 | 5-CF₃ | O | 2-C(O)OCH₂tBu-4-CF₃ | [100-102] |
| 1-38 | 5-CF₃ | O | 2-C(O)N(Me)₂-4-CF₃ | vis |
| 1-39 | 5-CF₃ | O | 2-C(O)OCH(Me)CH(Me)₂-4-CF₃ | vis |
| 1-40 | 5-CF₃ | O | 2-C(O)OCH(Et)₂-4-CF₃ | vis |
| 1-41 | 5-CF₃ | O | 2-C(O)O(THF-3-yl)-4-CF₃ | vis |
| 1-42 | 5-CF₃ | NH | 2-C(O)OiPr-4-CF₃ | vis |
| 1-43 | 5-CF₃ | O | 2-C(O)O(CH₂)₂OMe-4-CF₃ | vis |
| 1-44 | 5-CF₃ | O | 2-C(O)OCH(Me)CH₂OMe-4-CF₃ | vis |
| 1-45 | 5-CF₃ | O | 2-C(O)OCH(CN)Me-4-CF₃ | vis |
| 1-46 | 5-CF₃ | O | 2-C(O)OCH(Cl)Et-4-CF₃ | vis |
| 1-47 | 5-CF₃ | O | 2-C(O)SiPr-4-CF₃ | vis |
| 1-48 | 5-CF₃ | O | 2-OBn-4-CF₃ | [98-102] |
| 1-49 | 5-CF₃ | O | 2-OH-4-CF₃ | [130-131] |
| 1-50 | 5-CF₃ | O | 2-OCH₂CH(Me)OMe-4-CF₃ | [116-120] |
| 1-51 | 5-CN | O | 2-C(O)OiPr-4-CF₃ | [124-126] |

TABLE 1-continued

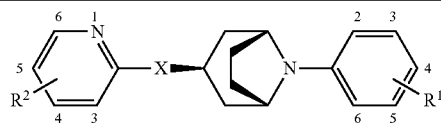

| Compound No. | R² | X | R¹ | Physical constant [ ]: Melting point ° C. |
|---|---|---|---|---|
| 1-52 | 5-CF₃ | O | 2-CH(OTMS)CH₂CN-4-CF₃ | [131-133] |
| 1-53 | 5-CF₃ | O | 2-CH(OH)CH₂CN-4-CF₃ | [24-25] |
| 1-54 | 5-CN | O | 2-OnPr-4-CF₃ | [141-142] |
| 1-55 | 5-CF₃ | O | 2-OCH₂cPr-4-C₃F₇ | nD22.2-1.4942 |
| 1-56 | 3-Me | O | 4-Ph | |
| 1-57 | 3-F | O | 3,4,5,6-F₄ | |
| 1-58 | 5-CN | S | 2-CN | |
| 1-59 | 5-NO₂ | S | 3-CF₃ | |
| 1-60 | 5-CHO | S | 4-iPr | |
| 1-61 | 4-OMe | S | 3,5-Me₂ | |
| 1-62 | 4-cPr | S | 3-NO₂ | |
| 1-63 | 5-OcHex | SO₂ | 3-Br | |
| 1-64 | 3-CH₂CH₂cPr | SO₂ | 3-cPr | |
| 1-65 | 4-OCH₂cPr | SO₂ | 4-OcPr | |
| 1-66 | 4-OCH=CH₂ | SO₂ | 2-CH₂cPr | |
| 1-67 | 5-OCF₃ | SO₂ | 2-OCH₂cPr | |
| 1-68 | 4-OCH=CHCH₂CF₃ | NH | 4-OCH=CH₂ | |
| 1-69 | 4-CO₂Et | NH | 2-OCH₂Cl | |
| 1-70 | 6-F | NH | 2-OCH=CBr₂ | |
| 1-71 | 6-CN | NMe | 3-NO₂ | |
| 1-72 | 6-NO₂ | NAc | 4-OCF₃ | |
| 1-73 | 6-OcPr | NMe | 4-CN | |

TABLE 2

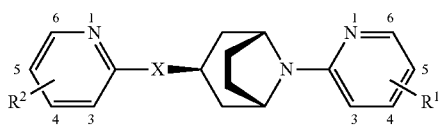

| Compound No. | R² | X | R¹ | Physical constant [ ]: Melting point ° C. |
|---|---|---|---|---|
| 2-1 | 5-CF₃ | O | 4-CF₃-6-Cl | nD22.1-1.5134 |
| 2-2 | 4-CF₃-6-Cl | O | 5-CF₃ | vis |
| 2-3 | 5-CF₃ | O | 5-CF₃ | [104-105] |
| 2-4 | 5-CF₃-6-OnPr | O | 5-CF₃ | [90-93] |
| 2-5 | 5-CF₃ | S | 4-cPr | |
| 2-6 | 3-Me | S | 3-OcPr | |
| 2-7 | 3-F | S | 3,5-Me₂ | |
| 2-8 | 5-CN | S | 4-CF₃ | |
| 2-9 | 5-NO₂ | SO₂ | 5-CO₂Et | |
| 2-10 | 5-CHO | SO₂ | 4-CH=CF₂ | |
| 2-11 | 4-OMe | SO₂ | 5-CH=CMe₂ | |
| 2-12 | 4-cPr | SO₂ | 3-OCH₂CH₂cPr | |
| 2-13 | 5-OcHex | NH | 4-CH₂cPr | |
| 2-14 | 3-CH₂CH₂cPr | NH | 3-OEt-4-cPr | |
| 2-15 | 4-OCH₂cPr | NMe | 4-CHO | |
| 2-16 | 6-Me | NMe | 5-NO₂ | |

TABLE 3

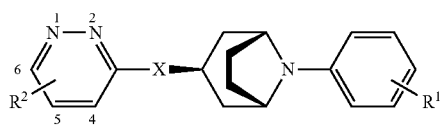

| Compound No. | R² | X | R¹ | Physical constant [ ]: Melting point ° C. |
|---|---|---|---|---|
| 3-1 | 6-CF₃ | O | 2-C(O)OiPr-4-CF₃ | [154-157] |
| 3-2 | 6-CF₃ | O | 2-CH₂OEt-5-CF₃ | nD22.2-1.4996 |
| 3-3 | 4-CF₃ | O | 2-Me | |
| 3-4 | 5-CF₃ | O | 3-Cl | |
| 3-5 | 4-Br | S | 4-CF₃ | |
| 3-6 | 5-Me | S | 3-NO₂ | |
| 3-7 | 6-CF₃ | S | 3-CO₂Me | |
| 3-8 | 6-CF₃ | SO₂ | 4-tBu | |
| 3-9 | 4-cPr | SO₂ | 3-cPr | |
| 3-10 | 6-CF₃ | NH | 4-OcHex | |
| 3-11 | 6-OCH₂CH₂cPr | NH | 4-NMe₂ | |
| 3-12 | 5-CH=CMe₂ | NH | 3-iPr | |
| 3-13 | 6-CF₃ | NMe | 4-OCF₃ | |
| 3-14 | 4-NO₂ | NMe | 2-CN | |
| 3-15 | 5-CHO | NAc | 4-CHO | |

TABLE 4

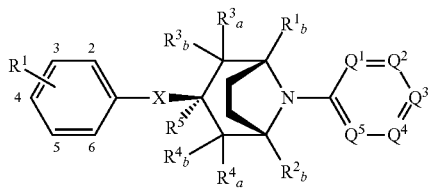

Note that R1b, R2b, R3a, R3b, R4a, R4b, and R5 represent hydrogen atom, respectively, unless otherwise indicated.

| Compound No. | $R^1$ | $Q^1$ | $Q^2$ | $Q^3$ | $Q^4$ | $Q^5$ | X | Physical constant [ ]: Melting point °C. | Remark |
|---|---|---|---|---|---|---|---|---|---|
| 4-1 | 2-OnPr-4-CF$_3$ | N | N | C—CF$_3$ | CH | CH | O | [197-199] | |
| 4-2 | 2-OnPr-4-CF$_3$ | N | CH | C—Me | CH | N | O | [175-176] | |
| 4-3 | 2-OnPr-4-CF$_3$ | N | C—Cl | N | CH | C—Me | O | [128-132] | |
| 4-4 | 2-OnPr-4-CF$_3$ | N | C—Cl | C—Me | CH | N | O | [83-89] | |
| 4-5 | 2-OnPr-4-CF$_3$ | N | CH | C—CF$_3$ | CH | N | O | [152-155] | |
| 4-6 | 2-OnPr-4-CF$_3$ | N | N | C—CF$_3$ | CH | CH | O | amor | $R_b^3$ = $R_b^4$ = Me |
| 4-7 | 2-OCH$_2$CH(Me)OMe-4-CF$_3$ | N | N | C—CF$_3$ | CH | CH | O | [181-185] | |
| 4-8 | 2-OCH$_2$cPr-4-CF$_3$ | N | N | C—CN | CH | CH | O | [213-215] | |
| 4-9 | 2-OCH$_2$cPr-4-CF$_3$ | N | N | C—CF$_3$ | CH | CH | O | [204-206] | |
| 4-10 | 2-CO$_2$iPr-4-CF$_3$ | N | N | C—CN | CH | CH | O | [219-221] | |
| 4-11 | 2-OnBu-4-CF$_3$ | N | N | C—CF$_3$ | CH | CH | O | [197-199] | |
| 4-12 | 2-OiBu-4-CF$_3$ | N | N | C—CF$_3$ | CH | CH | O | [223-224] | |
| 4-13 | 2-OEt-4-CF$_3$ | N | N | C—CF$_3$ | CH | CH | O | [192-194] | |
| 4-14 | 2-CO$_2$iPr-4-CF$_3$ | N | N | C—CF$_3$ | CH | CH | O | [201-203] | |
| 4-15 | 2-OCH$_2$CH(F)Me-4-CF$_3$ | N | N | C—CN | CH | CH | O | [215-218] | |
| 4-16 | 2-OCH$_2$CH(F)Me-4-CF$_3$ | N | N | C—CF$_{3'}$ | CH | CH | O | [197-200] | |
| 4-17 | 2-OCH$_2$cPr-4-CF$_3$ | CH | N | C—Cl | CH | CH | O | [148-150] | |
| 4-18 | 2-OCH$_2$cPr-4-CF$_3$ | CH | N | C—CN | CH | CH | O | [126-128] | |
| 4-19 | 2-OnPr-4-CF$_3$ | N | N | C—CF$_3$ | CH | CH | O | [214-216] | sulfate |
| 4-20 | 2-OnPr-4-CF$_3$ | N | N | C—CF$_3$ | CH | CH | O | [220up] | borate |
| 4-21 | 4-CF$_3$ | N | N | C—CF$_{3'}$ | CH | CH | O | [187-188] | |
| 4-22 | 2-OnPr-4-CF$_3$ | CH | N | C—Cl | CH | CH | O | [149-150] | |
| 4-23 | 4-CF$_3$ | C—OnPr | N | C—CF$_3$ | CH | CH | O | nD21.9-1.5132 | |
| 4-24 | 2-CH$_2$OEt-4-CF$_3$ | N | N | C—CF$_3$ | CH | CH | O | vis | |
| 4-25 | 4-CF$_3$ | CH | CH | N | CH | CH | O | | |
| 4-26 | 2,6-Me$_2$ | CH | CMe | N | CBr | CH | O | | |
| 4-27 | 4-OMe | N | N | C—CF$_3$ | CH | CH | S | | |
| 4-28 | 3-NO$_2$ | N | N | C—CF$_3$ | CH | CH | S | | |
| 4-29 | 2-F | N | N | C—CF$_3$ | CH | CH | S | | |
| 4-30 | 3-CHO | N | N | C—CN | CH | CH | S | | |
| 4-31 | 3-OiPr | N | N | C—CF$_3$ | CH | CH | S | | |
| 4-32 | 4-Me | CH | N | C—Cl | CH | CH | S | | |
| 4-33 | 4-cPr | CH | N | C—CN | CH | CH | S | | |
| 4-34 | 3-OcPr | N | N | C—CF$_3$ | CH | CH | S | | |
| 4-35 | 4-CH$_2$cPr | N | N | C—CF$_3$ | CH | CH | SO$_2$ | | |
| 4-36 | 2-OCH$_2$CH$_2$cPr | N | N | C—CF$_3$ | CH | CH | SO$_2$ | | |
| 4-37 | 3-OCH=CMe$_2$ | N | N | C—CF$_3$ | CH | CH | SO$_2$ | | |
| 4-38 | 4-OCF$_3$ | N | N | C—CF$_3$ | CH | CH | SO$_2$ | | |
| 4-39 | 4-OCF$_3$ | N | N | C—CN | CH | CH | SO$_2$ | | |
| 4-40 | 3-CO$_2$Me | N | N | C—CF$_3$ | CH | CH | SO$_2$ | | |
| 4-41 | 3-Me | CH | N | C—Cl | CH | CH | NH | | |
| 4-42 | 4-tBu | CH | N | C—CN | CH | CH | NH | | |
| 4-43 | 2-CH=CHMe | N | N | C—CF$_3$ | CH | CH | NH | | |
| 4-44 | 2-OCH$_2$cPr-4-CF$_3$ | N | N | C—CF$_3$ | CH | CH | NH | | |
| 4-45 | 2-OCH$_2$cPr-4-CF$_3$ | N | N | C—CF$_3$ | CH | CH | NH | | |
| 4-46 | 2-CO$_2$iPr-4-CF$_3$ | N | N | C—CN | CH | CH | NH | | |
| 4-47 | 2-OnBu-4-CF$_3$ | N | N | C—CF$_3$ | CH | CH | NMe | | |
| 4-48 | 2-OiBu-4-CF$_3$ | CH | N | C—Cl | CH | CH | NEt | | |
| 4-49 | 2-OEt-4-CF$_3$ | CH | N | C—CN | CH | CH | NAc | | |
| 4-50 | 2-CO$_2$iPr-4-CF$_3$ | N | N | C—CF$_{3'}$ | CH | CH | NAc | | |
| 4-51 | 2-OnPr-4-CF$_3$ | N | CH | C—CN | CH | CH | O | [124-125] | |
| 4-52 | 2-OCH$_2$cPr-4-CF$_3$ | N | CH | C—CN | CH | CH | O | [129-131] | |
| 4-53 | 2-OCH$_2$CHFMe-4-CF$_3$ | N | CH | C—CN | CH | CH | O | [105-109] | |
| 4-54 | 2-OCH$_2$CH$_2$OMe-4-CF$_3$ | N | CH | C—CN | CH | CH | O | nD24.7-1.5697 | |
| 4-55 | 2-CO$_2$iPr-4-CF$_3$ | N | CH | C—CN | CH | CH | O | [133-135] | |
| 4-56 | 2-OCH$_2$iPr-4-CF$_3$ | N | CH | C—CN | CH | CH | O | [139-141] | |
| 4-57 | 2-OCH$_2$C(Me)=CH$_2$-4-CF$_3$ | N | CH | C—CN | CH | CH | O | [90-93] | |
| 4-58 | 2-OCH$_2$CH(Me)OMe-4-CF$_3$ | N | CH | C—CN | CH | CH | O | [114-118] | |
| 4-59 | 2-ON=C(Me)$_2$-4-CF$_3$ | N | CH | C—CN | CH | CH | O | [125-128] | |
| 4-60 | 2-OnPr-4-OCF$_3$ | N | CH | C—CF$_3$ | CH | CH | NH | [89-90] | |
| 4-61 | 2-OMe-4-OCF$_3$ | N | CH | C—CF$_3$ | CH | CH | NH | [114-116] | |
| 4-62 | 2-OnPr-4-CF$_3$ | N | CH | C—CF$_3$ | CH | CH | NH | [96-97] | |

TABLE 4-continued

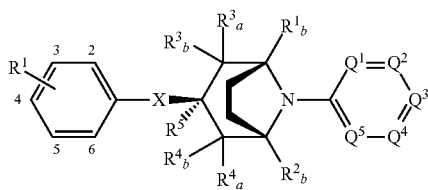

Note that R1b, R2b, R3a, R3b, R4a, R4b, and R5 represent hydrogen atom, respectively, unless otherwise indicated.

| Compound No. | R¹ | Q¹ | Q² | Q³ | Q⁴ | Q⁵ | X | Physical constant [ ]: Melting point ° C. | Remark |
|---|---|---|---|---|---|---|---|---|---|
| 4-63 | 2-Me-3-CF₃ | N | CH | C—CF₃ | CH | CH | NH | [124-125] | |
| 4-64 | 2-OnPr-4-CF₃ | CH | CH | C—CF₃ | CH | CH | O | vis | |
| 4-65 | 2-OnPr-4-CF₃ | C—Cl | CH | C—CF₃ | CH | CH | O | [104-105] | |
| 4-66 | 2-OnPr-4-CF₃ | C—NO₂ | CH | C—CF₃ | CH | CH | O | vis | |
| 4-67 | 2-OnPr-4-CF₃ | C—F | CH | C—CF₃ | CH | CH | O | vis | |
| 4-68 | 2-OnPr-4-CF₃ | C—N(SO₂Me)₂ | CH | C—CF₃ | CH | CH | O | amor | |
| 4-69 | 2-OnPr-4-CF₃ | CH | CH | C—OMe | CH | CH | O | [119-120] | |
| 4-70 | 2-OnPr-4-CF₃ | CH | C—F | C—CF₃ | CH | CH | O | vis | |
| 4-71 | 2-OnPr-4-CF₃ | CH | CH | C—OCF₃ | CH | CH | O | vis | |
| 4-72 | 2-OnPr-4-CF₃ | CH | CH | C—NO₂ | CH | CH | O | [114-117] | |
| 4-73 | 2-OnPr-4-CF₃ | CH | CH | C—NH₂ | CH | CH | O | vis | |
| 4-74 | 2-OnPr-4-CF₃ | CH | CH | C—NHSO₂CF₃ | CH | CH | O | [90-95] | |
| 4-75 | 2-OnPr-4-CF₃ | CH | CH | C—Br | CH | CH | O | vis | |
| 4-76 | 2-OnPr-4-CF₃ | CH | C—Cl | C—Cl | CH | CH | O | vis | |
| 4-77 | 2-OnPr-4-CF₃ | CH | CH | C—tBu | CH | CH | O | [139-141] | |
| 4-78 | 2-OnPr-4-CF₃ | CH | CH | C—Ph | CH | CH | O | [40-50] | |
| 4-79 | 2-OnPr-4-CF₃ | CH | C—OEt | C—CF₃ | CH | CH | O | vis | |
| 4-80 | 2-OnPr-4-CF₃ | CH | C—nPr | C—CF₃ | CH | CH | O | nD20.4-1.4827 | |
| 4-81 | 2-OnPr-4-CF₃ | CH | C—C=NOEt | C—CF₃ | CH | CH | O | [103-105] | |
| 4-82 | 2-OnPr-4-CF₃ | CH | C—CO₂iPr | C—CF₃ | CH | CH | O | vis | |

TABLE 5

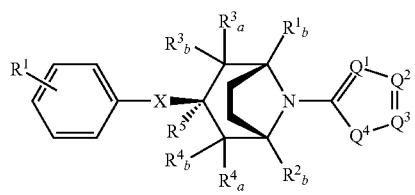

Note that R1b, R2b, R3a, R3b, R4a, R4b, and R5 represent hydrogen atom, respectively, unless otherwise indicated.

| Compound No. | R¹ | Q¹ | Q² | Q³ | Q⁴ | X | Physical constant [ ]: Melting point ° C. |
|---|---|---|---|---|---|---|---|
| 5-1 | 2-OnPr-4-CF₃ | N | N | C—CF₃ | S | O | [93-95] |
| 5-2 | 2-OCH₂cPr-4-CF₃ | N | N | C—CF₃ | S | O | [110-112] |
| 5-3 | 2-CO₂iPr-4-CF₃ | N | N | C—CF₃ | S | O | [112-114] |
| 5-4 | 2-ON=C(Me)₂-4-CF₃ | N | N | C—CF₃ | S | O | [121-124] |
| 5-5 | 2-OiBu-4-CF₃ | N | N | C—CF₃ | S | O | [147-150] |
| 5-6 | 2-OCH₂C(Me)=CH₂-4-CF₃ | N | N | C—CF₃ | S | O | [121-124] |
| 5-7 | 2-OCH₂CH(Me)OMe-4-CF₃ | N | N | C—CF₃ | S | O | [98-102] |
| 5-8 | 2-OCH₂CH(F)Me-4-CF₃ | N | N | C—CF₃ | S | O | [105-108] |
| 5-9 | 2-OnPr-4-CF₃ | C—CN | C—CF₃ | N | N—Me | O | [91-92] |
| 5-10 | 2-OnPr-4-CF₃ | C—C(O)NH₂ | C—CF₃ | N | N—Me | O | [180-181] |
| 5-11 | 4-CF₃ | CH | CH | CH | O | S | |
| 5-12 | 2-CF₃-3-Cl | N | CH | CMe | O | S | |
| 5-13 | 4-CF₃ | CH | N | CH | O | S | |
| 5-14 | 4-CF₃-2-OnPr | N | N | CH | O | S | |
| 5-15 | 3-CF₃ | N | N | CH | O | S | |
| 5-16 | 3-Me | O | CH | CH | NH | SO₂ | |
| 5-17 | 3-F | CH | CH | CH | NH | SO₂ | |
| 5-18 | 2-CN | CH | N | CH | NH | SO₂ | |
| 5-19 | 3-NO₂ | N | CH | C—CF₃ | NH | SO₂ | |

TABLE 5-continued

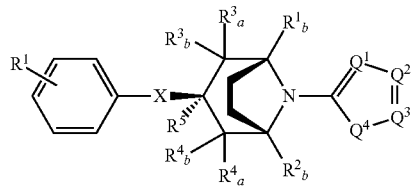

Note that R1b, R2b, R3a, R3b, R4a, R4b, and R5 represent hydrogen atom, respectively, unless otherwise indicated.

| Compound No. | $R^1$ | $Q^1$ | $Q^2$ | $Q^3$ | $Q^4$ | X | Physical constant [ ]: Melting point ° C. |
|---|---|---|---|---|---|---|---|
| 5-20 | 4-CHO | N | CH | CH | NH | $SO_2$ | |
| 5-21 | 4-OMe | CH | CH | CH | S | $SO_2$ | — |
| 5-22 | 4-cPr | N | CH | CH | S | $SO_2$ | |
| 5-23 | 2-OcHex | N | CH | CH | S | NH | |
| 5-24 | 3-$CH_2CH_2$cPr | N | CH | CH | S | NH | |
| 5-25 | 4-$OCH_2$cPr | N | CH | CH | S | NH | |
| 5-26 | 2-CHO | N | CH | CH | O | NH | |
| 5-27 | 3-OCH=CHMe | N | CMe | CH | O | NMe | |
| 5-28 | 2-$CO_2$Et | CH | CH | CH | O | NMe | |

TABLE 6

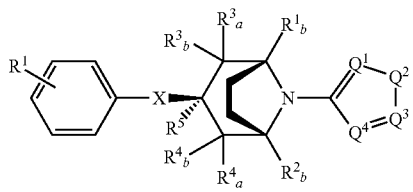

Note that R1b, R2b, R3a, R3b, R4a, R4b, and R5 represent hydrogen atom, respectively, unless otherwise indicated.

| Compound No. | $R^1$ | $Q^1$ | $Q^2$ | $Q^3$ | $Q^4$ | X | Physical constant [ ]: Melting point ° C. |
|---|---|---|---|---|---|---|---|
| 6-1 | 2-OnPr-4-$CF_3$ | N | NH | C—$CF_3$ | CH | O | vis |
| 6-2 | 2-OnPr-4-$CF_3$ | N | NMe | C—$CF_3$ | N | O | |
| 6-3 | 2-$OCH_2$cPr-4-$CF_3$ | N | NH | C—$CF_3$ | N | O | |
| 6-4 | 2-$CO_2$iPr-4-$CF_3$ | N | NH | C—$CF_3$ | N | S | |
| 6-5 | 2-ON=C(Me)$_2$-4-$CF_3$ | N | NH | C—$CF_3$ | N | S | |
| 6-6 | 2-OiBu-4-$CF_3$ | N | NEt | C—$CF_3$ | N | $SO_2$ | |
| 6-7 | 2-$OCH_2$C(Me)=$CH_2$-4-$CF_3$ | N | NAc | C—$CF_3$ | N | NAc | |
| 6-8 | 2-$OCH_2$CH(Me)OMe-4-$CF_3$ | N | NH | C—$CF_3$ | N | NH | |
| 6-9 | 2-$OCH_2$CH(F)Me-4-$CF_3$ | N | NH | C—$CF_3$ | N | NH | |
| 6-10 | 2-OnPr-4-$CF_3$ | C—CN | CH—$CF_3$ | N | N | O | |
| 6-11 | 2-OnPr-4-$CF_3$ | C—C(O)$NH_2$ | $CMe_2$ | N | N | O | |

TABLE 7

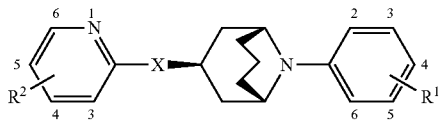

| Compound No. | $R^2$ | X | $R^1$ | Physical constant [ ]: Melting point °C. |
|---|---|---|---|---|
| 7-1 | 5-$CF_3$ | O | 2-OnPr-4-$CF_3$ | amor |
| 7-2 | 5-$CF_3$ | O | 2-CHO-4-$CF_3$ | nD22.2-1.5330 |
| 7-3 | 5-$CF_3$ | O | 2-$CH_2$OH-4-$CF_3$ | nD22.3-1.5194 |
| 7-4 | 5-$CF_3$ | O | 2-$CH_2$OEt-4-$CF_3$ | nD22.3-1.5003 |
| 7-5 | 3-Me | O | 2-OnPr-4-$CF_3$ | |
| 7-6 | 4-Ph | O | 4-$CF_3$ | |
| 7-7 | 3-OnPr | O | 2-$CF_3$-3-Cl | |
| 7-8 | 3-O$CH_2$cPr | O | 4-$CF_3$ | |
| 7-9 | 4-tBu | O | 4-$CF_3$-2-OnPr | |
| 7-10 | 4-O$CH_2$CHFMe | O | 3-$CF_3$ | |
| 7-11 | — | S | 3-Me | |
| 7-12 | 3-Br | S | 3-F | |
| 7-13 | 4-$CO_2$tBu | S | 2-CN | |
| 7-14 | 3-$CO_2$Et | S | 3-$NO_2$ | |
| 7-15 | 2-OCF=$CH_2$ | S | 4-CHO | |
| 7-16 | 5-OCH=CHMe | S | 4-OMe | |
| 7-17 | 3-O$CH_2$cPr | $SO_2$ | 4-cPr | |
| 7-18 | 4-$CH_2CH_2$cPr | $SO_2$ | 2-OcHex | |
| 7-19 | 3-OcPr | $SO_2$ | 3-$CH_2CH_2$cPr | |
| 7-20 | 4-cPr | NH | 4-O$CH_2$cPr | |
| 7-21 | 5-O$CF_3$ | NH | 2-OnPr-4-$CF_3$ | |
| 7-22 | 3,5-$Me_2$ | NH | 4-$CF_3$ | |
| 7-23 | 6-Cl | NH | 2-$CF_3$-3-Cl | |
| 7-24 | 5-$NO_2$ | NMe | 4-$CF_3$ | |
| 7-25 | 4-CHO | NAc | 4-$CF_3$-2-OnPr | |

TABLE 8

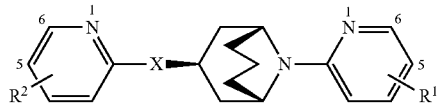

| Compound No. | $R^2$ | X | $R^1$ | Physical constant [ ]: Melting point °C. |
|---|---|---|---|---|
| 8-1 | 5-$CF_3$ | O | 5-$CF_3$ | nD22.7-1.5174 |
| 8-2 | 5-$CF_3$ | O | 3-Cl-5-$CF_3$ | nD23.0-1.5266 |
| 8-3 | 3-Me | O | 5-$CF_3$ | |
| 8-4 | 3-F | O | 4-cPr | |
| 8-5 | 5-CN | S | 3-OcPr | |
| 8-6 | 5-$NO_2$ | S | 3,5-$Me_2$ | |
| 8-7 | 5-CHO | S | 4-$CF_3$ | |
| 8-8 | 4-OMe | S | 5-$CO_2$Et | |
| 8-9 | 4-cPr | S | 4-CH=$CF_2$ | |
| 8-10 | 5-OcHex | $SO_2$ | 5-CH=$CMe_2$ | |
| 8-11 | 3-$CH_2CH_2$cPr | $SO_2$ | 3-O$CH_2CH_2$cPr | |
| 8-12 | 4-O$CH_2$cPr | $SO_2$ | 4-$CH_2$cPr | |
| 8-13 | 4-OCH=$CH_2$ | $SO_2$ | 3-OEt-4-cPr | |
| 8-14 | 5-O$CF_3$ | $SO_2$ | 4-CHO | |
| 8-15 | 4-OCH=$CHCH_2CF_3$ | NH | 5-$NO_2$ | |
| 8-16 | 4-$CO_2$Et | NH | 5-$CF_3$ | |
| 8-17 | 6-F | NH | 4-cPr | |
| 8-18 | 6-CN | NMe | 4-$CO_2$Et | |

TABLE 8-continued

| Compound No. | $R^2$ | X | $R^1$ | Physical constant [ ]: Melting point °C. |
|---|---|---|---|---|
| 8-19 | 6-$NO_2$ | NAc | 3-Me | |
| 8-20 | 6-OcPr | NMe | 5-O$CF_3$ | |
| 8-21 | 3-Me | O | 4-OMe | |
| 8-22 | 3-F | O | 5-Cl | |
| 8-23 | 4-OCH=$CF_2$ | S | 3-nBu | |

TABLE 9

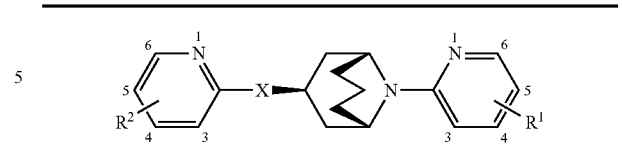

| Compound No. | $R^2$ | X | $R^1$ | Physical constant [ ]: Melting point °C. |
|---|---|---|---|---|
| 9-1 | 6-$CF_3$ | O | 2-OnPr-4-$CF_3$ | vis |
| 9-2 | 6-$CF_3$ | O | 4-$CF_3$ | nD22.3-l.5245 |
| 9-3 | 5-Me | O | 2-$CH_2$OEt-4-$CF_3$ | |
| 9-4 | 6-$CF_3$ | O | 2-Cl-4-$CF_3$ | |
| 9-5 | 6-$CF_3$ | O | 2-C(O)OiPr-4-$CF_3$ | |
| 9-6 | 4-cPr | O | 2,6-$(NO_2)_2$-4-$CF_3$ | |
| 9-7 | 6-$CF_3$ | S | 2-C(O)NHCH(Me)$CH_2$OH-4-$CF_3$ | |
| 9-8 | 6-O$CH_2CH_2$cPr | S | 2-CH=NOEt-4-$CF_3$ | |
| 9-9 | 5-OCH=$CMe_2$ | S | (E)-2-CH=NOiPr-4-$CF_3$ | |
| 9-10 | 6-$CF_3$ | S | 2-CH=NO-propargyl-4-$CF_3$ | |
| 9-11 | 4-$NO_2$ | S | 2-(5-Me-oxazoline-2-yl)-4-$CF_3$ | |
| 9-12 | 5-CHO | S | 2-$CH_2$OEt-4-$CF_3$ | |
| 9-13 | 5-Me | $SO_2$ | 2-OMe-4-$CF_3$ | |
| 9-14 | 6-$CF_3$ | $SO_2$ | (Z)-2-CH=NOiPr-4-$CF_3$ | |
| 9-15 | 6-$CF_3$ | $SO_2$ | 2-C(O)OEt-4-$CF_3$ | |
| 9-16 | 4-CN | $SO_2$ | 2-C(O)OtBu-4-$CF_3$ | |
| 9-17 | 5-Br | NH | 2-C(O)OiPr-4-$CF_3$ | |
| 9-18 | 4-OcPr | NH | 6-Cl-2-C(O)OiPr-4-$CF_3$ | |
| 9-19 | 5-OtBu | NH | 3-Br | |
| 9-20 | 5-OCH=CHMe | NH | 4-Me | |
| 9-21 | 4-OCH=CHF | NMe | — | |
| 9-22 | 6-$CO_2$Me | NAc | 2-Cl | |

TABLE 10

| Compound No. | R¹ | Q¹ | Q² | Q³ | Q⁴ | Q⁵ | X | Physical constant [ ]: Melting point °C. |
|---|---|---|---|---|---|---|---|---|
| 10-1 | 2-OnPr-4-CF$_3$ | N | N | C—CF$_3$ | CH | CH | O | [116-117] |
| 10-2 | 2-OCH$_2$cPr-4-CF$_3$ | N | N | C—CF$_3$ | CH | CH | O | [112-113] |
| 10-3 | 2-OiBu-4-CF$_3$ | N | N | C—CF$_3$ | CH | CH | O | [148-149] |
| 10-4 | 2-CH$_2$OEt-4-CF$_3$ | N | N | C—CF$_3$ | CH | CH | O | nD22.1-1.5088 |
| 10-5 | 4-CF$_3$ | N | N | C—CF$_3$ | CH | CH | O | [130-131] |
| 10-6 | 2-OCH$_2$CH(F)Me-4-CF$_3$ | N | CH | CH | N | C—Me | O | |
| 10-7 | 2-OnPr-4-CF$_3$ | N | CH | CH | N | CH | O | |
| 10-8 | 2-OnPr-4-CF$_3$ | N | CH | C—CF$_3$ | N | CH | S | |
| 10-9 | 4-CF$_3$ | N | C—Br | CH | N | CH | S | |
| 10-10 | 2-CF$_3$-3-Cl | N | CH | CH | CH | N | S | |
| 10-11 | 4-CF$_3$ | N | CH | C—CN | CH | CH | S | |
| 10-12 | 4-CF$_3$-2-OnPr | N | C—CN | CH | CH | CH | S | |
| 10-13 | 3-CF$_3$ | N | CH | N | C—CF$_3$ | C—CF$_3$ | S | |
| 10-14 | 3-Me | CH | N | C—CN | CH | CH | S | |
| 10-15 | 3-F | N | CH | CH | CH | N | SO$_2$ | |
| 10-16 | 2-CN | C—Me | N | CH | CH | CH | SO$_2$ | |
| 10-17 | 3-NO$_2$ | N | C—F | CH | CH | N | NH | |
| 10-18 | 4-CHO | N | C—Cl | CH | CH | N | NH | |
| 10-19 | 4-OMe | N | CH | N | CH | CH | NH | |
| 10-20 | 4-cPr | CH | C—Me | N | C—Me | CH | NiPr | |
| 10-21 | 2-OcHex | CH | CH | N | CH | CH | NMe | |
| 10-22 | 3-CH$_2$CH$_2$cPr | CH | CH | N | CH | CH | NMe | |

TABLE 11

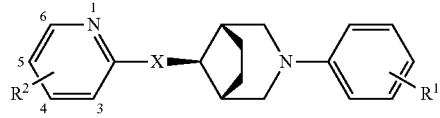

| Compound No. | R¹ | Q¹ | Q² | Q³ | Q⁴ | X | Physical constant [ ]: Melting point °C. | Remark |
|---|---|---|---|---|---|---|---|---|
| 11-1 | 2-OnPr-4-CF$_3$ | N | N | C—CF$_3$ | S | O | | vis |
| 11-2 | 3-F | CH | CH | CH | S | O | | |
| 11-3 | 2-CN | CH | CH | CH | O | O | | |
| 11-4 | 3-NO$_2$ | N | CH | C—Me | S | S | | |
| 11-5 | 4-CHO | N | C—F | CH | O | S | | |
| 11-6 | 4-OMe | N | N | CH | NH | S | | |
| 11-7 | 4-cPr | N | CH | CH | S | SO$_2$ | | |
| 11-8 | 2-OcHex | N | CH | CH | NMe | SO$_2$ | | |
| 11-9 | 3-CH$_2$CH$_2$cPr | N | N | CH | S | NH | | |
| 11-10 | 4-OCH$_2$cPr | N | CH | CH | NH | NH | | |
| 11-11 | 2-CHO | CH | N | CH | NH | NMe | | |

TABLE 12

| Compound No. | Q | X | R¹ | Physical constant [ ]: Melting point °C. |
|---|---|---|---|---|
| 12-1 | 5-CF$_3$ | O | 2-NO$_2$-4-CF$_3$ | [92-94] |
| 12-2 | 5-CF$_3$ | O | 2-NH$_2$-4-CF$_3$ | [120-122] |
| 12-3 | 5-CF$_3$ | O | 2-NHAc-4-CF$_3$ | [145-147] |
| 12-4 | 5-CF$_3$ | O | 2-OnPr-4-CF$_3$ | [104-106] |
| 12-5 | 5-CF$_3$ | O | 2-C(O)OiPr-4-CF$_3$ | nD21.8-1.5008 |
| 12-6 | 3-Cl | O | 2-CH=NOEt-4-CF$_3$ | |
| 12-7 | 4-CHO | O | (E)-2-CH=NOiPr-4-CF$_3$ | |
| 12-8 | 6-NO$_2$ | S | 2-CH=NO-propargyl-4-CF$_3$ | |
| 12-9 | 4-OCH=CH$_2$ | S | 2-(5-Me-oxazoline-2-yl)-4-CF$_3$ | |
| 12-10 | 5-OCF$_3$ | S | 2-CH$_2$OEt-4-CF$_3$ | |
| 12-11 | 4-OCH=CHCH$_2$CF$_3$ | S | 2-OMe-4-CF$_3$ | |
| 12-12 | 4-CO$_2$Et | S | (Z)-2-CH=NOiPr-4-CF$_3$ | |
| 12-13 | 6-OCF$_3$ | SO$_2$ | 2-C(O)OEt-4-CF$_3$ | |
| 12-14 | 6-CN | SO$_2$ | 2-C(O)OtBu-4-CF$_3$ | |
| 12-15 | 6-NO$_2$ | SO$_2$ | 2-C(O)OiPr-4-CF$_3$ | |
| 12-16 | 6-OcPr | NH | 6-Cl-2-C(O)OiPr-4-CF$_3$ | |
| 12-17 | 3-Me | NH | 3-Br | |
| 12-18 | 3-F | NEt | 4-cPr | |

TABLE 13

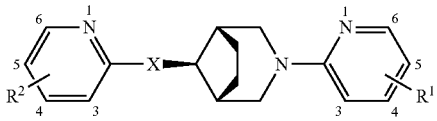

| Compound No. | R² | X | R¹ | Physical constant [ ]: Melting point °C |
|---|---|---|---|---|
| 13-1 | 5-CF₃ | O | 5-CF₃ | [79-81] |
| 13-2 | 6-OnPr-5-CF₃ | O | 5-CF₃ | [70-72] |
| 13-3 | 6-Cl-5-CF₃ | O | 5-CF₃ | [100-102] |
| 13-4 | 4-NO₂ | O | 4-cPr | |
| 13-5 | 3-CO₂iPr | O | 3-OcPr | |
| 13-6 | 4-OCH=CHF | S | 3,5-Me₂ | |
| 13-7 | 3-CH=CH₂ | S | 4-CF₃ | |
| 13-8 | 4-OCH₂cPr | S | 5-CO₂Et | |
| 13-9 | 5-CH₂cPr | S | 4-CH=CF₂ | |
| 13-10 | 3-OcPr | S | 5-CH=CMe₂ | |
| 13-11 | 4-cPr | SO₂ | 3-OCH₂CH₂cPr | |
| 13-12 | 4-OCHF₂ | NH | 4-CH₂cPr | |
| 13-13 | 3-OMe | NH | 3-OEt-4-cPr | |
| 13-14 | 4-CN | NH | 4-CHO | |
| 13-15 | 3-CHO | NH | 5-NO₂ | |
| 13-16 | 5-NO₂ | NMe | 5-CF₃ | |
| 13-17 | 4-F | NAc | 4-cPr | |
| 13-18 | 3,5-Me₂ | NAc | 4-CO₂Et | |

TABLE 14

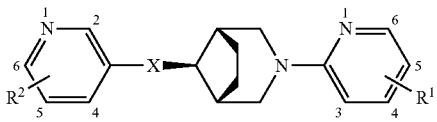

| Compound No. | R² | X | R¹ | Physical constant [ ]: Melting point °C |
|---|---|---|---|---|
| 14-1 | 2-OiBu-6-CF₃ | O | 5-CF₃ | nD22.5-1.5074 |
| 14-2 | 5-CF₃-6-OnPr | O | 5-CF₃ | [70-72] |
| 14-3 | 5-CHO | O | 5-CF₃ | |
| 14-4 | 4-OMe | O | 4-cPr | |
| 14-5 | 4-cPr | S | 3-OcPr | |
| 14-6 | 5-OcHex | S | 3,5-Me₂ | |
| 14-7 | 4-CH₂CH2cPr | S | 4-CF₃ | |
| 14-8 | 4-OCH₂cPr | S | 5-CO₂Et | |
| 14-9 | 4-OCH=CH₂ | S | 4-CH=CF₂ | |

TABLE 14-continued

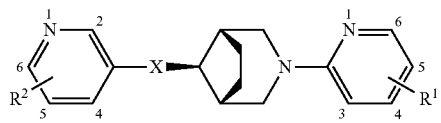

| Compound No. | R² | X | R¹ | Physical constant [ ]: Melting point °C |
|---|---|---|---|---|
| 14-10 | 5-OCF₃ | SO₂ | 5-CH=CMe₂ | |
| 14-11 | 4-OCH=CHCH₂CF₃ | SO | 3-OCH₂CH₂cPr | |
| 14-12 | 4-CO₂Et | SO | 4-CH₂cPr | |
| 14-13 | 6-F | NH | 3-OEt-4-cPr | |
| 14-14 | 6-CN | NH | 4-CHO | |
| 14-15 | 6-NO₂ | NH | 4-OMe | |
| 14-16 | 6-OcPr | NMe | 3-F | |
| 14-17 | 2-Me | NAc | 4-CO₂Me | |
| 14-18 | 2-F | NAc | 5-CH₂CH₂cPr | |

TABLE 15

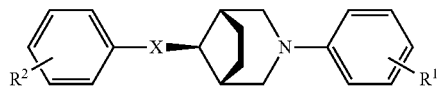

| Compound No. | R² | X | R¹ | Physical constant [ ]: Melting point °C |
|---|---|---|---|---|
| 15-1 | 2-OCH₂cPr-4-CF₃ | O | 4-CF₃ | vis |
| 15-2 | 2-OCH₂CH(F)Me-4-CF₃ | O | 2-F | |
| 15-3 | 2-OnPr-4-CF₃ | O | 3,4-Me₂ | |
| 15-4 | 2-OnPr-4-CF₃ | S | 3-OMe | |
| 15-5 | 4-CF₃ | S | 3-CHO | |
| 15-6 | 2-CF₃-3-Cl | S | 4-NO₂ | |
| 15-7 | 4-CF₃ | SO | 2-CO₂Et | |
| 15-8 | 4-CF₃-2-OnPr | SO | 3-CH=CHEt | |
| 15-9 | 3-CF₃ | SO | 4-OCH=CHMe | |
| 15-10 | 3-Me | SO₂ | 3-OCF₃ | |
| 15-11 | 3-F | SO₂ | 4-OCH=CF₂ | |
| 15-12 | 2-CN | NH | 2-CF₃-3-Cl | |
| 15-13 | 3-NO₂ | NH | 4-CF₃ | |
| 15-14 | 2-CH=CMe₂ | NH | 4-CF₃-2-OnPr | |
| 15-15 | 3-OCH=CF₂ | NAc | 3-CF₃ | |
| 15-16 | 4-CH₂CH₂CH₂cPr | NMe | 3-Me | |
| 15-17 | 2-OcPr-4-CF₃ | O | 4-CF₃ | vis |

TABLE 16

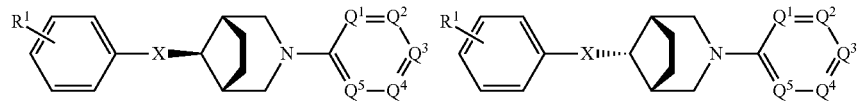

cis  trans

| Compound No. | R¹ | Q¹ | Q² | Q³ | Q⁴ | Q⁵ | X | Physical constant [ ]: Melting point °C | Remark |
|---|---|---|---|---|---|---|---|---|---|
| 16-1 | 2-OnPr-4-CF₃ | CH | N | C—CF₃ | CH | CH | O | [79-80] | cis |
| 16-2 | 2-OnPr-4-CF₃ | N | CH | C—CF₃ | N | CH | O | vis | cis |
| 16-3 | 2-OnPr-4-CF₃ | N | N | C—CF₃ | CH | CH | O | [100-103] | cis |
| 16-4 | 2-CO₂iPr-4-CF₃ | N | N | C—CF₃ | CH | CH | O | vis | cis |
| 16-5 | 2-CH₂OEt-4-CF₃ | N | N | C—CF₃ | CH | CH | O | [99-102] | cis |
| 16-6 | 2-OCH₂CH(Me)OMe-4-CF₃ | N | N | C—CF₃ | CH | CH | O | [103-105] | cis |
| 16-7 | 2-OnPr-4-CF₃ | N | N | C—Cl | CH | CH | O | [103-105] | cis |

TABLE 16-continued

| Compound No. | R¹ | Q¹ | Q² | Q³ | Q⁴ | Q⁵ | X | Physical constant [ ]: Melting point °C. | Remark |
|---|---|---|---|---|---|---|---|---|---|
| 16-8 | 2-OCH₂cPr-4-CF₃ | N | N | C—CN | CH | CH | O | [106-108] | cis |
| 16-9 | 2-OCH₂CH(Me)OMe-4-CF₃ | N | N | C—CN | CH | CH | O | [130-131] | cis |
| 16-10 | 2-CH₂OCH(Me)OMe-4-CF₃ | N | N | C—CF₃ | CH | CH | O | [132-135] | cis |
| 16-11 | 2-OCH₂cPr-4-CF₃ | N | N | C—CF₃ | CH | CH | O | [107-110] | cis |
| 16-12 | 2-ON=C(Me)₂-4-CF₃ | N | N | C—CF₃ | CH | CH | O | [121-124] | cis |
| 16-13 | 2-ON=C(Me)OMe-4-CF₃ | N | N | C—CF₃ | CH | CH | O | [108-111] | cis |
| 16-14 | 2-CO₂iPr-4-CF₃ | N | N | C—CN | CH | CH | O | [153-155] | cis |
| 16-15 | 2-ON=C(Me)₂-4-CF₃ | N | N | C—CN | CH | CH | O | [132-134] | cis |
| 16-16 | 2-OCH₂C(Me)=CH₂-4-CF₃ | N | N | C—CF₃ | CH | CH | O | [121-124] | cis |
| 16-17 | 2-OiBu-4-CF₃ | N | N | C—CF₃ | CH | CH | O | [107-110] | cis |
| 16-18 | 2-CH(OH)CH₂iPr-4-CF₃ | N | N | C—CF₃ | CH | CH | O | [72-75] | cis |
| 16-19 | 2-OCH₂CH(F)Me-4-CF₃ | N | N | C—CF₃ | CH | CH | O | [98-102] | cis |
| 16-20 | 2-Oallyl-4-CF₃ | N | N | C—CF₃ | CH | CH | O | [101-104] | cis |
| 16-21 | 2-Opropargyl-4-CF₃ | N | N | C—CF₃ | CH | CH | O | [107-111] | cis |
| 16-22 | 2-OnPr-4-CF₃ | N | N | C—CF₃ | CH | CH | O | [206-209] | sulfate cis |
| 16-23 | 2-OnPr-4-CF₃ | N | N | C—CF₃ | CH | CH | O | [220 up] | borate cis |
| 16-24 | 2-OCH₂cPr-4-CF₃ | CH | N | C—CN | CH | CH | O | nD23.3-1.5840 | cis |
| 16-25 | 2-OnPr-4-NO₂ | N | N | C—CF₃ | CH | CH | O | [128-132] | cis |
| 16-26 | 2-OnPr-4-Cl | N | N | C—CF₃ | CH | CH | O | nD23.4-1.5447 | cis |
| 16-27 | 4-CF₃ | N | N | C—CF₃ | CH | CH | O | [155-156] | cis |
| 16-28 | 4-OCF₃ | N | N | C—CF₃ | CH | CH | O |  | cis |
| 16-29 | 2-OCH₂CH(Cl)Me-4-CF₃ | N | N | C—CF₃ | CH | CH | O | [101-105] | cis |
| 16-30 | 2-OCH₂cPr-4-CN | N | N | C—CF₃ | CH | CH | O | [136-138] | cis |
| 16-31 | 2-NHnPr-4-CF₃ | N | N | C—CF₃ | CH | CH | O | [129-130] | cis |
| 16-32 | 2-NHCH₂cPr-4-CF₃ | N | N | C—CF₃ | CH | CH | O | [131-132] | cis |
| 16-33 | 2-Br-4-CF₃ | N | N | C—CF₃ | CH | CH | O | [126-127] | cis |
| 16-34 | 2-CF₃-3-Cl | N | CH | CH | N | CH | S |  | cis |
| 16-35 | 4-CF₃ | N | CH | CH | N | CH | S |  | cis |
| 16-36 | 4-CF₃-2-OnPr | N | CH | C—CF₃ | CH | N | S |  | cis |
| 16-37 | 3-CF₃ | N | C—Br | CH | CH | N | SO |  | cis |
| 16-38 | 3-Me | N | CH | N | CH | N | SO₂ |  | cis |
| 16-39 | 3-F | N | CH | C—CN | CH | N | NH |  | cis |
| 16-40 | 2-CN | N | C—CN | CH | CH | N | NMe |  | cis |
| 16-41 | 4-CF₃ | N | N | C—CF₃ | CH | CH | O | [159-160] | trans |
| 16-42 | 2-OnPr-4-CF₃ | N | N | C—CF₃ | CH | CH | O | [131-133] | trans |
| 16-43 | 2-OCH₂cPr-4-CF₃ | N | N | C—CF₃ | CH | CH | O | [112-114] | trans |
| 16-44 | 2-CF₃-3-Cl | N | N | C—CF₃ | CH | CH | S |  | trans |
| 16-45 | 4-CF₃ | N | CH | CH | N | CH | S |  | trans |
| 16-46 | 4-CF₃-2-OnPr | N | CH | CH | N | CH | S |  | trans |
| 16-47 | 3-CF₃ | N | CH | C—CF₃ | CH | N | SO |  | trans |
| 16-48 | 3-Me | N | C—Br | CH | CH | N | SO |  | trans |
| 16-49 | 3-F | N | CH | N | CH | N | SO |  | trans |
| 16-50 | 2-CN | N | CH | C—CN | CH | N | SO₂ |  | trans |
| 16-51 | 3-NO₂ | N | C—CN | CH | CH | N | SO₂ |  | trans |
| 16-52 | 4-CHO | N | N | C—CF₃ | CH | CH | SO₂ |  | trans |
| 16-53 | 4-OMe | N | N | C—CF₃ | CH | CH | SO₂ |  | trans |
| 16-54 | 4-cPr | N | N | C—CF₃ | CH | CH | NH |  | trans |
| 16-55 | 2-OcHex | N | N | C—CF₃ | CH | CH | NH |  | trans |
| 16-56 | 3-CH₂CH₂cPr | N | CH | CH | N | CH | NH |  | trans |
| 16-57 | 4-OCH₂cPr | N | CH | CH | N | CH | NMe |  | trans |
| 16-58 | 2-CHO | N | CH | CH | N | CH | NMe |  | trans |
| 16-59 | 3-OCH=CHMe | N | CH | CH | N | CH | NAc |  | trans |
| 16-60 | 2-CO₂Et | N | CH | CH | N | CH | NAc |  | trans |
| 16-61 | 4-CF₃ | N | CH | C—CF₃ | CH | CH | NH | [99-100] | cis |
| 16-62 | 4-CF₃ | N | CH | C—CF₃ | CH | CH | NAc | [116-119] | cis |
| 16-63 | 4-CF₃ | N | CH | C—CF₃ | CH | CH | NMe | [142-143] | cis |
| 16-64 | 2-NO₂-4-CF₃ | N | CH | C—CF₃ | CH | CH | NH | [140-143] | cis |
| 16-65 | 2-NO₂-4-CF₃ | N | CH | C—CF₃ | CH | CH | NMe | [124-127] | cis |
| 16-66 | 2-NO₂-4-CF₃ | N | CH | C—CF₃ | CH | CH | NnPr | amor | cis |
| 16-67 | 2-NO₂-4-CF₃ | N | CH | C—CF₃ | CH | CH | NnPr | amor | cis |
| 16-68 | 2-NO₂-4-CF₃ | N | CH | C—CF₃ | CH | CH | NEt | [112-114] | cis |
| 16-69 | 2-Me-4-OCF₃ | N | CH | C—CF₃ | CH | CH | NH | [89-90] | cis |
| 16-70 | 2-Me-4-OCF₃ | N | CH | C—CF₃ | CH | CH | NMe | nD24.6-1.5115 | cis |
| 16-71 | 2-OEt-4-tBu | N | CH | C—CF₃ | CH | CH | NH | vis | cis |
| 16-72 | 2-OEt-4-tBu | N | CH | C—CF₃ | CH | CH | NME | vis | cis |

TABLE 16-continued cis / trans structures with R¹-phenyl-X-bicyclic-N-heterocycle

| Compound No. | R¹ | Q¹ | Q² | Q³ | Q⁴ | Q⁵ | X | Physical constant [ ]: Melting point ° C. | Remark |
|---|---|---|---|---|---|---|---|---|---|
| 16-73 | 2-OnPr-4-CF₃ | N | CH | C—CF₃ | CH | CH | NH | [85-87] | cis |
| 16-74 | 2-OnPr-4-CF₃ | N | CH | C—CF₃ | CH | CH | NMe | [101-103] | cis |
| 16-75 | 2-nBu-4-CF₃ | N | CH | C—CF₃ | CH | CH | NH | [70-73] | cis |
| 16-76 | 2,6-nBu₂-4-CF₃ | N | CH | C—CF₃ | CH | CH | NH | nD22.0-1.5080 | cis |
| 16-77 | 5-Cl-2-OnPr-4-CF₃ | N | CH | C—CF₃ | CH | CH | NH | vis | cis |
| 16-78 | 2,6-Me₂-4-OCF₃ | N | CH | C—CF₃ | CH | CH | NH | [70-73] | cis |
| 16-79 | 2-OnPr-4-CF₃ | N | CH | C—CF₃ | CH | CH | NH | [103-104] | cis |
| 16-80 | 2-OnPr-4-CF₃ | N | CH | C—CF₃ | CH | CH | NH | [107-109] | cis |
| 16-81 | 2-OnPr-4-C(O)OtBu | N | CH | C—CF₃ | CH | CH | NH | [152-154] | cis |
| 16-82 | 2-OnPr-4-CF₃ | N | CH | C—CN | CH | CH | O | [95-99] | cis |
| 16-83 | 2-OCH₂cPr-4-CF₃ | N | CH | C—CN | CH | CH | O | [87-89] | cis |
| 16-84 | 2-OCH₂OMe-4-CF₃ | N | CH | C—CN | CH | CH | O | [117-119] | cis |
| 16-85 | 2-OCH₂CH₂OMe-4-CF₃ | N | CH | C—CN | CH | CH | O | [90-92] | cis |
| 16-86 | 2-OCH₂CH(OMe)Me-4-CF₃ | N | CH | C—CN | CH | CH | O | [78-81] | cis |
| 16-87 | 2-CO₂CHMe₂-4-CF₃ | N | CH | C—CN | CH | CH | O | [142-145] | cis |
| 16-88 | 2-CH₂OCH(Me)OMe-4-CF₃ | N | CH | C—CN | CH | CH | O | [119-122] | cis |
| 16-89 | 2-ON=CMe₂-4-CF₃ | N | CH | C—CN | CH | CH | O | [120-122] | cis |
| 16-90 | 2-ON=C(OMe)Me-4-CF₃ | N | CH | C—CN | CH | CH | O | [124-127] | cis |
| 16-91 | 2-ON=C(NH₂)Me-4-CF₃ | N | CH | C—CN | CH | CH | O | [142-145] | cis |

TABLE 17

| Compound No. | R¹ | Q¹ | Q² | Q³ | Q⁴ | X | Physical constant [ ]: Melting point ° C. |
|---|---|---|---|---|---|---|---|
| 17-1 | 2-OnPr-4-CF₃ | N | C—CF₃ | C—Br | S | O | vis |
| 17-2 | 2-OnPr-4-CF₃ | N | C—CF₃ | CH | S | O | vis |
| 17-3 | 2-OnPr-4-CF₃ | N | CH | C—CO₂Me | S | O | [90-91] |
| 17-4 | 2-OnPr-4-CF₃ | N | CH | C—CH₂OH | S | O | [135-137] |
| 17-5 | 2-OnPr-4-CF₃ | N | CH | C—CHO | S | O | [107-109] |
| 17-6 | 2-OnPr-4-CF₃ | N | CH | C—CF₂H | S | O | vis |
| 17-7 | 2-OCH₂cPr-4-CF₃ | N | N | C—CF₃ | S | O | vis |
| 17-8 | 2-CO₂iPr-4-CF₃ | N | N | C—CF₃ | S | O | nD22.3-1.5038 |
| 17-9 | 2-OnPr-4-CF₃ | N | N | C—CF₃ | S | O | nD22.4-1.5148 |
| 17-10 | 2-ON=C(Me)₂-4-CF₃ | N | N | C—CF₃ | S | O | [113-115] |
| 17-11 | 2-OnPr-4-CF₃ | CH | CH | CH | CH₂ | O | [140-142] |
| 17-12 | 2-OnPr-4-CF₃ | C—CN | C—CF₃ | N | NMe | O |  |
| 17-13 | 2-OnPr-4-CF₃ | C—C(O)NH₂ | C—CF₃ | N | NMe | O |  |
| 17-14 | 2-CF₃-3-Cl | CH | CH | CH | NH | S |  |
| 17-15 | 4-CF₃ | N | C—Cl | CH | NH | S |  |
| 17-16 | 4-CF₃-2-OnPr | N | CH | CH | NH | S |  |
| 17-17 | 3-CF₃ | N | C—CN | CH | NH | S |  |
| 17-18 | 3-Me | CH | CH | CH | O | SO |  |
| 17-19 | 3-F | C—Cl | CH | C—Cl | O | SO |  |
| 17-20 | 2-CN | N | CH | CH | O | SO |  |
| 17-21 | 3-NO₂ | N | CH | CH | O | SO |  |
| 17-22 | 4-CHO | CH | N | CH | O | SO |  |
| 17-23 | 4-OMe | CH | N | CH | O | SO₂ |  |
| 17-24 | 4-cPr | N | CH | CH | NMe | SO₂ |  |
| 17-25 | 2-OcHex | N | CH | CH | NMe | NH |  |
| 17-26 | 3-CH₂CH₂cPr | CH | N | CH | NMe | NH |  |
| 17-27 | 4-OCH₂cPr | CH | N | CH | NMe | NH |  |

TABLE 17-continued

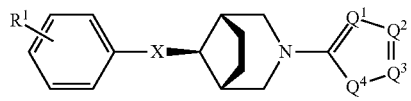

| Compound No. | R¹ | Q¹ | Q² | Q³ | Q⁴ | X | Physical constant [ ]: Melting point ° C. |
|---|---|---|---|---|---|---|---|
| 17-28 | 2-OnPr-4-CF₃ | C—CN | C—CF₃ | N | NMe | NMe | |
| 17-29 | 2-OnPr-4-CF₃ | CH | C—CF₃ | N | NMe | NMe | |
| 17-30 | 2-CHO | CH | N | CH | NMe | NAc | |

TABLE 18

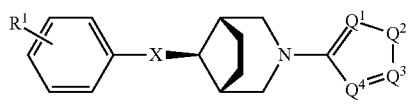

| Compound No. | R¹ | Q¹ | Q² | Q³ | Q⁴ | X | Physical constant [ ]: Melting point ° C. |
|---|---|---|---|---|---|---|---|
| 18-1 | 2-OnPr-4-CF₃ | N | NH | C—CF₃ | CH | O | [140-142] |
| 18-2 | 2-OnPr-4-CF₃ | N | CH₂ | C—Br | CH | O | |
| 18-3 | 2-OnPr-4-CF₃ | N | CMe₂ | CH | CH | O | |
| 18-4 | 2-OnPr-4-CF₃ | N | O | C—CO₂Me | CH | S | |
| 18-5 | 2-OnPr-4-CF₃ | N | O | C—CH₂OH | CH | S | |
| 18-6 | 2-OnPr-4-CF₃ | N | S | C—CHO | CH | SO₂ | |
| 18-7 | 2-OnPr-4-CF₃ | N | S | C—CF₂H | C—Cl | NH | |

TABLE 18-continued

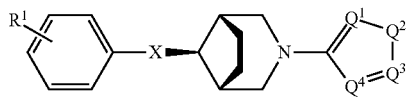

| Compound No. | R¹ | Q¹ | Q² | Q³ | Q⁴ | X | Physical constant [ ]: Melting point ° C. |
|---|---|---|---|---|---|---|---|
| 18-8 | 2-OCH₂cPr-4-CF₃ | N | NH | C—CF₃ | CMe | NH | |
| 18-9 | 2-CO₂iPr-4-CF₃ | N | NMe | C—CF₃ | C—CF₃ | NH | |
| 18-10 | 2-OnPr-4-CF₃ | N | NMe | C—CF₃ | C—CF₃ | NMe | |
| 18-11 | 2-ON=C(Me)₂-4-CF₃ | N | NMe | C—CF₃ | C—CF₃ | O | |
| 18-12 | 2-OnPr-4-CF₃ | CH | NMe | CH | CH | O | |

TABLE 19

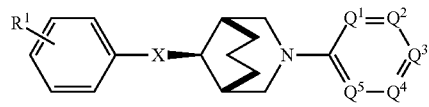

| Compound No. | R¹ | Q¹ | Q² | Q³ | Q⁴ | Q⁵ | X | Physical constant [ ]: Melting point ° C. |
|---|---|---|---|---|---|---|---|---|
| 19-1 | 2-OnPr-4-CF₃ | N | N | C—CF₃ | CH | CH | O | [125-127] |
| 19-2 | 2-OCH₂cPr-4-CF₃ | N | N | C—CF₃ | CH | CH | O | [115-118] |
| 19-3 | 2-OEt-4-CF₃ | N | N | C—CF₃ | CH | CH | O | [141-143] |
| 19-4 | 2-OCH₂OMe-4-CF₃ | N | N | C—CF₃ | CH | CH | O | [118-121] |
| 19-5 | 2-OiBu-4-CF₃ | N | N | C—CF₃ | CH | CH | O | [130-133] |
| 19-6 | 2-CO₂iPr-4-CF₃ | N | N | C—CF₃ | CH | CH | O | amor |
| 19-7 | 2-CH₂OEt-4-CF₃ | N | N | C—CF₃ | CH | CH | O | [144-146] |
| 19-8 | 2-OCH₂CH(Me)OMe-4-CF₃ | N | N | C—CF₃ | CH | CH | O | [114-115] |
| 19-9 | 2-OCH₂cPr-4-CF₃ | CH | CH | CH | CH | CH | O | vis |
| 19-10 | 2-OnPr-4-CF₃ | N | N | C—CF₃ | CH | CH | O | |
| 19-11 | 2-OnPr-4-CF₃ | N | N | C—CF₃ | CH | CH | O | |

TABLE 19-continued

| Compound No. | R¹ | Q¹ | Q² | Q³ | Q⁴ | Q⁵ | X | Physical constant [ ]: Melting point ° C. |
|---|---|---|---|---|---|---|---|---|
| 19-12 | 4-CF₃ | N | CH | CH | N | C—Me | S | |
| 19-13 | 2-CF₃-3-Cl | N | CH | CH | N | CH | S | |
| 19-14 | 4-CF₃ | N | CH | C—CF₃ | N | CH | S | |
| 19-15 | 4-CF₃-2-OnPr | N | C—Br | CH | N | CH | S | |
| 19-16 | 3-CF₃ | N | CH | CH | CH | N | S | |
| 19-17 | 3-Me | N | CH | C—CN | CH | CH | SO | |
| 19-18 | 3-F | N | C—CN | CH | CH | CH | SO | |
| 19-19 | 2-CN | N | CH | N | CH | CH | SO | |
| 19-20 | 3-NO₂ | CH | N | C—CN | CH | CH | SO₂ | |
| 19-21 | 2-CH=CMe₂ | N | CH | CH | CH | N | SO₂ | |
| 19-22 | 3-OCH=CF₂ | C—Me | N | CH | CH | CH | SO₂ | |
| 19-23 | 4-CH₂CH₂CH₂cPr | N | C—F | CH | CH | N | NH | |
| 19-24 | 2-OnPr-4-CF₃ | N | C—Cl | CH | CH | N | NH | |
| 19-25 | 2-OnPr-4-CF₃ | N | CH | CH | CH | CH | NH | |
| 19-26 | 4-CHO | CH | C—Me | N | C—Me | CH | NMe | |
| 19-27 | 3-OCF₃ | N | N | C—CF₃ | CH | CH | NMe | |
| 19-28 | 2-CO₂Et | N | N | CH | CH | CH | NAc | |
| 19-29 | 2-OnPr-4-CF₃ | CH | N | C—CF₃ | CH | CH | O | |
| 19-30 | 2-OnPr-4-CF₃ | N | CH | C—CF₃ | N | CH | O | |
| 19-31 | 2-OnPr-4-CF₃ | N | N | C—CF₃ | CH | CH | O | |
| 19-32 | 2-CO₂iPr-4-CF₃ | N | N | C—CF₃ | CH | CH | O | |
| 19-33 | 2-CH₂OEt-4-CF₃ | N | N | C—CF₃ | CH | CH | O | |
| 19-34 | 2-OCH₂CH(Me)OMe-4-CF₃ | N | N | C—CF₃ | CH | CH | O | |
| 19-35 | 2-OnPr-4-CF₃ | N | N | C—Cl | CH | CH | O | |
| 19-36 | 2-OCH₂cPr-4-CF₃ | N | N | C—CN | CH | CH | O | |
| 19-37 | 2-OCH₂CH(Me)OMe-4-CF₃ | N | N | C—CN | CH | CH | O | |
| 19-38 | 2-CH₂OCH(Me)OMe-4-CF₃ | N | N | C—CF₃ | CH | CH | O | |
| 19-39 | 2-OCH₂cPr-4-CF₃ | N | N | C—CF₃ | CH | CH | O | |
| 19-40 | 2-ON=C(Me)₂-4-CF₃ | N | N | C—CF₃ | CH | CH | O | |
| 19-41 | 2-ON=C(Me)OMe-4-CF₃ | N | N | C—CF₃ | CH | CH | O | |
| 19-42 | 2-CO₂iPr-4-CF₃ | N | N | C—CN | CH | CH | O | |

TABLE 20

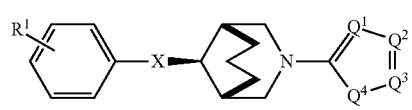

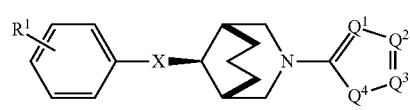

| Compound No. | R¹ | Q¹ | Q² | Q³ | Q⁴ | X | Physical constant [ ]: Melting point ° C. |
|---|---|---|---|---|---|---|---|
| 20-1 | 2-OcPr-4-CF₃ | N | N | C—CF₃ | S | O | [116-119] |
| 20-2 | 2-CO₂iPr-4-CF₃ | N | N | C—CF₃ | S | O | vis |
| 20-3 | 4-CF₃ | N | CH | C—Br | CH₂ | O | |
| 20-4 | 4-CF₃-2-OnPr | N | CMe | CH | CH₂ | O | |
| 20-5 | 3-CF₃ | N | N | C—CO₂Me | CH₂ | O | |
| 20-6 | 3-Me | N | N | C—CH₂OH | CH₂ | S | |
| 20-7 | 3-F | N | CH | C—CHO | CH₂ | S | |
| 20-8 | 2-CN | N | CH | C—CF₂H | CH₂ | S | |
| 20-9 | 3-NO₂ | N | N | C—CF₃ | CMe₂ | S | |
| 20-10 | 2-CH=CMe₂ | N | N | C—CF₃ | CMe₂ | SO | |
| 20-11 | 3-OCH=CF₂ | N | N | C—CF₃ | CMe₂ | SO | |
| 20-12 | 4-CH₂CH₂CH₂cPr | N | N | C—CF₃ | CH₂ | SO₂ | |
| 20-13 | 2-OnPr-4-CF₃ | CH | N | CH | CH₂ | SO₂ | |
| 20-14 | 2-OnPr-4-CF₃ | N | CH | C—Br | CH₂ | SO₂ | |
| 20-15 | 4-CHO | N | CMe | CH | CH₂ | NH | |
| 20-16 | 3-OCF₃ | N | CMe | C—CO₂Me | CH₂ | NH | |
| 20-17 | 4-cPr | CH | CH | N | NH | NMe | |

TABLE 21

| Compound No. | Cy¹ | X | Y | Cy² | Physical constant [ ]: Melting point °C. | cis/trans |
|---|---|---|---|---|---|---|
| 21-1 | cyclopropylmethoxy-(4-CF₃)phenyl | O | NH | 5-CF₃-pyridin-2-yl | vis | cis |
| 21-2 | cyclopropylmethoxy-(4-CF₃)phenyl | O | NH | 5-CF₃-pyridin-2-yl | 165-167 | trans |
| 21-3 | cyclopropylmethoxy-(4-CF₃)phenyl | O | NMe | 5-CF₃-pyridin-2-yl | vis | cis |
| 21-4 | cyclopropylmethoxy-(4-CF₃)phenyl | O | NCO₂Me | 5-CF₃-pyridin-2-yl | 120-122 | cis |
| 21-5 | cyclopropylmethoxy-(4-CF₃)phenyl | O | S | 5-CF₃-pyridin-2-yl | nD22.2-1.5418 | cis |
| 21-6 | cyclopropylmethoxy-(4-CF₃)phenyl | O | SO₂ | 5-CF₃-pyridin-2-yl | 155-158 | cis |
| 21-7 | 5-CF₃-pyridin-2-yl | O | O | 5-CF₃-1,3,4-thiadiazol-2-yl | 156-157 | trans |
| 21-8 | 5-CF₃-pyridin-2-yl | O | O | 5-CF₃-1,3,4-thiadiazol-2-yl | 124-125 | cis |

TABLE 21-continued

| Compound No. | Cy¹ | X | Y | Cy² | Physical constant [ ]: Melting point °C. | cis/trans |
|---|---|---|---|---|---|---|
| 21-9 | 5-CF₃-pyridin-2-yl | O | O | 6-CF₃-pyridazin-3-yl | 125-126 | trans |
| 21-10 | 5-CF₃-3-Cl-pyridin-2-yl | O | O | 5-CF₃-1,3,4-thiadiazol-2-yl | vis | cis |
| 21-11 | 4-CF₃-phenyl | O | O | 5-CF₃-1,3,4-thiadiazol-2-yl | 127-128 | trans |
| 21-12 | 4-CF₃-phenyl | O | O | 5-CF₃-1,3,4-thiadiazol-2-yl | 146-147 | cis |
| 21-13 | 4-CF₃-phenyl | O | O | 6-CF₃-pyridazin-3-yl | 102-103 | trans |
| 21-14 | 4-CF₃-2-(cyclopropylmethoxy)phenyl | O | S | 6-CF₃-pyridazin-3-yl | 125-128 | cis |
| 21-15 | 4-CF₃-2-(cyclopropylmethoxy)phenyl | O | S | 5-CF₃-1,3,4-thiadiazol-2-yl | 52-55 | cis |
| 21-16 | 4-CF₃-2-(cyclopropylmethoxy)phenyl | O | S | 5-CN-pyridin-2-yl | 136-138 | cis |
| 21-17 | 4-CF₃-2-(cyclopropylmethoxy)phenyl | O | SO₂ | 5-CN-pyridin-2-yl | 200 up | cis |

TABLE 21-continued

| Compound No. | Cy¹ | X | Y | Cy² | Physical constant [ ]: Melting point ° C. | cis/trans |
|---|---|---|---|---|---|---|
| 21-18 | cyclopropylmethoxy-(CF₃)phenyl | O | O | pyridazine-CF₃ | 93-95 | cis |
| 21-19 | F₃CO-naphthyl | O | SO₂ | Cl-pyrazine | | cis |
| 21-20 | vinyl-furanyl | O | SO₂ | pyridazine-CF₃ | | trans |
| 21-21 | Me₂N-thienyl | S | NH | OMe,CN-pyridyl | | cis |
| 21-22 | vinyloxy-pyrrolyl | S | S | pyrrolyl-CO₂Et | | cis |
| 21-23 | MeO-oxazolyl | S | S | Ph-imidazolyl | | trans |
| 21-24 | EtO₂C-imidazolyl | S | O | vinyl-furanyl | | trans |
| 21-25 | MeCONH-thiazolyl | SO | NMe | F₃CO-pyrazinyl | | cis |
| 21-26 | NC-thiadiazolyl | SO₂ | NH | pyridazine-O-N=C(Me)₂ | | trans |

TABLE 21-continued
| | Cy¹—X—[cis bicycle]—N—Cy² | | | Cy¹—X⋯[trans bicycle]—N—Cy² | | |
|---|---|---|---|---|---|---|
| | cis | | | trans | | |
| Compound No. | Cy¹ | X | Y | Cy² | Physical constant [ ]: Melting point ° C. | cis/trans |
|---|---|---|---|---|---|---|
| 21-27 | 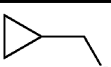 | NH | SO₂ | 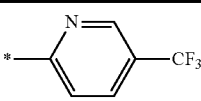 | | cis |
| 21-28 | 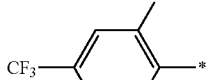 | NH | S | 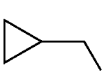 | | trans |
| 21-29 | 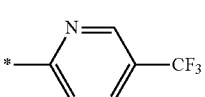 | NMe | O | 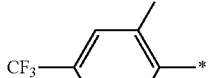 | | cis |
TABLE 22
| | Cy¹—X—[cis bicycle]—N—Cy² | | | Cy¹—X⋯[trans bicycle]—N—Cy² | | |
|---|---|---|---|---|---|---|
| | cis | | | trans | | |
| Compound No. | Cy¹ | X | Y | Cy² | Physical constant [ ]: Melting point ° C. | cis/trans |
|---|---|---|---|---|---|---|
| 22-1 | 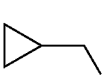 | O | NH | | | cis |
| 22-2 | 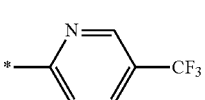 | O | NH | | | trans |
| 22-3 | 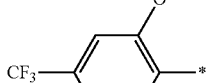 | O | NMe | | | cis |

TABLE 22-continued

| Compound No. | Cy¹ | X | Y | Cy² | Physical constant [ ]: Melting point ° C. | cis/trans |
|---|---|---|---|---|---|---|
| 22-4 | cyclopropyl-CH₂-O-C₆H₃(CF₃)- | O | NCO₂Me | pyridyl-CF₃ | | cis |
| 22-5 | cyclopropyl-CH₂-O-C₆H₃(CF₃)- | O | S | pyridyl-CF₃ | | cis |
| 22-6 | cyclopropyl-CH₂-O-C₆H₃(CF₃)- | O | SO₂ | pyridyl-CF₃ | | cis |
| 22-7 | CF₃-pyridyl- | O | O | nPrO-C₆H₃-CF₃ | | cis |
| 22-8 | CF₃-pyridyl- | O | O | iPrOCO-C₆H₃-CF₃ | | cis |
| 22-9 | CF₃-pyridyl- | O | O | pyridyl-CF₃ | | trans |
| 22-10 | CF₃-pyridyl(Cl)- | O | O | 1,3,4-thiadiazolyl-CF₃ | | cis |
| 22-11 | CF₃-C₆H₄- | O | O | 1,3,4-thiadiazolyl-CF₃ | | trans |
| 22-12 | CF₃-C₆H₄- | O | O | 1,3,4-thiadiazolyl-CF₃ | | cis |

TABLE 22-continued
| Compound No. | Cy¹ | X | Y | Cy² | Physical constant [ ]: Melting point ° C. | cis/trans |
|---|---|---|---|---|---|---|
| 22-13 | 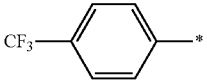 [SMILES: *c1ccc(C(F)(F)F)cc1] | O | O | 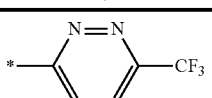 | | trans |
| 22-14 | 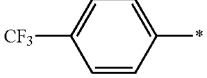 | O | S |  | | cis |
| 22-15 | 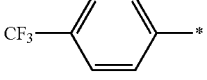 | O | S | 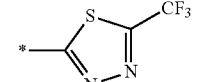 | | cis |
| 22-16 | 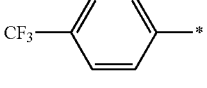 | O | S | 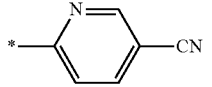 [SMILES: *c1ccc(C#N)cn1] | | cis |
| 22-17 | 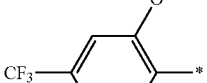 | O | SO₂ | 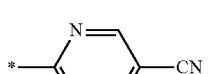 | | cis |
| 22-18 | 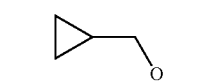 | O | O |  | | cis |
| 22-19 | 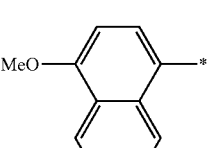 | O | SO₂ | 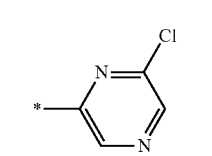 [SMILES: *c1cncc(Cl)n1] | | cis |
| 22-20 | 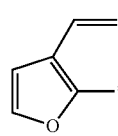 | O | SO₂ | 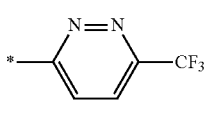 | | trans |

TABLE 22-continued

| Compound No. | Cy¹ | X | Y | Cy² | Physical constant [ ]: Melting point ° C. | cis/trans |
|---|---|---|---|---|---|---|
| 22-21 | Me₂N-thiazole-* (2-NMe₂-thiazol-5-yl) | S | NH | 2-OMe-3-CN-pyridin-6-yl | | cis |
| 22-22 | 5-(vinyloxy)-1H-pyrrol-2-yl | S | S | 5-(CO₂Et)-1H-pyrrol-2-yl | | cis |
| 22-23 | 4-Et-oxazol-2-yl | S | S | 5-Ph-1H-imidazol-2-yl | | trans |
| 22-24 | 4-(EtO₂C)-1H-imidazol-2-yl | S | O | 5-vinyl-furan-2-yl | | trans |
| 22-25 | 4-(MeCONH)-thiazol-2-yl | SO | NMe | 3-(F₃CO)-pyrazin-2-yl | | cis |
| 22-26 | 5-CN-1,3,4-thiadiazol-2-yl | SO₂ | NH | 6-(O-N=C(Me)₂)-pyridazin-3-yl | | trans |
| 22-27 | 5-CHO-1,3,4-oxadiazol-2-yl | NH | SO₂ | 6-SMe-pyridin-2-yl | | cis |
| 22-28 | 5-cyclopropyl-1H-1,2,4-triazol-3-yl | NH | S | 5-NO₂-1,3,4-thiadiazol-2-yl | | trans |
| 22-29 | 6-Ph-pyridazin-3-yl | NMe | O | 2-OMe-3-CN-pyridin-6-yl | | cis |
| 22-30 | 6-(CF₃)-pyridazin-3-yl | O | O | 2-(cPrCH₂O)-5-CF₃-phenyl | | cis |

FORMULATION EXAMPLES

Insecticides/Acaricides

Although a few examples regarding compositions of the present invention are shown next, additives and proportions added are changeable over a wide range without being limited to these examples. Parts in Formulation Examples show parts by weight.

Formulation Example 1

Wettable Powder

| | |
|---|---|
| Compound of the present invention | 40 parts |
| Diatomaceous earth | 53 parts |
| Higher alcohol sulfate ester | 4 parts |
| Alkylnaphthalenesulfonate salt | 3 parts |

The above components were mixed homogenously and ground finely to obtain a wettable powder with 40% of active ingredient.

Formulation Example 2

Emulsion

| | |
|---|---|
| Compound of the present invention | 30 parts |
| Xylene | 33 parts |
| Dimethylformamide | 30 parts |
| Polyoxyethylene alkyl allyl ether | 7 parts |

The above components were mixed and dissolved to obtain an emulsion with 30% of active ingredient.

Formulation Example 3

Dusting Powder

| | |
|---|---|
| Compound of the present invention | 10 parts |
| Talc | 89 parts |
| Polyoxyethylene alkyl allyl ether | 1 part |

The above components were mixed homogenously and ground finely to obtain a dusting powder with 10% of active ingredient.

Formulation Example 4

Granules

| | |
|---|---|
| Compound of the present invention | 5 parts |
| Clay | 73 parts |
| Bentonite | 20 parts |
| Sodium dioctylsulfosuccinate salt | 1 part |
| Sodium phosphate | 1 part |

The above components were mixed and ground well and, after adding water thereto and kneading together, granulated and dried to obtain granules with 5% of active ingredient.

Formulation Example 5

Suspending Agent

| | |
|---|---|
| Compound of the present invention | 10 parts |
| Sodium lignin sulfonate | 4 parts |
| Sodium dodecylbenzenesulfonate | 1 part |
| Xanthan gum | 0.2 parts |
| Water | 84.8 parts |

The above components were mixed and subjected to wet-grinding until the grain size of 1 μm or less was achieved to obtain a suspending agent with 10% of active ingredient.

Test Example 1

Effectiveness Against *Tetranychus urticae*

17 adult female *Tetranychus urticae*, which were resistant to organophosphorus pesticides, were inoculated on the first true leaf of a common bean, which was seeded in a pot with a diameter of 9 cm, where 7 to 10 days had passed after the germination. After the inoculation, the drug solution, which was prepared by following the method of the wettable powder shown in Example 1 of the drugs and by diluting with water to achieve the compound concentration of 125 ppm, was applied. The pot was placed in a temperature-controlled room where the temperature and humidity were set to 25° C. and 65% respectively, and the adulticidal rate was examined 3 days after the application. The test was repeated twice.

As a result, the compounds below showed the insecticidal rate of 100%. 1-1, 1-4 to 1-7, 1-10, 1-13, 1-17, 1-18, 1-21 to 1-29, 1-31 to 1-36, 1-39 to 1-47, 1-50, 1-51, 1-54, 2-3, 3-1, 4-5, 4-7, 4-9, 4-13, 4-16, 4-18 to 4-20, 4-53 to 4-55, 4-58 to 4-61, 4-64, 4-70, 4-71, 5-1 to 5-8, 10-1, 11-1, 13-2, 15-1, 15-17, 16-1 to 16-26, 16-61, 16-65, 16-69, 16-73 to 16-75, 16-78, 16-82 to 16-91, 17-2, 17-3, 17-7 to 17-10, 19-1 to 19-3, 21-1, 21-3, 21-5, 21-6, 21-14 to 21-16

Test Example 2

Effectiveness Against *Panonychus citri*

10 adult female *Panonychus citri* were inoculated on the leaf of a mandarin orange, which was placed in a petri dish. After the inoculation, the drug solution, which was prepared by following the method of the emulsion shown in Example 2 of the drugs and by diluting with water to achieve the compound concentration of 125 ppm, was applied using a rotary spreading tower. The dish was placed in a temperature-controlled room where the temperature and humidity were set to 25° C. and 65% respectively, adults were removed 3 days after the application, and whether eggs laid during these 3 days could grow to become adults was examined on the 11th day.

As a result, the compounds below showed the insecticidal rate of 100%. 1-1, 1-5, 1-7, 1-13, 1-17, 1-24, 1-31, 1-32, 1-47, 1-50, 3-1, 4-5, 4-53, 4-54, 4-58 to 4-61, 4-64, 4-70, 4-71, 5-1, 5-2, 5-4, 5-8, 10-1, 12-4, 16-1 to 16-13, 16-15 to 16-20, 16-22, 16-23, 16-26, 16-61, 16-73, 16-83, 16-84, 16-89 to 16-91, 17-7, 17-9, 17-10, 19-1 to 19-3, 21-5, 21-6, 21-13

Test Example 3

Effectiveness Test Against *Pseudaletia separata*

0.2 ml of a commercially available artificial diet (Insecta LFS manufactured by Nihon Nosan-Kogyo Co., Ltd) was put into a plastic test tube with a volume of 1.4 ml and was used as a test diet. The compound was adjusted to prepare 1% solution using dimethylsulfoxide containing 0.5% tween 20 and this solution was applied by adding dropwise onto the surface of the diet in an amount equivalent to 10 μg of the compound. 2 second-instar larvae of *Pseudaletia separate* were inoculated to each test tube and the tubes were sealed with plastic lids. The tubes were left at 25° C. and the insecticidal rate and amount of food ingested were examined after 5 days. The test was repeated twice.

In the present test, the compounds below were effective by showing the insecticidal rate of 100%, or the amount of food ingested was 10% or less compared to the solvent control group.

4-3, 4-4, 16-1, 16-2, 17-3, 17-7 to 17-9

Test Example 4

Effectiveness Test Against *Culex pipiens molestus*

10 larvae of *Culex pipiens molestus*, which were hatched 1 day before, and 0.225 ml of distilled water containing 0.5 mg of feed for aquarium fish (TetraMin® manufactured by Tetra Japan Co. Ltd) were put into a polystyrene test vessel with a volume of 0.3 ml. The compound was adjusted to prepare 1% solution using dimethylsulfoxide containing 0.5% tween 20 and further diluted to 0.01% with distilled water. 0.025 ml of this diluted drug solution was added to the test vessel with *Culex pipiens molestus* and was stirred (final compound concentration 0.001%). The vessels were left at 25° C. and the insecticidal rate was examined after 2 days. The test was repeated twice.

In the present test, the compound below was effective by showing the insecticidal rate of 90% or more.

4-3

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

INDUSTRIAL APPLICABILITY

According to the present invention, it is possible to provide cyclic amine compounds with a novel structure, salts thereof, N-oxides thereof, or intermediates thereof during the production and especially agents for pest control with excellent bioactivities in terms of insecticidal/acaricidal activities and high safety.

What is claimed:

1. Cyclic amine compounds represented by formula (1B)

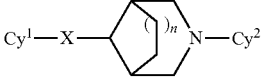

or salts thereof or N-oxides thereof,
wherein $Cy^1$ represents an unsubstituted or substituted phenyl group;
X represents oxygen;
n represents 1 or 2;
$Cy^2$ represents an unsubstituted or substituted pyridazyl group.

2. Cyclic amine compounds according to claim 1, wherein $Cy^1$ represents a phenyl group substituted by hydroxyl, thiol, halogen, cyano, nitro, formyl, unsubstituted or substituted amino, alkyl, alkenyl, alkynyl, alkoxy, alkenyloxy, alkynyloxy, aryloxy, heteroaryloxy, haloalkyl, haloalkoxy, alkylthiocarbonyl, alkylsulfonylamino, arylsulfonylamino, heteroarylsulfonylamino, alkylcarbonylamino, alkoxycarbonylamino, haloalkylsulfonylamino, bis(alkylsulfonyl)amino, bis(haloalkylsulfonyl)amino, unsubstituted or substituted hydrazino, alkoxycarbonyl, aryl, aralkyl, unsaturated 5-membered heterocycle, unsaturated 5-membered heterocycle alkyl, unsaturated 6-membered heterocycle, unsaturated 6-membered heterocycle alkyl, sarutated heterocyclic group, sarutated heterocyclic alkyl, N-unsubstituted- or N-substituted iminoalkyl, N-unsubstituted- or N-substituted hydrazinocarbonyl, N-unsubstituted- or N-substituted aminocarbonyl, alkylthio, alkenylthio, alkynylthio, arylthio, heteroarylthio, aralkylthio, alkylsulfonyl, alkenylsulfonyl, alkynylsulfonyl, arylsulfonyl, heteroarylsulfonyl,

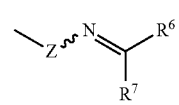
(a)

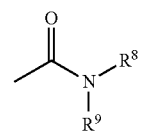
(b)

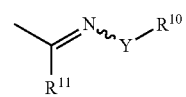
(c)

aralkylsulfonyl, or a group represented by formula (a), (b), or (c) below:
wherein
$R^6$ and $R^7$ each independently represents hydrogen, unsubstituted or substituted hydrocarbon, unsubstituted or substituted heterocyclic group, unsubstituted or substituted amino, hydrocarbonoxy, or hydrocarbonthio;
$R^8$ and $R^{11}$ each independently represents hydrogen, unsubstituted or substituted hydrocarbon, unsubstituted or substituted heterocyclic group, or unsubstituted or substituted amino;
$R^9$ represents hydrogen or unsubstituted or substituted hydrocarbon;

$R^{10}$ represents hydrogen, unsubstituted or substituted hydrocarbon, or unsubstituted or substituted heterocyclic group;

Y and Z each independently represent oxygen, or unsubstituted or substituted nitrogen;

$R^6$ and $R^7$, $R^8$ and $R^9$, and $R^{10}$ and $R^{11}$ may bond to form rings and both groups in the pair represent functional groups, which may integrate to form a ring.

3. Cyclic amine compounds according to claim 1, wherein $Cy^2$ represents a pyridazyl group substituted by halogen, nitro, or haloalkyl.

4. Agents for pest control comprising at least one of the cyclic amine compounds of claim 1.

* * * * *